US012521506B2

(12) United States Patent
Yu et al.

(10) Patent No.: US 12,521,506 B2
(45) Date of Patent: Jan. 13, 2026

(54) LOW DEADSPACE AIRWAY ADAPTER

(71) Applicant: MASIMO CORPORATION, Irvine, CA (US)

(72) Inventors: Edmond Wing-Lun Yu, Irvine, CA (US); Mahdi Mohammadi, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 815 days.

(21) Appl. No.: 17/664,766

(22) Filed: May 24, 2022

(65) Prior Publication Data

US 2022/0379059 A1 Dec. 1, 2022

Related U.S. Application Data

(60) Provisional application No. 63/220,134, filed on Jul. 9, 2021, provisional application No. 63/193,446, filed on May 26, 2021.

(51) Int. Cl.

| | |
|---|---|
| ***A61M 16/04*** | (2006.01) |
| ***A61M 16/08*** | (2006.01) |
| *A61M 16/00* | (2006.01) |

(52) U.S. Cl.

CPC ...... *A61M 16/0463* (2013.01); *A61M 16/085* (2014.02); *A61M 2016/0036* (2013.01)

(58) Field of Classification Search

None

See application file for complete search history.

(56) References Cited

U.S. PATENT DOCUMENTS

| | | | |
|---|---|---|---|
| 3,460,532 | A | 8/1969 | Bird et al. |
| 3,485,243 | A | 12/1969 | Bird et al. |
| 3,530,856 | A | 9/1970 | Bird et al. |
| 3,902,500 | A | 9/1975 | Dryden |

(Continued)

FOREIGN PATENT DOCUMENTS

| | | |
|---|---|---|
| DE | 20 2010 018 390 | 6/2016 |
| DE | 10 2010 064 624 | 10/2017 |

(Continued)

OTHER PUBLICATIONS

US 2024/0016391 A1, 01/2024, Lapotko et al. (withdrawn)

(Continued)

*Primary Examiner* — LaToya M Louis

(74) *Attorney, Agent, or Firm* — Knobbe, Martens, Olson & Bear, LLP

(57) ABSTRACT

In some implementations, a low dead space airway adapter for sampling fluid flowing through a ventilation assembly includes an outer wall configured to couple to an endotracheal (ET) tube adapter and an internal projection positioned at least partially within an internal cavity defined by the outer wall and configured to extend within an internal cavity of the ET tube adapter when the airway adapter is in use. The internal projection can include a fluid passageway configured for fluid communication with at least a portion of the internal cavity of the ET tube adapter and a free end comprising an opening in fluid communication with the fluid passageway. At least a portion of the free end can be chamfered around the opening and configured to contact an inner surface of the ET tube adapter when the outer wall is coupled to the ET tube adapter.

16 Claims, 29 Drawing Sheets

(56) References Cited

U.S. PATENT DOCUMENTS 4,558,708 A * 12/1985 Labuda ................. A61M 16/08 128/207.14
4,622,968 A 11/1986 Persson
4,640,278 A 2/1987 Barry
4,681,094 A 7/1987 Rolnick
4,729,765 A 3/1988 Eckels et al.
4,805,613 A 2/1989 Bird
4,848,331 A 7/1989 Northway-Meyer
4,852,583 A 8/1989 Walker
4,960,128 A 10/1990 Gordon et al.
4,964,408 A 10/1990 Hink et al.
5,067,492 A 11/1991 Yelderman et al.
5,101,817 A 4/1992 Etter
5,213,109 A 5/1993 Susi
5,319,355 A 6/1994 Russek
5,337,744 A 8/1994 Branigan
5,341,805 A 8/1994 Stavridi et al.
5,355,876 A * 10/1994 Brodsky ........... A61M 16/0463 128/207.14
5,377,676 A 1/1995 Vari et al.
5,431,170 A 7/1995 Mathews
5,436,499 A 7/1995 Namavar et al.
5,456,252 A 10/1995 Vari et al.
5,479,934 A 1/1996 Imran
5,482,036 A 1/1996 Diab et al.
5,494,043 A 2/1996 O'Sullivan et al.
5,533,511 A 7/1996 Kaspari et al.
5,570,682 A 11/1996 Johnson
5,582,161 A 12/1996 Kee
5,590,649 A 1/1997 Caro et al.
5,591,130 A 1/1997 Denton
5,602,924 A 2/1997 Durand et al.
5,638,816 A 6/1997 Kiani-Azarbayjany et al.
5,638,818 A 6/1997 Diab et al.
5,642,726 A * 7/1997 Owens ............. A61M 16/0463 128/207.14
5,645,440 A 7/1997 Tobler et al.
5,658,353 A 8/1997 Layton
5,671,914 A 9/1997 Kalkhoran et al.
5,726,440 A 3/1998 Kalkhoran et al.
D393,830 S 4/1998 Tobler et al.
5,743,262 A 4/1998 Lepper, Jr. et al.
5,747,806 A 5/1998 Khalil et al.
5,750,994 A 5/1998 Schlager
5,758,644 A 6/1998 Diab et al.
5,760,910 A 6/1998 Lepper, Jr. et al.
5,789,660 A * 8/1998 Kofoed .................. G01N 21/05 73/23.3
5,885,248 A 3/1999 Denton
5,890,929 A 4/1999 Mills et al.
5,919,134 A 7/1999 Diab
5,987,343 A 11/1999 Kinast
5,997,343 A 12/1999 Mills et al.
6,002,952 A 12/1999 Diab et al.
6,010,937 A 1/2000 Karam et al.
6,014,890 A 1/2000 Breen
6,027,452 A 2/2000 Flaherty et al.
6,040,578 A 3/2000 Malin et al.
6,044,843 A 4/2000 O'Neil et al.
6,066,204 A 5/2000 Haven
6,067,984 A 5/2000 Piper
6,076,519 A 6/2000 Johnson
6,095,986 A 8/2000 Braig et al.
6,109,259 A 8/2000 Fitzgerald
6,115,673 A 9/2000 Malin et al.
6,124,597 A 9/2000 Shehada et al.
6,128,521 A 10/2000 Marro et al.
6,129,675 A 10/2000 Jay
6,144,868 A 11/2000 Parker
6,152,754 A 11/2000 Gerhardt et al.
6,184,521 B1 2/2001 Coffin, IV et al.
6,190,327 B1 2/2001 Isaacson et al.
6,202,646 B1 3/2001 Camodeca et al.
6,216,692 B1 4/2001 Todokoro et al.
6,232,609 B1 5/2001 Snyder et al.
6,241,683 B1 6/2001 Macklem et al.
6,253,097 B1 6/2001 Aronow et al.
6,255,708 B1 7/2001 Sudharsanan et al.
6,258,040 B1 7/2001 Yamamori et al.
6,273,087 B1 8/2001 Boussignac et al.
6,280,381 B1 8/2001 Malin et al.
6,285,896 B1 9/2001 Tobler et al.
6,308,089 B1 10/2001 von der Ruhr et al.
6,317,627 B1 11/2001 Ennen et al.
6,321,100 B1 11/2001 Parker
6,334,065 B1 12/2001 Al-Ali et al.
6,360,114 B1 3/2002 Diab et al.
6,368,283 B1 4/2002 Xu et al.
6,386,199 B1 5/2002 Alfery
6,411,373 B1 6/2002 Garside et al.
6,415,167 B1 7/2002 Blank et al.
6,430,437 B1 8/2002 Marro
6,430,525 B1 8/2002 Weber et al.
6,463,311 B1 10/2002 Diab
6,470,199 B1 10/2002 Kopotic et al.
6,487,429 B2 11/2002 Hockersmith et al.
6,505,059 B1 1/2003 Kollias et al.
6,525,386 B1 2/2003 Mills et al.
6,526,300 B1 2/2003 Kiani et al.
6,534,012 B1 3/2003 Hazen et al.
6,534,769 B1 3/2003 Graham
6,542,764 B1 4/2003 Al-Ali et al.
6,550,476 B1 4/2003 Ryder
6,580,086 B1 6/2003 Schulz et al.
6,584,336 B1 6/2003 Ali et al.
6,587,196 B1 7/2003 Stippick et al.
6,587,199 B1 7/2003 Luu
6,597,932 B2 7/2003 Tian et al.
6,606,511 B1 8/2003 Ali et al.
6,612,304 B1 9/2003 Cise et al.
6,631,717 B1 10/2003 Rich et al.
6,635,559 B2 10/2003 Greenwald et al.
6,639,668 B1 10/2003 Trepagnier
6,640,116 B2 10/2003 Diab
6,640,117 B2 10/2003 Makarewicz et al.
6,658,276 B2 12/2003 Kiani et al.
6,661,161 B1 12/2003 Lanzo et al.
6,662,804 B2 12/2003 Ortiz
6,697,656 B1 2/2004 Al-Ali
6,697,658 B2 2/2004 Al-Ali
RE38,476 E 3/2004 Diab et al.
RE38,492 E 4/2004 Diab et al.
6,738,652 B2 5/2004 Mattu et al.
6,760,607 B2 7/2004 Al-Ali
6,788,965 B2 9/2004 Ruchti et al.
6,816,241 B2 11/2004 Grubisic
6,822,564 B2 11/2004 Al-Ali
RE38,700 E 2/2005 Briggs, III
6,850,787 B2 2/2005 Weber et al.
6,850,788 B2 2/2005 Al-Ali
6,860,264 B2 3/2005 Christopher
6,876,931 B2 4/2005 Lorenz et al.
6,884,222 B1 4/2005 Braig et al.
6,920,345 B2 7/2005 Al-Ali et al.
6,926,005 B1 8/2005 Colman et al.
6,934,570 B2 8/2005 Kiani et al.
6,935,338 B1 8/2005 Triunfo, Jr.
6,943,348 B1 9/2005 Coffin IV
6,956,649 B2 10/2005 Acosta et al.
6,961,598 B2 11/2005 Diab
6,970,792 B1 11/2005 Diab
6,985,764 B2 1/2006 Mason et al.
6,990,364 B2 1/2006 Ruchti et al.
6,998,247 B2 2/2006 Monfre et al.
7,003,338 B2 2/2006 Weber et al.
7,015,451 B2 3/2006 Dalke et al.
7,027,849 B2 4/2006 Al-Ali
7,059,322 B2 6/2006 Rich et al.
D526,719 S 8/2006 Richie, Jr. et al.
7,086,402 B2 8/2006 Peterson
7,096,052 B2 8/2006 Mason et al.
7,096,054 B2 8/2006 Abdul-Hafiz et al.
D529,616 S 10/2006 Deros et al.
7,133,710 B2 11/2006 Acosta et al.

(56) References Cited

U.S. PATENT DOCUMENTS 7,142,901 B2 11/2006 Kiani et al.
7,207,329 B2 4/2007 Bowden
7,216,531 B2 5/2007 Young et al.
7,225,006 B2 5/2007 Al-Ali et al.
RE39,672 E 6/2007 Shehada et al.
7,225,805 B2 6/2007 Bacon
7,254,429 B2 8/2007 Schurman et al.
7,254,431 B2 8/2007 Al-Ali et al.
7,254,434 B2 8/2007 Schulz et al.
7,274,955 B2 9/2007 Kiani et al.
D554,263 S 10/2007 Al-Ali et al.
7,280,858 B2 10/2007 Al-Ali et al.
7,289,835 B2 10/2007 Mansfield et al.
7,292,883 B2 11/2007 De Felice et al.
7,335,164 B2 2/2008 Mace et al.
7,341,559 B2 3/2008 Schulz et al.
7,341,563 B2 3/2008 Rich et al.
7,343,186 B2 3/2008 Lamego et al.
D566,282 S 4/2008 Al-Ali et al.
7,356,365 B2 4/2008 Schurman
7,371,981 B2 5/2008 Abdul-Hafiz
7,373,193 B2 5/2008 Al-Ali et al.
7,377,794 B2 5/2008 Al-Ali et al.
7,395,158 B2 7/2008 Monfre et al.
7,415,297 B2 8/2008 Al-Ali et al.
7,438,683 B2 10/2008 Al-Ali et al.
7,445,602 B2 11/2008 Yamamori et al.
7,455,644 B2 11/2008 Yamamori et al.
7,483,729 B2 1/2009 Al-Ali et al.
D587,657 S 3/2009 Al-Ali et al.
7,500,482 B2 3/2009 Biederman
7,500,483 B2 3/2009 Colman et al.
7,500,950 B2 3/2009 Al-Ali et al.
7,509,494 B2 3/2009 Al-Ali
7,510,849 B2 3/2009 Schurman et al.
7,514,725 B2 4/2009 Wojtczuk et al.
7,519,406 B2 4/2009 Blank et al.
D592,507 S 5/2009 Wachman et al.
7,530,942 B1 5/2009 Diab
7,593,230 B2 9/2009 Abul-Haj et al.
7,596,398 B2 9/2009 Al-Ali et al.
7,606,608 B2 10/2009 Blank et al.
7,620,674 B2 11/2009 Ruchti et al.
D606,659 S 12/2009 Kiani et al.
7,629,039 B2 12/2009 Eckerbom et al.
7,640,140 B2 12/2009 Ruchti et al.
7,647,083 B2 1/2010 Al-Ali et al.
D609,193 S 2/2010 Al-Ali et al.
D614,305 S 4/2010 Al-Ali et al.
7,697,966 B2 4/2010 Monfre et al.
7,698,105 B2 4/2010 Ruchti et al.
RE41,317 E 5/2010 Parker
RE41,333 E 5/2010 Blank et al.
7,729,733 B2 6/2010 Al-Ali et al.
7,747,319 B2 6/2010 Freeman
7,748,280 B2 7/2010 Jaffe et al.
7,761,127 B2 7/2010 Al-Ali et al.
7,764,982 B2 7/2010 Dalke et al.
D621,516 S 8/2010 Kiani et al.
7,791,155 B2 9/2010 Diab
RE41,912 E 11/2010 Parker
7,880,626 B2 2/2011 Al-Ali et al.
7,909,772 B2 3/2011 Popov et al.
7,919,713 B2 4/2011 Al-Ali et al.
7,937,128 B2 5/2011 Al-Ali
7,937,129 B2 5/2011 Mason et al.
7,941,199 B2 5/2011 Kiani
7,957,780 B2 6/2011 Lamego et al.
7,962,188 B2 6/2011 Kiani et al.
7,976,472 B2 7/2011 Kiani
7,980,246 B2 7/2011 Rich et al.
7,990,382 B2 8/2011 Kiani
8,008,088 B2 8/2011 Bellott et al.
RE42,753 E 9/2011 Kiani-Azarbayjany et al.
8,028,701 B2 10/2011 Al-Ali et al.
8,042,545 B2 10/2011 Schwartz et al.
8,048,040 B2 11/2011 Kiani
8,050,728 B2 11/2011 Al-Ali et al.
8,083,684 B2 12/2011 Palatnik
RE43,169 E 2/2012 Parker
8,118,620 B2 2/2012 Al-Ali et al.
8,130,105 B2 3/2012 Al-Ali et al.
8,163,241 B2 4/2012 Burke et al.
8,182,443 B1 5/2012 Kiani
8,190,223 B2 5/2012 Al-Ali et al.
8,203,438 B2 6/2012 Kiani et al.
8,203,704 B2 6/2012 Merritt et al.
8,219,172 B2 7/2012 Schurman et al.
8,224,411 B2 7/2012 Al-Ali et al.
8,229,532 B2 7/2012 Davis
8,233,955 B2 7/2012 Al-Ali et al.
8,235,042 B2 8/2012 Newman, Jr.
8,255,026 B1 8/2012 Al-Ali
8,265,723 B1 9/2012 McHale et al.
8,274,360 B2 9/2012 Sampath et al.
8,280,473 B2 10/2012 Al-Ali
8,282,570 B2 10/2012 Rich et al.
8,315,683 B2 11/2012 Al-Ali et al.
RE43,860 E 12/2012 Parker
8,346,330 B2 1/2013 Lamego
8,353,295 B2 1/2013 Haveru
8,353,842 B2 1/2013 Al-Ali et al.
8,355,766 B2 1/2013 MacNeish, III et al.
8,374,665 B2 2/2013 Lamego
8,388,353 B2 3/2013 Kiani et al.
8,401,602 B2 3/2013 Kiani
8,414,499 B2 4/2013 Al-Ali et al.
8,418,524 B2 4/2013 Al-Ali
8,428,967 B2 4/2013 Olsen et al.
8,430,817 B1 4/2013 Al-Ali et al.
8,437,825 B2 5/2013 Dalvi et al.
8,448,642 B2 5/2013 Tappehorn et al.
8,455,290 B2 6/2013 Siskavich
8,457,707 B2 6/2013 Kiani
8,471,713 B2 6/2013 Poeze et al.
8,473,020 B2 6/2013 Kiani et al.
8,490,622 B2 7/2013 Stenzler et al.
8,496,000 B2 7/2013 Keith
8,509,867 B2 8/2013 Workman et al.
8,515,509 B2 8/2013 Bruinsma et al.
8,523,781 B2 9/2013 Al-Ali
D692,145 S 10/2013 Al-Ali et al.
8,571,617 B2 10/2013 Reichgott et al.
8,571,618 B1 10/2013 Lamego et al.
8,571,619 B2 10/2013 Al-Ali et al.
8,573,039 B2 11/2013 Holl
8,577,431 B2 11/2013 Lamego et al.
8,584,345 B2 11/2013 Al-Ali et al.
8,588,880 B2 11/2013 Abdul-Hafiz et al.
8,630,691 B2 1/2014 Lamego et al.
8,641,631 B2 2/2014 Sierra et al.
8,642,966 B2 2/2014 Weckstrom et al.
8,652,060 B2 2/2014 Al-Ali
8,666,468 B1 3/2014 Al-Ali
8,670,811 B2 3/2014 O'Reilly
RE44,823 E 4/2014 Parker
RE44,875 E 4/2014 Kiani et al.
8,688,183 B2 4/2014 Bruinsma et al.
8,690,799 B2 4/2014 Telfort et al.
8,702,627 B2 4/2014 Telfort et al.
8,707,950 B1 4/2014 Rubin
8,712,494 B1 4/2014 MacNeish et al.
8,715,206 B2 5/2014 Telfort et al.
8,723,677 B1 5/2014 Kiani
8,740,792 B1 6/2014 Kiani et al.
8,755,535 B2 6/2014 Telfort et al.
8,755,872 B1 6/2014 Marinow
8,764,671 B2 7/2014 Kiani
8,768,423 B2 7/2014 Shakespeare et al.
8,771,204 B2 7/2014 Telfort et al.
8,781,544 B2 7/2014 Al-Ali et al.
8,783,247 B2 7/2014 Newman, Jr.
8,790,268 B2 7/2014 Al-Ali
8,801,613 B2 8/2014 Al-Ali et al.

(56) References Cited

U.S. PATENT DOCUMENTS

| | | | | |
|---|---|---|---|---|
| 8,821,397 | B2 | 9/2014 | Al-Ali et al. | |
| 8,821,415 | B2 | 9/2014 | Al-Ali et al. | |
| 8,830,449 | B1 | 9/2014 | Lamego et al. | |
| 8,840,549 | B2 | 9/2014 | Al-Ali et al. | |
| 8,852,094 | B2 | 10/2014 | Al-Ali et al. | |
| 8,852,994 | B2 | 10/2014 | Wojtczuk et al. | |
| 8,893,719 | B2 | 11/2014 | Lavi et al. | |
| 8,897,847 | B2 | 11/2014 | Al-Ali | |
| 8,911,377 | B2 | 12/2014 | Al-Ali | |
| 8,925,549 | B2 | 1/2015 | Turek et al. | |
| 8,989,831 | B2 | 3/2015 | Al-Ali et al. | |
| 8,992,430 | B2 | 3/2015 | Colman et al. | |
| 8,998,809 | B2 | 4/2015 | Kiani | |
| 9,066,666 | B2 | 6/2015 | Kiani | |
| 9,066,680 | B1 | 6/2015 | Al-Ali et al. | |
| 9,095,316 | B2 | 8/2015 | Welch et al. | |
| 9,106,038 | B2 | 8/2015 | Telfort et al. | |
| 9,107,625 | B2 | 8/2015 | Telfort et al. | |
| 9,131,881 | B2 | 9/2015 | Diab et al. | |
| 9,138,180 | B1 | 9/2015 | Coverston et al. | |
| 9,153,112 | B1 | 10/2015 | Kiani et al. | |
| 9,192,329 | B2 | 11/2015 | Al-Ali | |
| 9,192,351 | B1 | 11/2015 | Telfort et al. | |
| 9,195,385 | B2 | 11/2015 | Al-Ali et al. | |
| 9,211,095 | B1 | 12/2015 | Al-Ali | |
| 9,218,454 | B2 | 12/2015 | Kiani et al. | |
| 9,245,668 | B1 | 1/2016 | Vo et al. | |
| 9,267,572 | B2 | 2/2016 | Barker et al. | |
| 9,277,880 | B2 | 3/2016 | Poeze et al. | |
| 9,283,343 | B2 | 3/2016 | Pizzini | |
| 9,295,804 | B2 | 3/2016 | Schätzl | |
| 9,307,928 | B1 | 4/2016 | Al-Ali et al. | |
| 9,323,894 | B2 | 4/2016 | Kiani | |
| D755,392 | S | 5/2016 | Hwang et al. | |
| 9,326,712 | B1 | 5/2016 | Kiani | |
| 9,352,115 | B1 | 5/2016 | DeStefano | |
| 9,392,945 | B2 | 7/2016 | Al-Ali et al. | |
| 9,398,837 | B2 | 7/2016 | Vazales et al. | |
| 9,408,542 | B1 | 8/2016 | Kinast et al. | |
| 9,436,645 | B2 | 9/2016 | Al-Ali et al. | |
| 9,445,714 | B2 | 9/2016 | Vazales et al. | |
| 9,445,759 | B1 | 9/2016 | Lamego et al. | |
| 9,468,734 | B2 * | 10/2016 | Dainobu ................ | A61B 5/097 |
| 9,474,474 | B2 | 10/2016 | Lamego et al. | |
| 9,480,435 | B2 | 11/2016 | Olsen | |
| 9,498,150 | B2 | 11/2016 | Colman et al. | |
| 9,510,779 | B2 | 12/2016 | Poeze et al. | |
| 9,517,024 | B2 | 12/2016 | Kiani et al. | |
| 9,532,722 | B2 | 1/2017 | Lamego et al. | |
| 9,560,996 | B2 | 2/2017 | Kiani | |
| 9,566,018 | B2 | 2/2017 | Yamamori | |
| 9,572,948 | B2 | 2/2017 | Haveri et al. | |
| 9,579,012 | B2 | 2/2017 | Vazales et al. | |
| 9,579,039 | B2 | 2/2017 | Jansen et al. | |
| 9,592,353 | B2 | 3/2017 | Roy | |
| 9,622,692 | B2 | 4/2017 | Lamego et al. | |
| D788,312 | S | 5/2017 | Al-Ali et al. | |
| 9,649,054 | B2 | 5/2017 | Lamego et al. | |
| 9,675,773 | B2 | 6/2017 | Colman et al. | |
| 9,687,626 | B2 | 6/2017 | Amirav et al. | |
| 9,697,928 | B2 | 7/2017 | Al-Ali et al. | |
| 9,707,363 | B2 | 7/2017 | Mansfield et al. | |
| 9,713,687 | B2 | 7/2017 | Leamon et al. | |
| 9,717,458 | B2 | 8/2017 | Lamego et al. | |
| 9,724,016 | B1 | 8/2017 | Al-Ali et al. | |
| 9,724,024 | B2 | 8/2017 | Al-Ali | |
| 9,724,025 | B1 | 8/2017 | Kiani et al. | |
| 9,749,232 | B2 | 8/2017 | Sampath et al. | |
| 9,750,442 | B2 | 9/2017 | Olsen | |
| 9,750,461 | B1 | 9/2017 | Telfort | |
| 9,750,907 | B2 | 9/2017 | Librett et al. | |
| 9,775,545 | B2 | 10/2017 | Al-Ali et al. | |
| 9,778,079 | B1 | 10/2017 | Al-Ali et al. | |
| 9,782,077 | B2 | 10/2017 | Lamego et al. | |
| 9,787,568 | B2 | 10/2017 | Lamego et al. | |
| 9,808,188 | B1 | 11/2017 | Perea et al. | |
| 9,808,612 | B2 * | 11/2017 | Gulliver ............ | A61M 16/0816 |
| 9,833,588 | B2 | 12/2017 | Fuller et al. | |
| 9,839,379 | B2 | 12/2017 | Al-Ali et al. | |
| 9,839,381 | B1 | 12/2017 | Weber et al. | |
| 9,847,749 | B2 | 12/2017 | Kiani et al. | |
| 9,848,800 | B1 | 12/2017 | Lee et al. | |
| 9,855,395 | B2 | 1/2018 | Jaffe et al. | |
| 9,861,298 | B2 | 1/2018 | Eckerbom et al. | |
| 9,861,305 | B1 | 1/2018 | Weber et al. | |
| 9,877,650 | B2 | 1/2018 | Muhsin et al. | |
| 9,891,079 | B2 | 2/2018 | Dalvi | |
| 9,924,897 | B1 | 3/2018 | Abdul-Hafiz | |
| 9,936,917 | B2 | 4/2018 | Poeze et al. | |
| 9,955,937 | B2 | 5/2018 | Telfort | |
| 9,965,946 | B2 | 5/2018 | Al-Ali et al. | |
| D820,865 | S | 6/2018 | Muhsin et al. | |
| 9,986,952 | B2 | 6/2018 | Dalvi et al. | |
| 10,004,863 | B2 | 6/2018 | Vazales et al. | |
| D822,215 | S | 7/2018 | Al-Ali et al. | |
| D822,216 | S | 7/2018 | Barker et al. | |
| 10,010,276 | B2 | 7/2018 | Al-Ali et al. | |
| 10,086,138 | B1 | 10/2018 | Novak, Jr. | |
| 10,111,591 | B2 | 10/2018 | Dyell et al. | |
| D833,624 | S | 11/2018 | DeJong et al. | |
| 10,123,729 | B2 | 11/2018 | Dyell et al. | |
| 10,136,839 | B2 | 11/2018 | Yamamori | |
| D835,282 | S | 12/2018 | Barker et al. | |
| D835,283 | S | 12/2018 | Barker et al. | |
| D835,284 | S | 12/2018 | Barker et al. | |
| D835,285 | S | 12/2018 | Barker et al. | |
| 10,149,616 | B2 | 12/2018 | Al-Ali et al. | |
| 10,154,815 | B2 | 12/2018 | Al-Ali et al. | |
| 10,159,412 | B2 | 12/2018 | Lamego et al. | |
| 10,179,221 | B2 | 1/2019 | Wruck | |
| 10,188,348 | B2 | 1/2019 | Al-Ali et al. | |
| RE47,218 | E | 2/2019 | Al-Ali | |
| RE47,244 | E | 2/2019 | Kiani et al. | |
| RE47,249 | E | 2/2019 | Kiani et al. | |
| 10,205,291 | B2 | 2/2019 | Scruggs et al. | |
| 10,226,187 | B2 | 3/2019 | Al-Ali et al. | |
| 10,231,657 | B2 | 3/2019 | Al-Ali et al. | |
| 10,231,670 | B2 | 3/2019 | Blank et al. | |
| RE47,353 | E | 4/2019 | Kiani et al. | |
| 10,279,247 | B2 | 5/2019 | Kiani | |
| 10,292,664 | B2 | 5/2019 | Al-Ali | |
| 10,299,720 | B2 | 5/2019 | Brown et al. | |
| 10,300,226 | B2 | 5/2019 | Cohen | |
| 10,327,337 | B2 | 6/2019 | Schmidt et al. | |
| 10,327,713 | B2 | 6/2019 | Barker et al. | |
| 10,332,630 | B2 | 6/2019 | Al-Ali | |
| 10,337,948 | B2 | 7/2019 | Heimer et al. | |
| 10,342,456 | B2 | 7/2019 | Haveri | |
| 10,369,313 | B2 | 8/2019 | White et al. | |
| 10,383,520 | B2 | 8/2019 | Wojtczuk et al. | |
| 10,383,527 | B2 | 8/2019 | Al-Ali | |
| 10,388,120 | B2 | 8/2019 | Muhsin et al. | |
| 10,398,872 | B2 | 9/2019 | Schätzl | |
| D864,120 | S | 10/2019 | Forrest et al. | |
| 10,441,181 | B1 | 10/2019 | Telfort et al. | |
| 10,441,196 | B2 | 10/2019 | Eckerbom et al. | |
| 10,441,380 | B2 | 10/2019 | Vazales et al. | |
| 10,441,735 | B1 | 10/2019 | Zhou | |
| 10,448,844 | B2 | 10/2019 | Al-Ali et al. | |
| 10,448,871 | B2 | 10/2019 | Al-Ali et al. | |
| 10,456,038 | B2 | 10/2019 | Lamego et al. | |
| 10,463,340 | B2 | 11/2019 | Telfort et al. | |
| 10,471,159 | B1 | 11/2019 | Lapotko et al. | |
| 10,505,311 | B2 | 12/2019 | Al-Ali et al. | |
| 10,506,950 | B2 | 12/2019 | Luttrell | |
| 10,524,738 | B2 | 1/2020 | Olsen | |
| 10,532,174 | B2 | 1/2020 | Al-Ali | |
| 10,537,285 | B2 | 1/2020 | Shreim et al. | |
| 10,542,903 | B2 | 1/2020 | Al-Ali et al. | |
| 10,555,678 | B2 | 2/2020 | Dalvi et al. | |
| 10,568,553 | B2 | 2/2020 | O'Neil et al. | |
| 10,608,817 | B2 | 3/2020 | Haider et al. | |
| D880,477 | S | 4/2020 | Forrest et al. | |
| 10,617,302 | B2 | 4/2020 | Al-Ali et al. | |

(56) References Cited

U.S. PATENT DOCUMENTS 10,617,335 B2 4/2020 Al-Ali et al.
10,637,181 B2 4/2020 Al-Ali et al.
D886,849 S 6/2020 Muhsin et al.
D887,548 S 6/2020 Abdul-Hafiz et al.
D887,549 S 6/2020 Abdul-Hafiz et al.
10,667,764 B2 6/2020 Ahmed et al.
D890,708 S 7/2020 Forrest et al.
10,721,785 B2 7/2020 Al-Ali
10,736,518 B2 8/2020 Al-Ali et al.
10,750,984 B2 8/2020 Pauley et al.
10,751,492 B2 8/2020 Mansfield et al.
D897,098 S 9/2020 Al-Ali
10,758,694 B2 9/2020 Nye
10,779,098 B2 9/2020 Iswanto et al.
10,806,880 B2 10/2020 Miller
10,820,833 B2 11/2020 Chapman
10,827,961 B1 11/2020 Iyengar et al.
10,828,007 B1 11/2020 Telfort et al.
10,832,818 B2 11/2020 Muhsin et al.
10,849,554 B2 12/2020 Shreim et al.
10,856,750 B2 12/2020 Indorf et al.
10,864,338 B2 12/2020 Crowell
D906,970 S 1/2021 Forrest et al.
D908,213 S 1/2021 Abdul-Hafiz et al.
10,918,281 B2 2/2021 Al-Ali et al.
10,932,705 B2 3/2021 Muhsin et al.
10,932,729 B2 3/2021 Kiani et al.
10,939,878 B2 3/2021 Kiani et al.
10,956,950 B2 3/2021 Al-Ali et al.
D916,135 S 4/2021 Indorf et al.
D917,046 S 4/2021 Abdul-Hafiz et al.
D917,550 S 4/2021 Indorf et al.
D917,564 S 4/2021 Indorf et al.
D917,704 S 4/2021 Al-Ali et al.
10,987,066 B2 4/2021 Chandran et al.
10,991,135 B2 4/2021 Al-Ali et al.
D919,094 S 5/2021 Al-Ali et al.
D919,100 S 5/2021 Al-Ali et al.
11,006,867 B2 5/2021 Al-Ali
D921,202 S 6/2021 Al-Ali et al.
11,024,064 B2 6/2021 Muhsin et al.
11,026,604 B2 6/2021 Chen et al.
D925,597 S 7/2021 Chandran et al.
D927,699 S 8/2021 Al-Ali et al.
11,076,777 B2 8/2021 Lee et al.
11,114,188 B2 9/2021 Poeze et al.
D933,232 S 10/2021 Al-Ali et al.
D933,233 S 10/2021 Al-Ali et al.
D933,234 S 10/2021 Al-Ali et al.
11,145,408 B2 10/2021 Sampath et al.
11,147,518 B1 10/2021 Al-Ali et al.
11,185,262 B2 11/2021 Al-Ali et al.
11,191,484 B2 12/2021 Kiani et al.
D946,596 S 3/2022 Ahmed
D946,597 S 3/2022 Ahmed
D946,598 S 3/2022 Ahmed
D946,617 S 3/2022 Ahmed
11,272,839 B2 3/2022 Al-Ali et al.
11,289,199 B2 3/2022 Al-Ali
RE49,034 E 4/2022 Al-Ali
11,298,021 B2 4/2022 Muhsin et al.
D950,580 S 5/2022 Ahmed
D950,599 S 5/2022 Ahmed
D950,738 S 5/2022 Al-Ali et al.
D957,648 S 7/2022 Al-Ali
11,382,567 B2 7/2022 O'Brien et al.
11,389,093 B2 7/2022 Triman et al.
11,406,286 B2 8/2022 Al-Ali et al.
11,417,426 B2 8/2022 Muhsin et al.
11,439,329 B2 9/2022 Lamego
11,445,948 B2 9/2022 Scruggs et al.
D965,789 S 10/2022 Al-Ali et al.
D967,433 S 10/2022 Al-Ali et al.
11,464,410 B2 10/2022 Muhsin
11,504,058 B1 11/2022 Sharma et al.
11,504,066 B1 11/2022 Dalvi et al.
D971,933 S 12/2022 Ahmed
D973,072 S 12/2022 Ahmed
D973,685 S 12/2022 Ahmed
D973,686 S 12/2022 Ahmed
D974,193 S 1/2023 Forrest et al.
D979,516 S 2/2023 Al-Ali et al.
D980,091 S 3/2023 Forrest et al.
11,596,363 B2 3/2023 Lamego
11,627,919 B2 4/2023 Kiani et al.
11,637,437 B2 4/2023 Al-Ali et al.
D985,498 S 5/2023 Al-Ali et al.
11,653,862 B2 5/2023 Dalvi et al.
D989,112 S 6/2023 Muhsin et al.
D989,327 S 6/2023 Al-Ali et al.
11,678,829 B2 6/2023 Al-Ali et al.
11,679,579 B2 6/2023 Al-Ali
11,684,296 B2 6/2023 Vo et al.
11,692,934 B2 7/2023 Normand et al.
11,701,043 B2 7/2023 Al-Ali et al.
D997,365 S 8/2023 Hwang
11,721,105 B2 8/2023 Ranasinghe et al.
11,730,379 B2 8/2023 Ahmed et al.
D998,625 S 9/2023 Indorf et al.
D998,630 S 9/2023 Indorf et al.
D998,631 S 9/2023 Indorf et al.
D999,244 S 9/2023 Indorf et al.
D999,245 S 9/2023 Indorf et al.
D999,246 S 9/2023 Indorf et al.
11,766,198 B2 9/2023 Pauley et al.
D1,000,975 S 10/2023 Al-Ali et al.
11,803,623 B2 10/2023 Kiani et al.
11,832,940 B2 12/2023 Diab et al.
D1,013,179 S 1/2024 Al-Ali et al.
11,872,156 B2 1/2024 Telfort et al.
11,879,960 B2 1/2024 Ranasinghe et al.
11,883,129 B2 1/2024 Olsen
11,896,767 B2 * 2/2024 Dong .................... G16H 40/63
D1,022,729 S 4/2024 Forrest et al.
11,951,186 B2 4/2024 Krishnamani et al.
11,974,833 B2 5/2024 Forrest et al.
11,986,067 B2 5/2024 Al-Ali et al.
11,986,289 B2 5/2024 Dalvi et al.
11,986,305 B2 5/2024 Al-Ali et al.
2001/0034477 A1 10/2001 Mansfield et al.
2001/0039483 A1 11/2001 Brand et al.
2002/0010401 A1 1/2002 Bushmakin et al.
2002/0058864 A1 5/2002 Mansfield et al.
2002/0100474 A1 8/2002 Kellner et al.
2002/0133080 A1 9/2002 Apruzzese et al.
2003/0013975 A1 1/2003 Kiani
2003/0018243 A1 1/2003 Gerhardt et al.
2003/0144582 A1 7/2003 Cohen et al.
2003/0156288 A1 8/2003 Barnum et al.
2003/0212312 A1 11/2003 Coffin, IV et al.
2004/0106163 A1 6/2004 Workman, Jr. et al.
2005/0055276 A1 3/2005 Kiani et al.
2005/0234317 A1 10/2005 Kiani
2006/0073719 A1 4/2006 Kiani
2006/0189871 A1 8/2006 Al-Ali et al.
2007/0073116 A1 3/2007 Kiani et al.
2007/0180140 A1 8/2007 Welch et al.
2007/0225612 A1 9/2007 Mace et al.
2007/0244377 A1 10/2007 Cozad et al.
2008/0064965 A1 3/2008 Jay et al.
2008/0094228 A1 4/2008 Welch et al.
2008/0103375 A1 5/2008 Kiani
2008/0221418 A1 9/2008 Al-Ali et al.
2009/0036759 A1 2/2009 Ault et al.
2009/0093687 A1 4/2009 Telfort et al.
2009/0095926 A1 4/2009 MacNeish, III
2009/0247984 A1 10/2009 Lamego et al.
2009/0275844 A1 11/2009 Al-Ali
2010/0004518 A1 1/2010 Vo et al.
2010/0030040 A1 2/2010 Poeze et al.
2010/0036272 A1 2/2010 Mace et al.
2010/0099964 A1 4/2010 O'Reilly et al.
2010/0234718 A1 9/2010 Sampath et al.
2010/0270257 A1 10/2010 Wachman et al.

(56) References Cited

U.S. PATENT DOCUMENTS

| | | | |
|---|---|---|---|
| 2011/0028806 | A1 | 2/2011 | Merritt et al. |
| 2011/0028809 | A1 | 2/2011 | Goodman |
| 2011/0040197 | A1 | 2/2011 | Welch et al. |
| 2011/0082711 | A1 | 4/2011 | Poeze et al. |
| 2011/0087081 | A1 | 4/2011 | Kiani et al. |
| 2011/0118561 | A1 | 5/2011 | Tari et al. |
| 2011/0137297 | A1 | 6/2011 | Kiani et al. |
| 2011/0172498 | A1 | 7/2011 | Olsen et al. |
| 2012/0123231 | A1 | 5/2012 | O'Reilly |
| 2012/0165629 | A1 | 6/2012 | Merritt et al. |
| 2012/0209084 | A1 | 8/2012 | Olsen et al. |
| 2012/0226117 | A1 | 9/2012 | Lamego et al. |
| 2012/0283524 | A1 | 11/2012 | Kiani et al. |
| 2013/0023775 | A1 | 1/2013 | Lamego et al. |
| 2013/0060147 | A1 | 3/2013 | Welch et al. |
| 2013/0096405 | A1 | 4/2013 | Garfio |
| 2013/0296672 | A1 | 11/2013 | O'Neil et al. |
| 2013/0345921 | A1 | 12/2013 | Al-Ali et al. |
| 2014/0166076 | A1 | 6/2014 | Kiani et al. |
| 2014/0180160 | A1 | 6/2014 | Brown et al. |
| 2014/0187973 | A1 | 7/2014 | Brown et al. |
| 2014/0275871 | A1 | 9/2014 | Lamego et al. |
| 2014/0275872 | A1 | 9/2014 | Merritt et al. |
| 2014/0316217 | A1 | 10/2014 | Purdon et al. |
| 2014/0316218 | A1 | 10/2014 | Purdon et al. |
| 2014/0323897 | A1 | 10/2014 | Brown et al. |
| 2014/0323898 | A1 | 10/2014 | Purdon et al. |
| 2015/0005600 | A1 | 1/2015 | Blank et al. |
| 2015/0011907 | A1 | 1/2015 | Purdon et al. |
| 2015/0073241 | A1 | 3/2015 | Lamego |
| 2015/0080754 | A1 | 3/2015 | Purdon et al. |
| 2015/0099950 | A1 | 4/2015 | Al-Ali et al. |
| 2017/0024748 | A1 | 1/2017 | Haider |
| 2017/0251974 | A1 | 9/2017 | Shreim et al. |
| 2018/0247712 | A1 | 8/2018 | Muhsin et al. |
| 2020/0111552 | A1 | 4/2020 | Ahmed |
| 2020/0113520 | A1 | 4/2020 | Abdul-Hafiz et al. |
| 2020/0138368 | A1 | 5/2020 | Kiani et al. |
| 2020/0253474 | A1 | 8/2020 | Muhsin et al. |
| 2020/0253544 | A1 | 8/2020 | Belur Nagaraj et al. |
| 2020/0275841 | A1 | 9/2020 | Telfort et al. |
| 2020/0288983 | A1 | 9/2020 | Telfort et al. |
| 2020/0329993 | A1 | 10/2020 | Al-Ali et al. |
| 2021/0022628 | A1 | 1/2021 | Telfort et al. |
| 2021/0104173 | A1 | 4/2021 | Pauley et al. |
| 2021/0117525 | A1 | 4/2021 | Kiani et al. |
| 2021/0161465 | A1 | 6/2021 | Barker et al. |
| 2021/0236729 | A1 | 8/2021 | Kiani et al. |
| 2021/0275101 | A1 | 9/2021 | Vo et al. |
| 2021/0290080 | A1 | 9/2021 | Ahmed |
| 2021/0290120 | A1 | 9/2021 | Al-Ali |
| 2021/0290177 | A1 | 9/2021 | Novak, Jr. |
| 2021/0290184 | A1 | 9/2021 | Ahmed |
| 2021/0296008 | A1 | 9/2021 | Novak, Jr. |
| 2021/0330228 | A1 | 10/2021 | Olsen et al. |
| 2021/0386382 | A1 | 12/2021 | Olsen et al. |
| 2021/0402110 | A1 | 12/2021 | Pauley et al. |
| 2022/0039707 | A1 | 2/2022 | Sharma et al. |
| 2022/0071562 | A1 | 3/2022 | Kiani |
| 2022/0096603 | A1 | 3/2022 | Kiani et al. |
| 2022/0151521 | A1 | 5/2022 | Krishnamani et al. |
| 2022/0218244 | A1 | 7/2022 | Kiani et al. |
| 2022/0287574 | A1 | 9/2022 | Telfort et al. |
| 2022/0296161 | A1 | 9/2022 | Al-Ali et al. |
| 2022/0361819 | A1 | 11/2022 | Al-Ali et al. |
| 2022/0379059 | A1 | 12/2022 | Yu et al. |
| 2022/0392610 | A1 | 12/2022 | Kiani et al. |
| 2023/0028745 | A1 | 1/2023 | Al-Ali |
| 2023/0038389 | A1 | 2/2023 | Vo |
| 2023/0045647 | A1 | 2/2023 | Vo |
| 2023/0058052 | A1 | 2/2023 | Al-Ali |
| 2023/0058342 | A1 | 2/2023 | Kiani |
| 2023/0069789 | A1 | 3/2023 | Koo et al. |
| 2023/0087671 | A1 | 3/2023 | Telfort et al. |
| 2023/0110152 | A1 | 4/2023 | Forrest et al. |
| 2023/0111198 | A1 | 4/2023 | Yu et al. |
| 2023/0115397 | A1 | 4/2023 | Vo et al. |
| 2023/0116371 | A1 | 4/2023 | Mills et al. |
| 2023/0135297 | A1 | 5/2023 | Kiani et al. |
| 2023/0138098 | A1 | 5/2023 | Telfort et al. |
| 2023/0145155 | A1 | 5/2023 | Krishnamani et al. |
| 2023/0147750 | A1 | 5/2023 | Barker et al. |
| 2023/0210417 | A1 | 7/2023 | Al-Ali et al. |
| 2023/0222805 | A1 | 7/2023 | Muhsin et al. |
| 2023/0222887 | A1 | 7/2023 | Muhsin et al. |
| 2023/0226331 | A1 | 7/2023 | Kiani et al. |
| 2023/0284916 | A1 | 9/2023 | Telfort |
| 2023/0284943 | A1 | 9/2023 | Scruggs et al. |
| 2023/0301562 | A1 | 9/2023 | Scruggs et al. |
| 2023/0346993 | A1 | 11/2023 | Kiani et al. |
| 2023/0368221 | A1 | 11/2023 | Haider |
| 2023/0371893 | A1 | 11/2023 | Al-Ali et al. |
| 2023/0389837 | A1 | 12/2023 | Krishnamani et al. |
| 2024/0016418 | A1 | 1/2024 | Devadoss et al. |
| 2024/0016419 | A1 | 1/2024 | Devadoss et al. |
| 2024/0047061 | A1 | 2/2024 | Al-Ali et al. |
| 2024/0049310 | A1 | 2/2024 | Al-Ali et al. |
| 2024/0049986 | A1 | 2/2024 | Al-Ali et al. |
| 2024/0081656 | A1 | 3/2024 | DeJong et al. |
| 2024/0122486 | A1 | 4/2024 | Kiani |
| 2024/0180456 | A1 | 6/2024 | Al-Ali |

FOREIGN PATENT DOCUMENTS

| | | |
|---|---|---|
| EP | 1 849 491 | 10/2007 |
| WO | WO 2020/109115 | 6/2020 |

OTHER PUBLICATIONS

"Breathing Problems", Stanford Children's Health, as archived Mar. 24, 2022, https://web.archive.org/web/20220324055525/https://www.stanfordchildrens.org/en/topic/default?id=breathing-problems-90-P02666, pp. 2.
"Flow Measurement with Respironics Flow Sensors", Respironics, Inc., White Paper, Apr. 2011, pp. 7.
Masimo, "NomoLine® Cannulas and Airway Adapter Sets", as archived Jan. 23, 2021, https://web.archive.org/web/20210123014631/https://www.masimo.com/products/ventillator/capnography/nomoline/airway-adapters/, pp. 12.
Patient Monitoring Catalog, "Capnography—Microstream® $EtCO_2$", 2016, pp. 6-17.
Yuan et al., "Respiratory Rate and Breathing Pattern", MUMJ, Clinical Review, vol. 10, No. 1, 2013, pp. 23-25.

* cited by examiner

LOW DEADSPACE AIRWAY ADAPTER

INCORPORATION BY REFERENCE TO ANY PRIORITY APPLICATIONS

The present application claims priority to U.S. Provisional Application No. 63/220,134, filed Jul. 9, 2021, titled "Low Deadspace Airway Adapter", and U.S. Provisional Application No. 63/193,446, filed May 26, 2021, titled "Low Deadspace Airway Adapter", each of which is hereby incorporated by reference in its entirety. All of the above-listed applications and any and all other applications for which a foreign or domestic priority claim is identified in the Application Data Sheet as filed with the present application, are hereby incorporated by reference under 37 CFR 1.57.

TECHNICAL FIELD

The present disclosure relates to the field of airway adapters suitable for use in ventilation assemblies, and in particular, to airways adapters suitable to provide connection between, and sampling of gases flowing through, ventilation assemblies including endotracheal tubes and adapters connected thereto, flow sensors, and ventilation apparatuses and tubes or adapters connected thereto.

BACKGROUND

Patients undergoing medical treatment or a medical procedure may be provided with respiratory assistance with a ventilation apparatus and an endotracheal (ET) tube positioned within an internal airway of the patient. In some situations, an airway adapter is used to connect an ET tube (or a connector/adapter connected to an end thereof) with the ventilation apparatus (for example, a tube or connector of the ventilation apparatus). Some airway adapters include structure that allows for sampling of the patient's exhaled breath for analysis of the gaseous composition thereof, for example, carbon dioxide ($CO_2$) content. For example, some airway adapters include a port that can connect to a sampling line or tube that guides a portion of the patient's exhaled breath to a monitoring system. In some situations, a flow sensor is incorporated into the ventilation assembly in order to monitor the flow rate of gas traveling into or out of the patient and through the ventilation assembly.

SUMMARY

Current airway adapters used in ventilation assemblies with ET tubes, flow sensors, and ventilation apparatuses have various limitations and disadvantages. For example, it is often difficult to minimize the amount of internal void volume (also referred to herein as "internal volume") included in or introduced by an airway adapter in a ventilation assembly. Existing airway adapters used to connect an ET tube (and/or adapters connected thereto), a ventilation apparatus (and/or connectors or adapters connected thereto), and, in some cases, a flow sensor, typically provide connection compatibility at the expense of introducing larger than desirable internal void volumes within the airway adapters and/or in the breathing circuit defined by the connected components of the ventilation assembly. Reduction of internal void volumes (commonly referred to as "dead space") present in the airway adapter and ventilation assembly, prior to and during connection with other components of the ventilation assembly, may be important in order to ensure quick and thorough exchange of gas flow through the airway adapter and assembly (for example, avoiding negative effects of gas mixing) and to protect the integrity of gas sampling measurements where the airway adapter includes a sampling port. Various implementations of the airway adapters disclosed herein provide significantly low internal void volumes alone and when coupled with other components of a ventilation assembly while also ensuring compatibility and operability of such components.

Disclosed herein is a low dead space airway adapter for sampling fluid flowing through a ventilation assembly, the airway adapter comprising: a first outer wall configured to couple to an endotracheal (ET) tube adapter, the first outer wall defining a first internal cavity; a second outer wall configured to couple to a flow sensor or a ventilation tube connector, the second outer wall defining a second internal cavity; a barrier wall positioned between the first and second internal cavities of the first and second outer walls, the barrier wall comprising a barrier wall opening; a first internal projection positioned within the first internal cavity defined by the first outer wall and spaced from an interior surface of the first outer wall, the first internal projection extending outward from the barrier wall and extending around an entirety of said barrier wall opening, the first internal projection extending beyond a free end of the first outer wall and configured to extend into an internal cavity of the ET tube adapter when the first outer wall is coupled to the ET tube adapter; a second internal projection positioned within the second internal cavity defined by the second outer wall and spaced from an interior surface of the second outer wall, the second internal projection extending outward from the barrier wall in an opposite direction as the first internal projection and extending around the entirety of said barrier wall opening; and a sampling portion. In some implementations, the first internal projection comprises: a first end connected to the barrier wall; a second end opposite the first end; a first fluid passageway extending between the first and second ends; and an opening at the second end, wherein the opening of the first internal projection is in fluid communication with the first fluid passageway and the barrier wall opening and wherein the second end of the first internal projection comprises a curved chamfer that extends around an entirety of the opening of the first internal projection. In some implementations, the second internal projection comprises: a first end connected to the barrier wall; a second end opposite the first end of the second internal projection, wherein the second end of the second internal projection is spaced inward from a free end of the second outer wall within the second internal cavity defined by the second outer wall; and a second fluid passageway extending between the first and second ends of the second internal projection, the second fluid passageway in fluid communication with the barrier wall opening and the first fluid passageway of the first internal projection. In some implementations, the sampling portion comprises at least one fluid passageway in fluid communication with the first fluid passageway, the barrier wall opening, and the second fluid passageway, the sampling portion configured to allow sampling of a portion of fluid flowing through at least one of the first and second fluid passageways when the airway adapter is in use.

In some implementations, the internal projection is neither compressible nor extendable. In some implementations, the opening at the second end of the first internal projection is circular. In some implementations, the second end of the first internal projection is chamfered at an angle relative to a plane extending along the second end of the first internal projection that is between approximately 40 degrees and approximately 50 degrees. In some implementations, the second internal projection comprises an internal cavity defining said second fluid passageway, said internal cavity of the second internal projection having a first portion and a second portion, the first portion positioned closer to the barrier wall opening than the second portion, the first portion having a cross-sectional area that is smaller than a cross-sectional area of the second portion, the second portion configured to receive and secure to a portion of the flow sensor and facilitate fluid communication between the second fluid passageway and a fluid passageway of the flow sensor. In some implementations, the first portion of the internal cavity of the second internal projection extends along a greater portion of a length of the internal cavity of the second internal projection than the second portion of the internal cavity of the second internal projection. In some implementations, the first portion of the internal cavity of the second internal projection extends along a greater portion of a length of the internal cavity of the second internal projection than the second portion of the internal cavity of the second internal projection.

Disclosed herein is a low dead space airway adapter for sampling fluid flowing through a ventilation assembly, the airway adapter comprising: a first outer wall configured to couple to an endotracheal (ET) tube adapter, the first outer wall defining a first internal cavity; a second outer wall configured to couple to a flow sensor or a ventilation tube connector, the second outer wall defining a second internal cavity; a barrier wall positioned between the first and second internal cavities of the first and second outer walls, the barrier wall comprising a barrier wall opening; an internal projection positioned within the first internal cavity defined by the first outer wall and spaced from an interior surface of the first outer wall, the internal projection extending outward from the barrier wall and extending around an entirety of said barrier wall opening, the internal projection extending beyond a free end of the first outer wall and configured to extend into an internal cavity of the ET tube adapter when the first outer wall is coupled to the ET tube adapter; and a sampling portion. In some implementations, the internal projection comprises: a first end connected to the barrier wall; a second end opposite the first end; a first fluid passageway extending between the first and second ends; and an opening at the second end, wherein the opening of the internal projection is in fluid communication with the first fluid passageway and the barrier wall opening and wherein the second end of the internal projection is chamfered around an entirety of the opening of the internal projection. In some implementations, the sampling portion comprises at least one fluid passageway in fluid communication with the first fluid passageway and the barrier wall opening, the sampling portion configured to allow sampling of a portion of fluid flowing through the first fluid passageway when the airway adapter is in use.

In some implementations, the internal projection is neither compressible nor extendable. In some implementations, the second end of the internal projection is chamfered at an angle relative to a plane extending along the second end of the internal projection that is between approximately 40 degrees and approximately 50 degrees. In some implementations, said internal projection is a first internal projection of the airway adapter and wherein the airway adapter further comprises a second internal projection positioned within the second internal cavity defined by the second outer wall and spaced from an interior surface of the second outer wall, the second internal projection extending outward from the barrier wall in an opposite direction as the first internal projection and extending around the entirety of said barrier wall opening, the second internal projection comprising: a first end connected to the barrier wall; a second end opposite the first end of the second internal projection; and a second fluid passageway extending between the first and second ends of the second internal projection, the second fluid passageway in fluid communication with the barrier wall opening and the first fluid passageway of the first internal projection. In some implementations, the second end of the second internal projection is spaced inward from a free end of the second outer wall and has a length that is smaller than the first internal projection.

Disclosed herein is a low dead space airway adapter for sampling fluid flowing through a ventilation assembly, the airway adapter comprising: a first outer wall configured to couple to an endotracheal (ET) tube adapter, the first outer wall defining a first internal cavity; a second outer wall configured to couple to a flow sensor or a ventilation tube connector, the second outer wall defining a second internal cavity; a barrier wall positioned between the first and second internal cavities of the first and second outer walls, the barrier wall comprising a barrier wall opening; and an internal projection positioned within the first internal cavity defined by the first outer wall, the internal projection extending outward from the barrier wall and extending at least partially around said barrier wall opening, the internal projection configured to extend into an internal cavity of the ET tube adapter when the first outer wall is coupled to the ET tube adapter. In some implementations, the internal projection comprises: a first end connected to the barrier wall; a second end opposite the first end; a first fluid passageway extending between the first and second ends; and an opening at the second end, wherein the opening of the internal projection is in fluid communication with the first fluid passageway and the barrier wall opening and wherein the second end of the internal projection is at least partially chamfered around the opening of the internal projection.

In some implementations, the low dead space airway adapter further comprises a sampling portion comprising at least one fluid passageway in fluid communication with the first fluid passageway and the barrier wall opening, the sampling portion configured to allow sampling of a portion of fluid flowing through the first fluid passageway when the airway adapter is in use. In some implementations, the internal projection is neither compressible nor extendable. In some implementations, the opening at the second end of the internal projection is circular. In some implementations, the internal projection extends beyond a free end of the first outer wall. In some implementations, said internal projection is a first internal projection of the airway adapter and wherein the airway adapter further comprises a second internal projection positioned within the second internal cavity defined by the second outer wall, the second internal projection extending outward from the barrier wall in an opposite direction as the first internal projection and extending at least partially around said barrier wall opening, the second internal projection comprising: a first end connected to the barrier wall; a second end opposite the first end of the second internal projection; and a second fluid passageway extending between the first and second ends of the second internal projection, the second fluid passageway in fluid communication with the barrier wall opening and the first fluid passageway of the first internal projection. In some implementations: the second end of the second internal projection is spaced inward from a free end of the second outer wall within the second internal cavity defined by the second outer wall; a first plane extending along the second end of the second internal projection partitions the second internal cavity into a first portion and a second portion, the second portion being positioned between said first plane and a second plane extending along the free end of the second outer wall; and a total interior volume of the first fluid passageway, the second fluid passageway, and the second portion of the second internal cavity is less than approximately 2.5 ml. In some implementations, the second internal projection comprises an internal cavity defining said second fluid passageway, said internal cavity of the second internal projection having a first portion and a second portion, the first portion positioned closer to the barrier wall opening than the second portion, the first portion having a cross-sectional area that is smaller than a cross-sectional area of the second portion, the second portion configured to receive and secure to a portion of the flow sensor and facilitate fluid communication between the second fluid passageway and a fluid passageway of the flow sensor.

Disclosed herein is a low dead space airway adapter for sampling fluid flowing through a ventilation assembly, the airway adapter including: a first outer wall configured to couple to an endotracheal (ET) tube adapter, the first outer wall defining a first internal cavity; a second outer wall configured to couple to a flow sensor or a ventilation tube connector, the second outer wall defining a second internal cavity; a barrier wall separating the first and second internal cavities from one another, the barrier wall comprising a barrier wall opening; a first internal projection; and a sampling portion. The first internal projection can extend outward from the barrier wall around said barrier wall opening. The first internal projection can be configured to extend into an internal cavity of the ET tube adapter when the first outer wall is coupled to the ET tube adapter. The first internal projection can comprise: a first end connected to the barrier wall; a second end opposite the first end; a first fluid passageway extending between the first and second ends; and an opening at the second end, wherein the opening is in fluid communication with the first fluid passageway and the barrier wall opening and wherein at least a portion of the second end is chamfered around the opening. The sampling portion can comprise at least one fluid passageway in fluid communication with the first fluid passageway of the first internal projection. The sampling portion can be configured to allow sampling of a portion of fluid flowing through the first fluid passageway of the first internal projection when the airway adapter is in use.

In some configurations, an entire perimeter of the second end of the first internal projection around the opening is chamfered. In some configurations, the chamfered at least the portion of the second end of the first internal projection comprises a curved chamfer. In some configurations, an entire perimeter of the second end of the first internal projection around the opening comprises said curved chamfer. In some configurations, the opening at the second end of the first internal projection is circular. In some configurations, the first internal projection comprises a cylindrical shape. In some configurations, the at least the portion of the second end is chamfered at an angle of between approximately 40 degrees and approximately 50 degrees. In some configurations, the sampling portion comprises a first port extending outward from an outer surface of the first outer wall, a second port extending at least partially within the barrier wall opening, each of the first and second ports comprising a fluid passageway in fluid communication with one another and with the first fluid passageway of the first internal projection. In some configurations, the sampling portion further comprises a channel extending at least through a portion of the barrier wall between the fluid passageways of the first and second ports, the channel comprising a fluid passageway in fluid communication with the fluid passageways of the first and second ports. In some configurations, the opening at the second end of the first internal projection is circular and comprises a diameter, and wherein a free end of the second port extends to a longitudinal axis extending through a center of the circular opening. In some configurations, the second port comprises a length that is less than a height of the opening of the first internal projection and a width that is less than a width of the opening of the first internal projection. In some configurations, a ratio of the width of the opening of the first internal projection to the width of the second port is between approximately 2 and approximately 5. In some configurations, a ratio of the height of the opening of the first internal projection to the length of the second port is approximately 2. In some configurations, the opening of the first internal projection is circular and wherein a ratio of a diameter of the opening of the first internal projection to the width of the second port is between approximately 2.5 and approximately 4. In some configurations, a ratio of the height of the opening of the first internal projection to the length of the second port is between approximately 1 and approximately 3. In some configurations, the low dead space airway adapter further comprises a second internal projection surrounding the opening of the barrier wall and extending outward from the barrier wall in an opposite direction as the first internal projection, wherein the second internal projection comprises a second fluid passageway in fluid communication with the barrier wall opening, the first fluid passageway of the first internal projection, and the at least one fluid passageway of the sampling portion. In some configurations, the second internal projection further comprises an internal cavity having a first portion and a second portion, the first portion of the internal cavity having a cross-sectional area that is smaller than a cross-sectional area of the second portion of the internal cavity, the second portion of the internal cavity configured to receive and secure to a portion of the flow sensor and facilitate fluid communication between the second fluid passageway and a fluid passageway of the flow sensor. In some configurations, the first and second portions of the internal cavity of the second internal projection are cylindrical, and the first portion of the internal cavity has a smaller inner diameter than the second portion of the internal cavity of the second internal projection. In some configurations, the first outer wall and the second outer wall are tubular. In some configurations, the first outer wall and the second outer wall are cylindrical. In some configurations, a total dead space of the airway adapter is less than approximately 2.5 ml. A ventilation assembly can include the airway adapter and can further include the ET tube and the flow sensor, wherein the second outer wall is configured to couple to the flow sensor. In some configurations, the first outer wall is configured to couple to the ET tube adapter via a friction fit. In some configurations, the second outer wall is configured to couple to the flow sensor in a friction fit.

Disclosed herein is a low dead space airway adapter including: a first outer wall configured to couple to an endotracheal (ET) tube adapter, the first outer wall defining a first internal cavity; and a first internal projection positioned at least partially within the first internal cavity and configured to extend within an internal cavity of the ET tube adapter when the first outer wall is coupled to the ET tube adapter. The first internal projection can comprise: a first fluid passageway configured for fluid communication with at least a portion of the internal cavity of the ET tube adapter when the first outer wall is coupled to the ET tube adapter;

and an end comprising an opening in fluid communication with the first fluid passageway, wherein at least a portion of the end is chamfered around the opening and configured to contact an inner surface of the ET tube adapter when the first outer wall is coupled to the ET tube adapter.

In some configurations, the end of the first internal projection is positioned outside the first internal cavity. In some configurations, an entire perimeter of the end of the first internal projection around the opening is chamfered. In some configurations, the chamfered at least the portion of the end of the first internal projection comprises a curved chamfer. In some configurations, an entire perimeter of the end of the first internal projection around the opening comprises said curved chamfer. In some configurations, the opening at the end of the first internal projection is circular. In some configurations, the at least the portion of the end is chamfered at an angle of between approximately 40 degrees and approximately 50 degrees. In some configurations, the airway adapter further comprises: a second outer wall configured to couple to a flow sensor or a ventilation tube connector, the second outer wall defining a second internal cavity; a barrier wall separating the first and second internal cavities from one another, the barrier wall comprising a barrier wall opening, wherein the first internal projection extends outward from the barrier wall around said barrier wall opening; and a sampling portion comprising at least one fluid passageway in fluid communication with the first fluid passageway of the first internal projection and the barrier wall opening, wherein the sampling portion is configured to allow sampling of a portion of fluid flowing through the first fluid passageway of the first internal projection when the airway adapter is in use. In some configurations, the airway adapter further comprises: a second internal projection surrounding the opening of the barrier wall and extending outward from the barrier wall in an opposite direction as the first internal projection, wherein the second internal projection comprises a second fluid passageway in fluid communication with the barrier wall opening, the first fluid passageway of the first internal projection, and the at least one fluid passageway of the sampling portion. A ventilation assembly can include the airway adapter and can further include the ET tube and the flow sensor, wherein the second outer wall is configured to couple to the flow sensor.

Disclosed herein is a low dead space airway adapter for sampling fluid flowing through a ventilation assembly, the airway adapter including: a first portion configured to couple to an endotracheal (ET) tube adapter; a second portion configured to couple to a flow sensor or a ventilation tube connector; and a sampling portion. The first portion can comprise: a first outer wall defining a first internal cavity; and a first internal projection positioned within the first internal cavity and spaced from the first outer wall, the first internal projection comprising a first fluid passageway and a free end positioned outside the first internal cavity, the free end comprising an opening into the first fluid passageway, wherein at least a portion of the free end is chamfered around the opening, the chamfered at least the portion of the free end configured to contact an inner surface of the ET tube adapter when the first portion is coupled to the ET tube adapter. The second portion can be in fluid communication with the first fluid passageway of the first internal projection. The sampling portion can comprise at least one fluid passageway in fluid communication with the first fluid passageway of the first internal projection, wherein the sampling portion is configured to allow sampling of a portion of fluid flowing through the first fluid passageway of the first internal projection when the airway adapter is in use.

In some configurations, an entire perimeter of the free end of the first internal projection around the opening is chamfered. In some configurations, the chamfered at least the portion of the free end of the first internal projection comprises a curved chamfer. In some configurations, an entire perimeter of the free end of the first internal projection around the opening comprises said curved chamfer. In some configurations, the opening at the second end of the first internal projection is circular. In some configurations, said second portion comprises: a second outer wall configured to couple to the flow sensor or the ventilation tube connector, the second outer wall defining a second internal cavity; a second internal projection positioned within the second outer wall, the second internal projection comprising a second fluid passageway in fluid communication with the first fluid passageway, wherein a free end of the second internal projection is spaced inward from a free end of the second outer wall. Said sampling portion can comprise at least one fluid passageway in fluid communication with the first and second fluid passageways. In some configurations: a first plane of the free end of the second internal projection partitions the second internal cavity into a first portion and a second portion, the second portion of the second internal cavity being positioned between said first plane and a second plane of the free end of the second outer wall; and a total interior volume of the first fluid passageway, second fluid passageway, and the second portion of the internal cavity is less than approximately 2.5 ml. A ventilation assembly can include the airway adapter and can further include the ET tube adapter.

Disclosed herein is a low dead space airway adapter for sampling fluid flowing through a ventilation assembly, the airway adapter including: a first outer wall configured to couple to an endotracheal (ET) tube adapter; a second outer wall configured to couple to a flow sensor or a ventilation tube connector, the second outer wall defining an internal cavity; a first internal projection positioned at least partially within the first outer wall and configured to be positioned within an internal cavity of the ET tube adapter when the first outer wall is coupled to the ET tube adapter, the first internal projection comprising a first fluid passageway; a second internal projection positioned within the second outer wall, the second internal projection comprising a second fluid passageway in fluid communication with the first fluid passageway, wherein a free end of the second internal projection is spaced inward from a free end of the second outer wall within the internal cavity defined by the second outer wall, a first plane of the free end of the second internal projection partitioning the internal cavity into a first portion and a second portion, the second portion being positioned between said first plane and a second plane of the free end of the second outer wall; and a sampling portion comprising at least one fluid passageway in fluid communication with the first and second fluid passageways, wherein the sampling portion is configured to allow sampling of a portion of fluid flowing through at least one of the first and second fluid passageways when the airway adapter is in use; wherein a total interior volume of the first fluid passageway, second fluid passageway, and the second portion of the internal cavity is less than approximately 2.5 ml.

In some configurations, the first internal projection is spaced from the first outer wall. In some configurations, the airway adapter further comprises: a barrier wall configured to separate the internal cavity defined by the second outer wall from an internal cavity defined by the first outer wall, the barrier wall comprising a barrier wall opening, wherein the first internal projection extends outward from the barrier wall around said barrier wall opening and wherein the second internal projection extends outward from the barrier wall around said barrier wall opening in an opposite direction as the first internal projection. In some configurations, the first internal projection further comprises: a first end connected to the barrier wall; a second end opposite the first end; and an opening at the second end, wherein the opening is in fluid communication with the first fluid passageway and the barrier wall opening and wherein at least a portion of the second end is chamfered around the opening. In some configurations, an entire perimeter of the second end of the first internal projection around the opening is chamfered. In some configurations, the chamfered at least the portion of the second end of the first internal projection comprises a curved chamfer. In some configurations, an entire perimeter of the second end of the first internal projection around the opening comprises said curved chamfer. In some configurations, the opening at the second end of the first internal projection is circular. In some configurations, the total interior volume of the first fluid passageway, second fluid passageway, and the second portion of the internal cavity is less than approximately 2 ml. In some configurations, the first outer wall and the second outer wall are tubular. In some configurations, the first outer wall and the second outer wall are cylindrical. A ventilation assembly can include the airway adapter and can further include the ET tube and the flow sensor, wherein the second outer wall is configured to couple to the flow sensor.

Disclosed herein is a low dead space airway adapter for sampling fluid flowing through a ventilation assembly, the airway adapter including: a first portion configured to couple to an endotracheal (ET) tube adapter; a second portion configured to couple to a flow sensor or a ventilation tube connector; and a sampling portion configured to allow sampling of fluid flowing through at least a portion of the first and second portions of the airway adapter when in use; wherein, when the first portion of the airway adapter is coupled to the ET tube adapter, a total dead space of the airway adapter and the ET tube adapter is less than approximately 1.7 ml.

In some configurations, said first portion comprises: a first outer wall defining a first internal cavity, the first outer wall configured to couple to the ET tube adapter; and a first internal projection positioned at least partially within the first internal cavity and configured to be positioned within an internal cavity of the ET tube adapter when the first outer wall is coupled to the ET tube adapter, the first internal projection comprising a first fluid passageway. In some configurations, the first internal projection further comprises a free end positioned outside the first internal cavity and an opening into the first fluid passageway at the free end, wherein at least a portion of the free end is chamfered around the opening, the chamfered at least the portion of the free end configured to contact an inner surface of the ET tube adapter when the first outer wall is coupled to the ET tube adapter. In some configurations, an entire perimeter of the free end of the first internal projection around the opening is chamfered. In some configurations, the chamfered at least the portion of the free end of the first internal projection comprises a curved chamfer. In some configurations, an entire perimeter of the free end of the first internal projection around the opening comprises said curved chamfer. In some configurations, the opening at the second end of the first internal projection is circular. In some configurations, the at least the portion of the free end is chamfered at an angle of between approximately 40 degrees and approximately 50 degrees. In some configurations, said second portion comprises: a second outer wall configured to couple to the flow sensor or the ventilation tube connector, the second outer wall defining a second internal cavity; a second internal projection positioned within the second outer wall, the second internal projection comprising a second fluid passageway in fluid communication with the first fluid passageway, wherein a free end of the second internal projection is spaced inward from a free end of the second outer wall within the second internal cavity. In some configurations, said sampling portion comprises at least one fluid passageway in fluid communication with the first and second fluid passageways. In some configurations: a first plane of the free end of the second internal projection partitions the second internal cavity into a first portion and a second portion, the second portion being positioned between said first plane and a second plane of the free end of the second outer wall; and a total interior volume of the first fluid passageway, second fluid passageway, and the second portion of the internal cavity is less than approximately 2.5 ml. In some configurations, the total interior volume of the first fluid passageway, second fluid passageway, and the second portion of the internal cavity is less than approximately 2 ml.

Disclosed herein is a low dead space airway adapter for sampling fluid flowing through a ventilation assembly, the airway adapter including: a first portion configured to couple to an endotracheal (ET) tube adapter; a second portion configured to couple to a flow sensor or a ventilation tube connector; and a sampling portion configured to allow sampling of fluid flowing through at least a portion of the first and second portions of the airway adapter when in use; wherein, when the first portion of the airway adapter is coupled to the ET tube adapter, a total dead space of the airway adapter and the ET tube adapter is less than 50% more than a dead space of the ET tube adapter.

For purposes of summarizing the disclosure, certain aspects, advantages and novel features of several devices, systems, and methods have been described herein. It is to be understood that not necessarily all examples of the present disclosure are disclosed herein. Thus, the devices, systems, and methods disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Certain features of this disclosure are described below with reference to the drawings. The illustrated embodiments are intended to illustrate, but not to limit the embodiments. Various features of the different disclosed embodiments can be combined to form further embodiments, which are part of this disclosure.

FIG. 3O illustrates an enlarged view of a portion of the cross-section of the airway adapter shown in FIG. 3L in accordance with aspects of this disclosure.

DETAILED DESCRIPTION

Various embodiments will be described below in conjunction with the drawings for purposes of illustration. It should be appreciated that many other implementations of the disclosed concepts are possible, and various advantages can be achieved with the disclosed implementations.

Disclosed herein are airway adapters that can provide connectivity and, in some implementations, fluid sampling functionality, to ventilation assemblies and components thereof while also minimizing dead space in the assemblies. Certain embodiments of the airway adapters are described in the context of an ET tube (and/or connectors coupled thereto), a ventilation apparatus (and/or connectors and tubes coupled thereto), and a flow sensor, due to particular utility in that context. However, the airway adapters disclosed herein can also be applicable in other contexts and ventilation assemblies. Additionally, while certain embodiments of the airway adapters described herein include a sampling portion, which may include one or more ports, alternative embodiments of the airway adapters may not include a sampling portion. For example, some alternative embodiments of airway adapters do not include a sampling portion and are configured to provide connection and/or compatibility between various components of a ventilation assembly. No features, structure, or step disclosed herein is essential or indispensable.

Figure 1A:
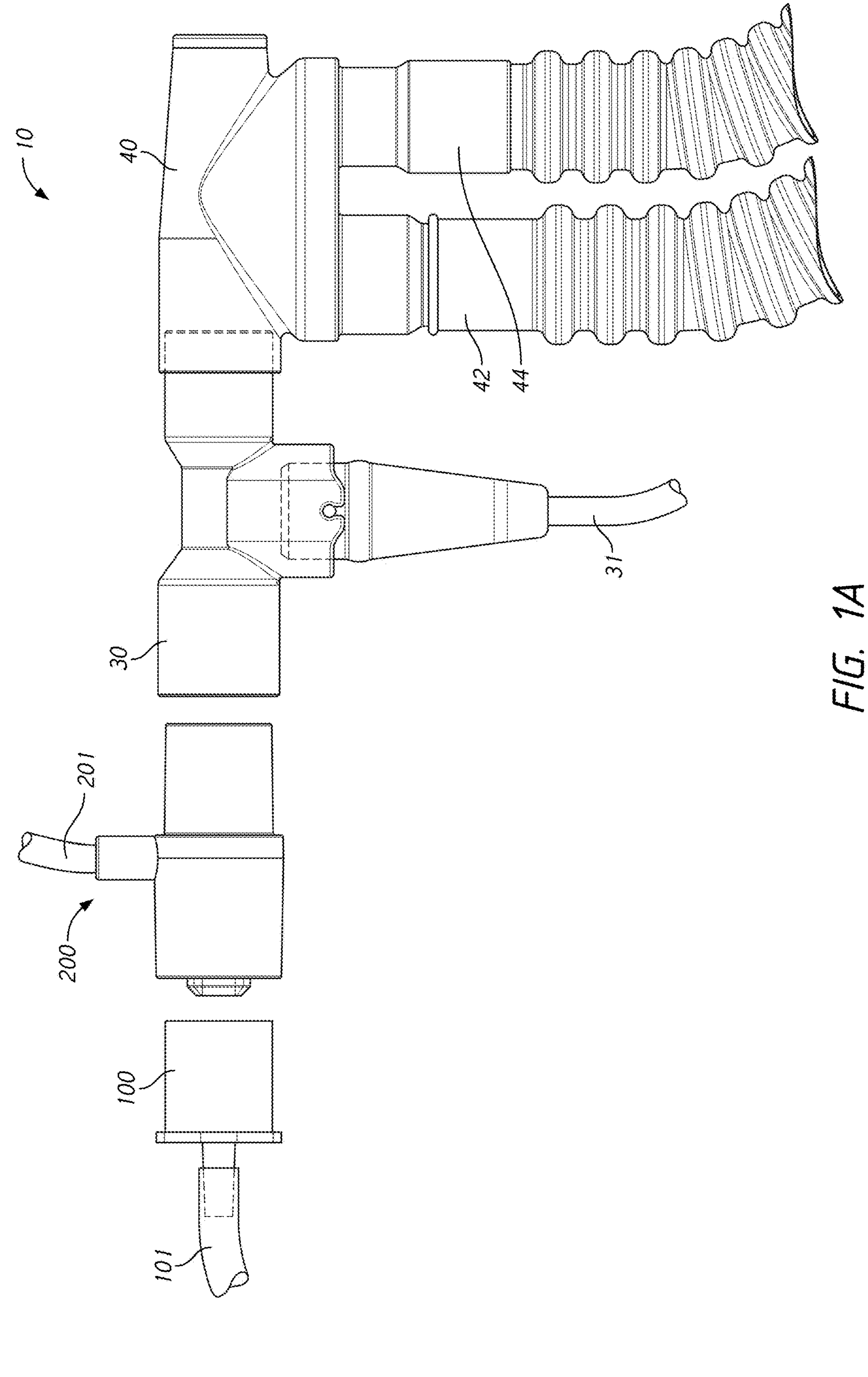
FIG. 1A illustrates an exploded view of a ventilation assembly in accordance with aspects of this disclosure.

FIG. 1A illustrates a ventilation assembly 10. As mentioned previously, ventilation assemblies, such as ventilation assembly 10, are often employed to provide respiratory assistance and/or to monitor aspects of a patient's breathing during a medical procedure or in other scenarios, such as during anesthesia or in connection with life support. In such cases, an endotracheal (ET) tube 101 is typically positioned within the patient's internal airway (for example, through the mouth and into the trachea). Such ET tubes 101 are often coupled to a connector or adapter 100 (which may also be referred to herein as "ET tube connector" or "ET tube adapter" or "ET tube fitting"). Such ET tubes 101 and ET tube adapters 100 are sometimes referred to collectively as an "ET tube." ET tube 101 and ET tube adapter 100 can be any of a variety of those available in the marketplace, such as that sold by VentiSeal™. As illustrated, ventilation assembly 10 can include ET tube 101, ET tube adapter 100, an airway adapter 200, a ventilation tube connector 40 (which may also be referred to herein as "ventilation tube adapter"), and, in some cases, a flow sensor 30. The ventilation tube connector 40 can be coupled with a ventilation apparatus (which can also be referred to as a "breathing apparatus") that can provide breathing gases to the patient. As shown, the ventilation tube connector 40 can be connected to one or more tubes, such as one or both of tubes 42, 44, that can connect the ventilation tube connector 40 with a ventilation apparatus. As discussed elsewhere herein, the airway adapter 200 can be configured to allow for a portion of the gas flowing through the airway adapter 200 and/or portions of the ventilation assembly 10 to be sampled, and in such cases, airway adapter 200 can be coupled with a sampling tube 201 that can deliver such sampled gas to a monitoring system.

Figure 1B:
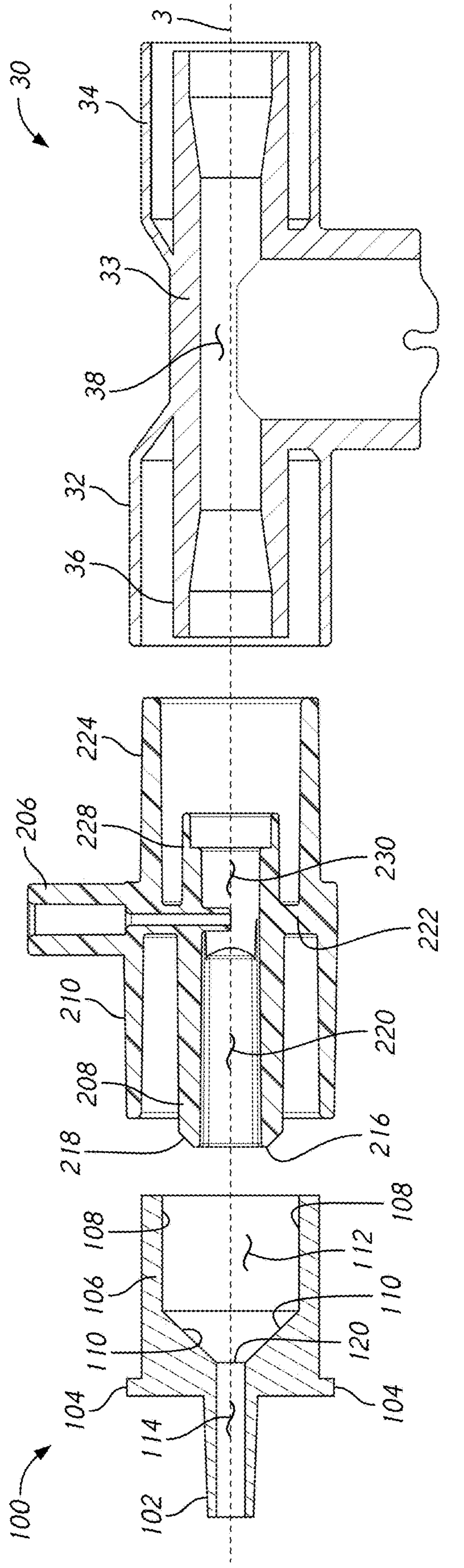
FIG. 1B illustrates a cross-sectional view of the ventilation assembly shown in FIG. 1A in accordance with aspects of this disclosure.

As mentioned previously, it is desirable in some cases to include a flow sensor in a ventilation assembly in order to measure flow rate of gases flowing into and/or out of the patient's airway and/or the ventilation assembly (or portions thereof). FIG. 1A illustrates an exemplary flow sensor 30 that can be utilized in the ventilation assembly 10. Flow sensor 30 can be coupled with a cable 31 that can supply power to the flow sensor 30 in order to allow the flow sensor 30 to perform flow rate sensing functionality. In some cases, the cable 31 can transmit data (for example, data related to flow rate) to a separate device, such as a monitoring device. Flow sensor 30 can be any of a variety of those available in the marketplace, such as that sold by Drager®. As shown, such flow sensor 30 can be connected to the ventilation tube connector 40. As also shown, the airway adapter 200 can connect and be positioned between the flow sensor 30 and the ET tube adapter 100. With reference to FIG. 1B, flow sensor 30 can include an outer wall 32 which can be tubular (for example, cylindrical), an outer wall 34 which can also be tubular (for example, cylindrical), and an intermediate portion 33 in between the outer walls 32, 34. Flow sensor 30 can include an internal projection 36 which can be tubular (for example, cylindrical), extending within and spaced from (for example, radially spaced from) the outer walls 32, 34 and which can define and/or form part of the intermediate portion 33. The internal projection 36 can define a fluid passageway 38, as shown, which can be in fluid communication with one or more fluid passageways of the airway adapter 200 discussed further below when the flow sensor 30 and the airway adapter 200 are coupled together. In some configurations of the ventilation assembly 10 which do not include flow sensor 30, the airway adapter 200 can connect and be positioned between the ET tube adapter 100 and the ventilation tube connector 40.

Figure 1C:
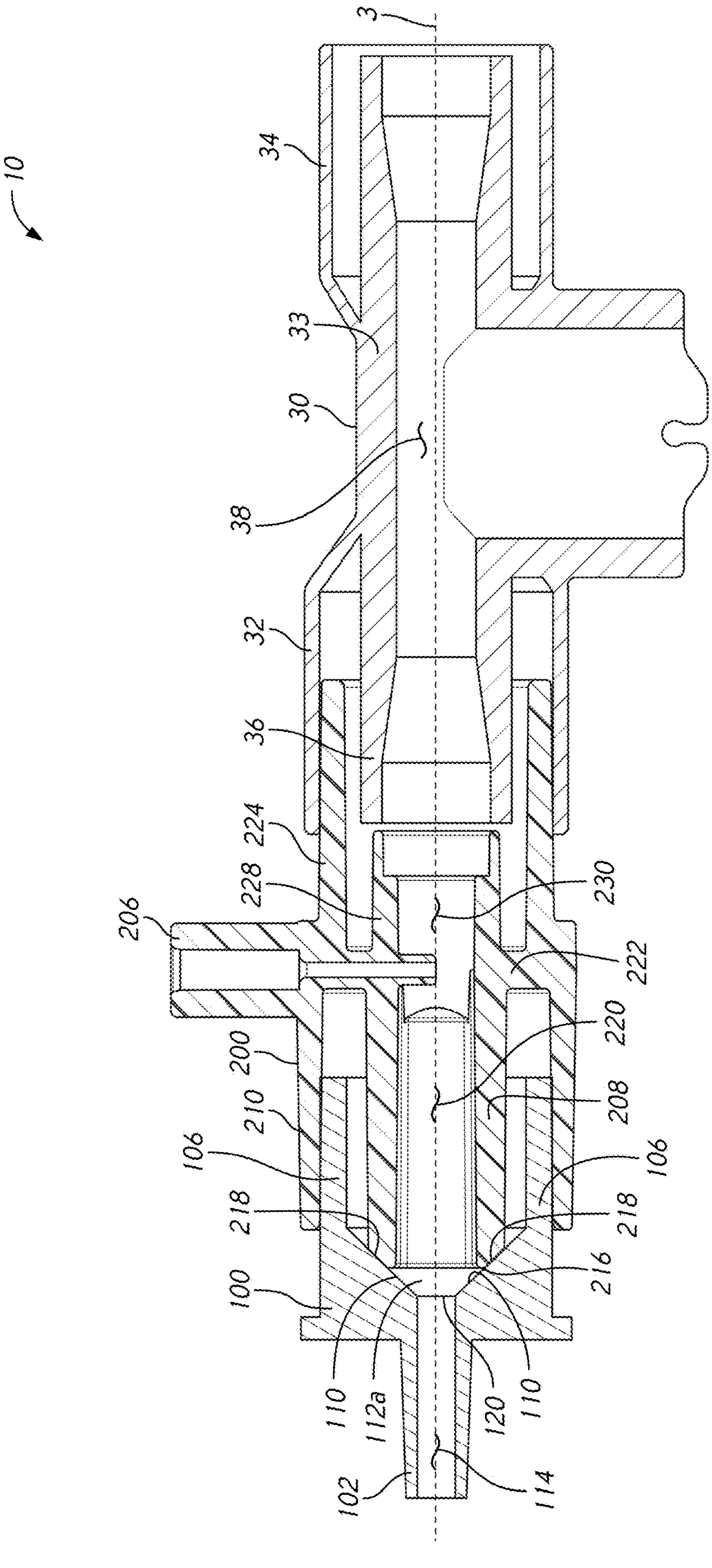
FIG. 1C illustrates another cross-sectional view of the ventilation assembly of FIG. 1A in an assembled form in accordance with aspects of this disclosure.

FIG. 1B illustrates a cross-sectional view taken through a portion of the ventilation assembly 10, illustrating the ET tube adapter 100, airway adapter 200, and the flow sensor 30 in an unassembled (for example, unconnected) configuration. FIG. 1C illustrates a cross-sectional view the ET tube adapter 100, airway adapter 200, and the flow sensor 30 in an assembled (for example, connected) configuration, for example, when the airway adapter 200 and/or the ventilation assembly 10 is in use. While FIGS. 1B-1C illustrate the ventilation assembly 10 without also illustrating the ET tube 101, sampling tube 201, cable 31, ventilation tube connector 40, and tubes 42, 44, this is merely intended to provide an enlarged view of the interaction and/or connection between the ET tube adapter 100, airway adapter 200, and the flow sensor 30, and is not intended to be limiting.

As illustrated in FIG. 1C, airway adapter 200 can connect, and provide fluid communication between, the ET tube adapter 100 and the flow sensor 30. However, in some configurations of the ventilation assembly 10 which do not include flow sensor 30, the airway adapter 200 can alternatively connect and provide fluid communication between the ET tube adapter 100 and the ventilation tube connector 40. As described in more detail below, the airway adapter 200 can include a sampling portion that allows a portion of fluid flowing through the airway adapter 200 (and/or portions of the ventilation assembly 10) to be sampled. Such sampling portion can allow monitoring of $CO_2$ content in patient exhalations as well as measurement of various constituents within such exhalations. Additionally or alternatively, such sampling portion can allow monitoring of aspects of fluid being provided by a ventilation apparatus coupled with the ventilation tube connector 40. As described in greater detail below, various aspects of the airway adapter 200 significantly minimize internal void volumes (also referred to herein as "dead space" and "internal volumes") within the ET tube connector 100, flow sensor 30, and airway adapter 200 itself when such components are coupled together.

Aspects of the ventilation assembly 10 illustrated in FIGS. 1B-1C and the interaction and connection of the airway adapter 200 with the ET tube adapter 100 and/or flow sensor 30 are described further below.

Figure 2A:
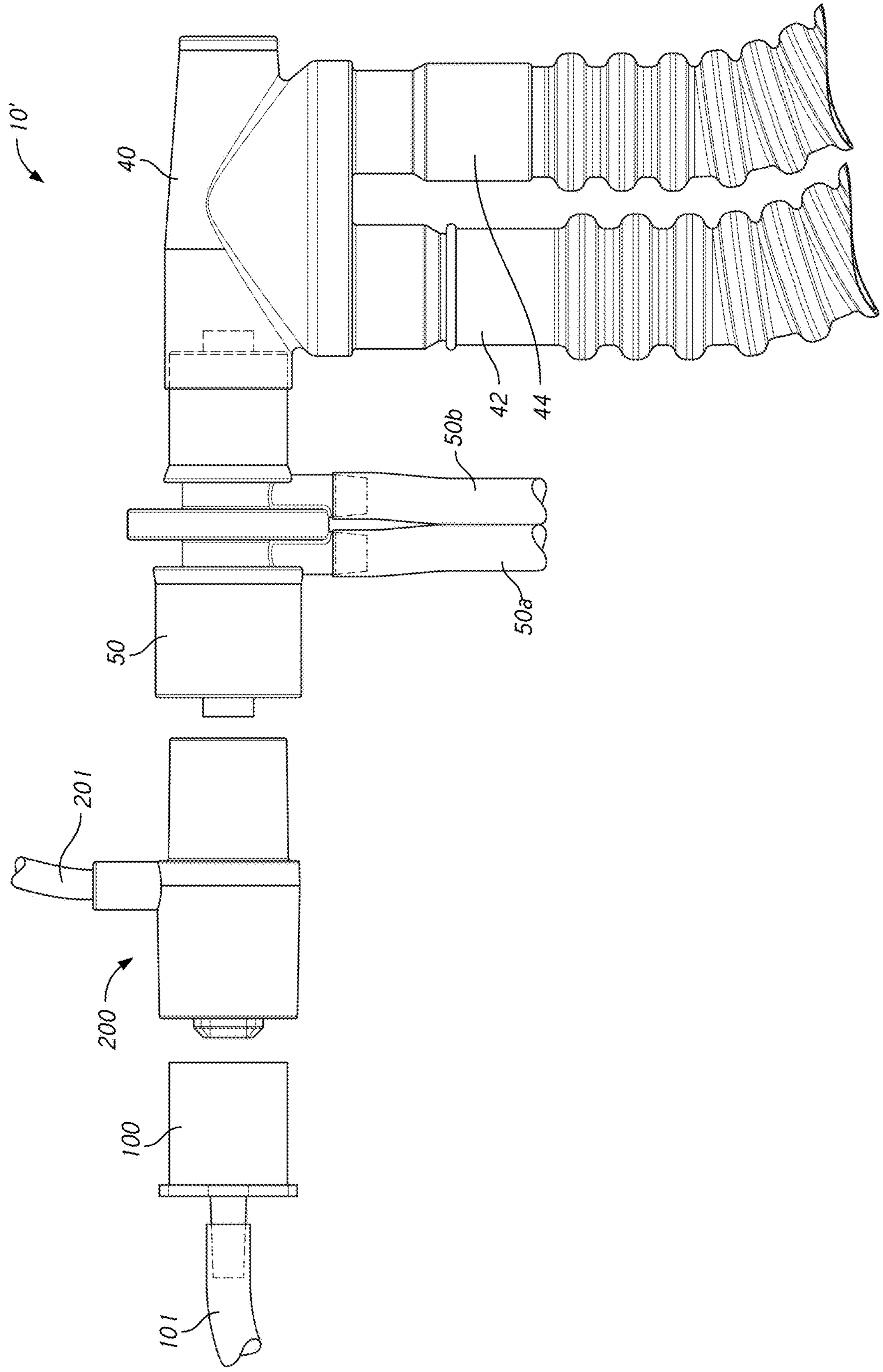
FIG. 2A illustrates an exploded view of a ventilation assembly in accordance with aspects of this disclosure.
Figure 2B:
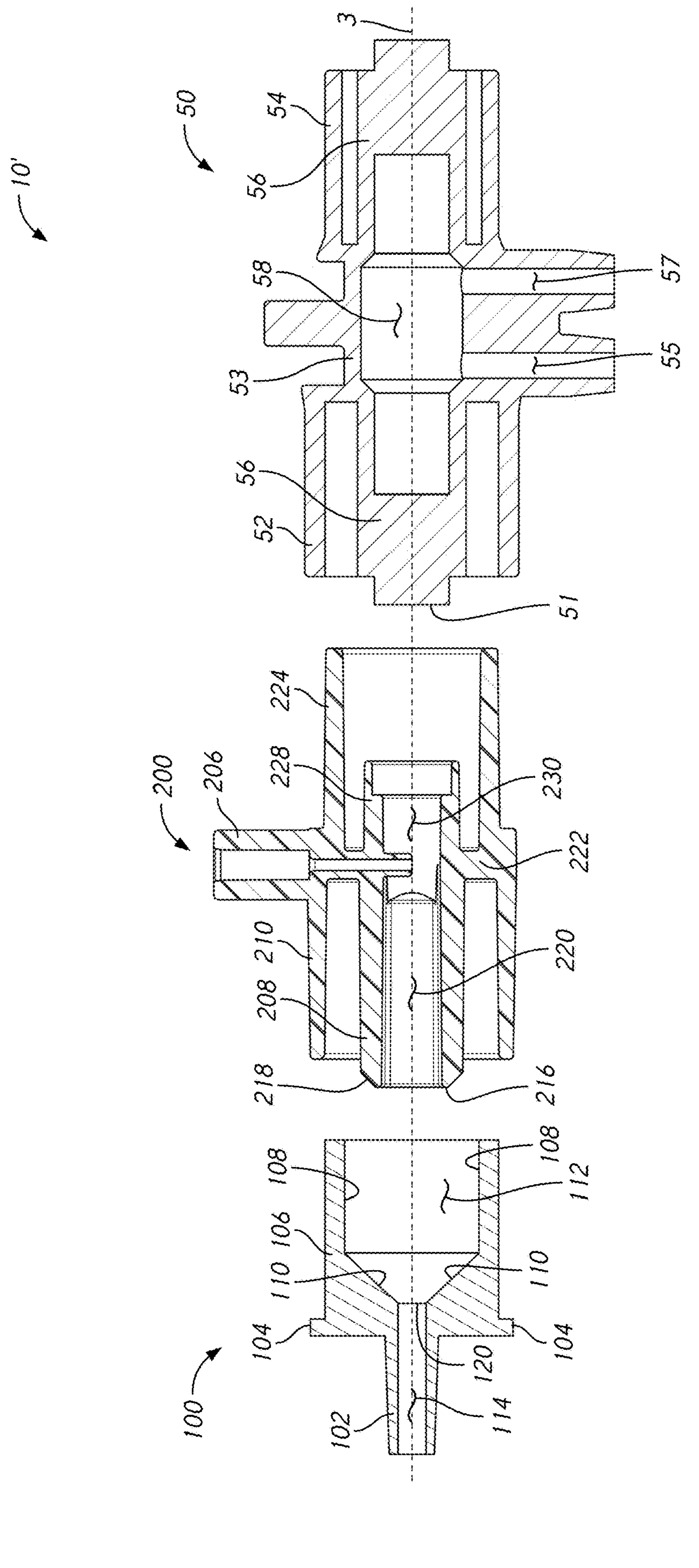
FIG. 2B illustrates a cross-sectional view of the ventilation assembly shown in FIG. 2A in accordance with aspects of this disclosure.
Figure 2C:
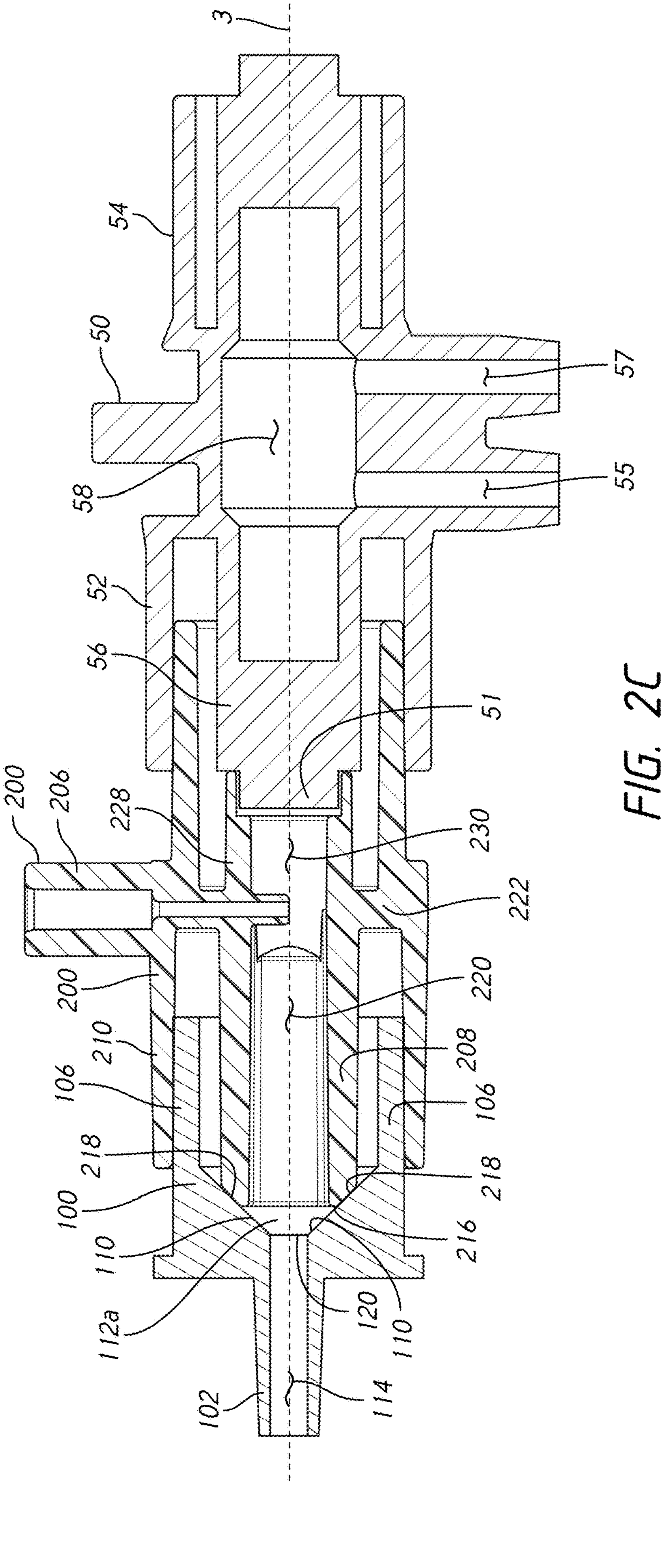
FIG. 2C illustrates another cross-sectional view of the ventilation assembly of FIG. 2A in an assembled form in accordance with aspects of this disclosure.

FIG. 2A illustrates another ventilation assembly 10' that is identical to ventilation assembly 10 except with respect to flow sensor 50, which is utilized instead of flow sensor 30. Flow sensor 50 illustrates another exemplary flow sensor that can be used in combination with airway adapter 200, ET tube 101, ET tube adapter 100, ventilation tube connector 40, tubes 42, 44, and a ventilation apparatus connected to tube(s) 42, 44. FIG. 2B illustrates a cross-sectional view taken through a portion of the ventilation assembly 10', illustrating the ET tube adapter 100, airway adapter 200, and the flow sensor 50 in an unassembled (for example, unconnected) configuration. FIG. 2C illustrates a cross-sectional view the ET tube adapter 100, airway adapter 200, and the flow sensor 50 in an assembled (for example, connected) configuration, for example, when the airway adapter 200 and/or the ventilation assembly 10' is in use. While FIGS. 2B-2C illustrate the ventilation assembly 10' without also illustrating the ET tube 101, sampling tube 201, tubes 50*a*, 50*b*, ventilation tube connector 40, and tubes 42, 44, this is merely intended to provide an enlarged view of the interaction and/or connection between the ET tube adapter 100, airway adapter 200, and the flow sensor 50, and is not intended to be limiting.

As illustrated in FIG. 2C, airway adapter 200 can connect, and provide fluid communication between, the ET tube adapter 100 and the flow sensor 50. However, in some configurations of the ventilation assembly 10' which do not include flow sensor 50, the airway adapter 200 can alternatively connect and provide fluid communication between the ET tube adapter 100 and the ventilation tube connector 40. As described in greater detail below, various aspects of the airway adapter 200 significantly minimize internal void volumes (also referred to herein as "dead space" and "internal volumes") within the ET tube connector 100, flow sensor 50, and airway adapter 200 itself when such components are coupled together.

Flow sensor 50, which can connect to airway adapter 200 as further described below, can be any of a variety of those available in the marketplace, such as one or more of those sold by Hamilton Medical®. Flow sensor 50 can connect to the ventilation tube connector 40, and the airway adapter 200 can connect and be positioned between the flow sensor 50 and the ET tube connector 100 when the airway adapter 200 is in use. With reference to FIG. 2B, flow sensor 50 can include an outer wall 52 which can be tubular (for example, cylindrical), an outer wall 54 which can also be tubular (for example, cylindrical), and an intermediate portion 53 in between the outer walls 52, 54. Flow sensor 50 can include internal projections 56 which can be tubular (for example, cylindrical), extending within and spaced from the outer walls 52, 54 and which can define and/or form part of the intermediate portion 53. As described in further detail below, the internal projection 56 can include a protrusion 51 extending outward from an end of the projection 56, and the airway adapter 200 can include structure to receive and/or secure to such protrusion 51. Flow sensor 50 can include a fluid passageway 58. Fluid passageway 58 can be defined by the intermediate portion 53 and projections 56. Flow sensor 50 can include fluid passageways 55 and/or 57 which allow fluid (or a portion thereof) flowing through the fluid passageway 58 to be guided to a separate flow rate measuring device via tube(s) 50*a*, 50*b* (see FIG. 2A). Fluid passageways 55, 57, and tubes 50*a*, 50*b* can facilitate differentiation pressure measurement which in some cases, may be utilized for flow rate analysis. In some cases, the protrusion 51 is cylindrical and/or includes an opening in fluid communication with the fluid passageway 58, 55, and/or 57. In some cases, protrusion 51 can be a wall that bifurcates flow through projection 56 of flow sensor 50 and/or splits an opening at an end (for example, the left end of flow sensor 50 given the view shown in FIG. 2C) into two portions that are each in fluid communication with the fluid passageway 58, 55, and/or 57.

Aspects of the ventilation assembly 10' illustrated in FIGS. 2B-2C and the interaction and connection of the airway adapter 200 with the ET tube adapter 100 and/or flow sensor 50 are described further below.

With reference to FIG. 1B or FIG. 2B, the ET tube connector 100 can include a protrusion 102, a rim 104, and/or an outer wall 106. The protrusion 102 can be sized to fit within ET tube 101 (see FIGS. 1A, 2A) and can include and/or define a fluid passageway 114 which can be in fluid communication with the ET tube 101 when the protrusion 102 and the ET tube 101 are coupled to one another. The outer wall 106 (or a portion thereof) can be tubular, for example, cylindrical, and can include and/or define an internal cavity 112. The outer wall 106 can include an inner surface 108 and an inner surface 110, each of which can define or form portions of the internal cavity 112. For example, the internal cavity 112 can include a first portion defined or formed by the inner surface 108 and a second portion defined or formed by the inner surface 110. In some implementations, the inner surface 108 is tubular (for example, cylindrical). In some implementations, the inner surface 110 narrows or tapers toward a region where the internal cavity 112 meets with the fluid passageway 114 of the protrusion 102. In some implementations, the portion of the internal cavity 112 defined or formed by inner surface 110 is frustoconical. Rim 104 can extend around all or a portion of a perimeter of the outer wall 106 at or near a region where the protrusion 102 connects to the outer wall 106 (see FIG. 1B, 2B).

Figure 3B:
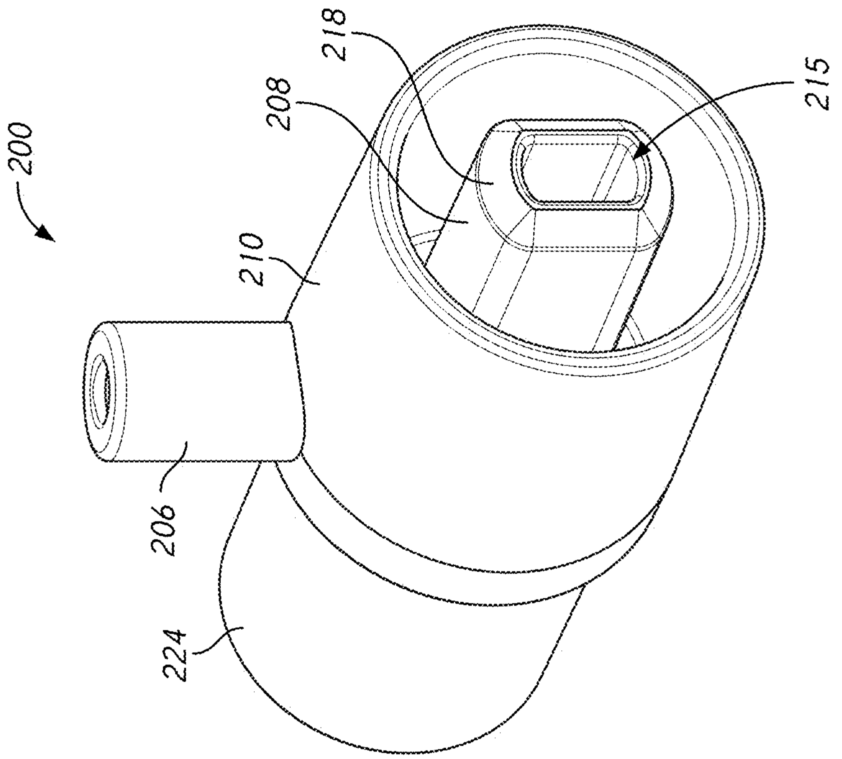
FIGS. 3A-3E illustrate perspective views of an airway adapter of the ventilation assembly of FIGS. 1A-2C in accordance with aspects of this disclosure.
Figure 3A:
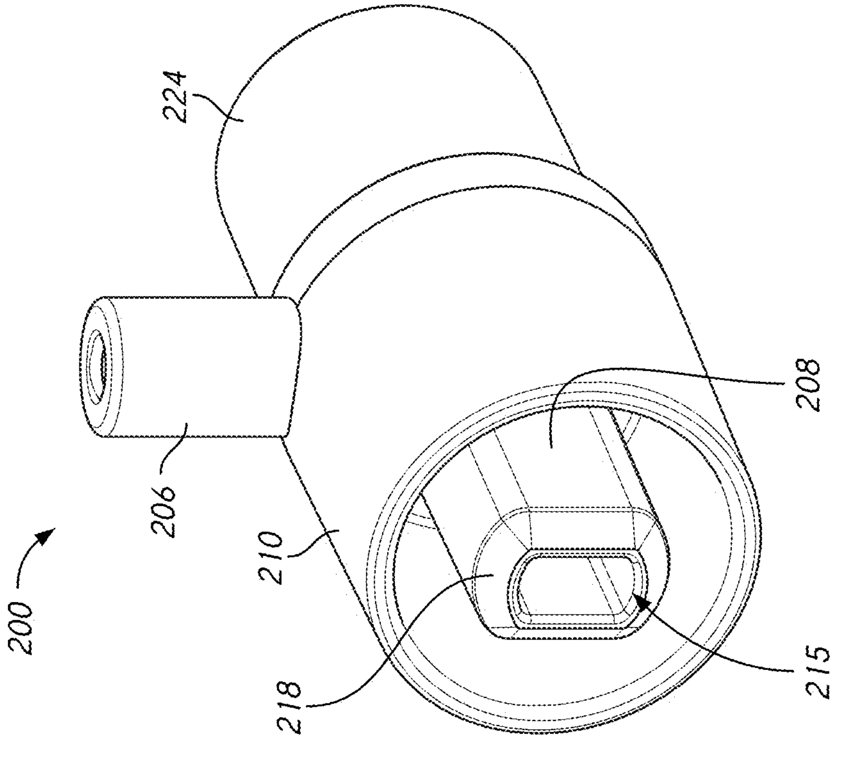
Figure 3D:
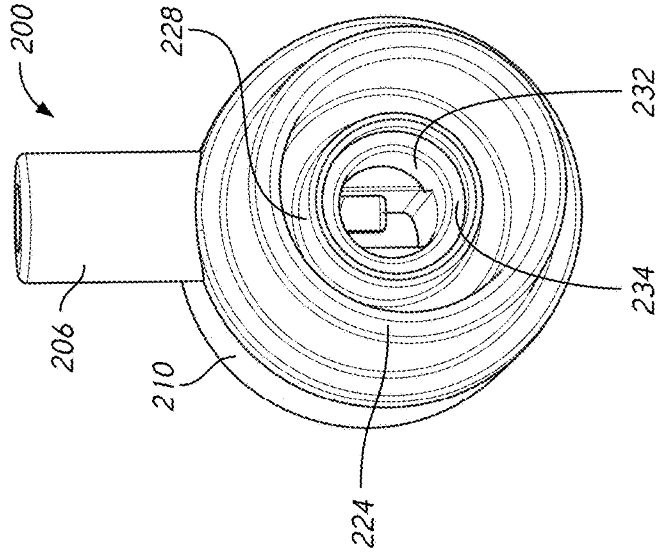
Figure 3E:
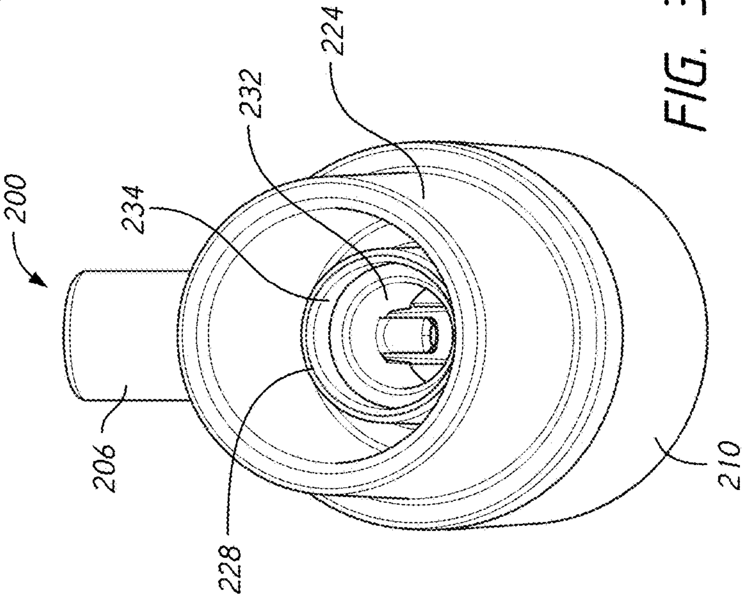
Figure 3C:
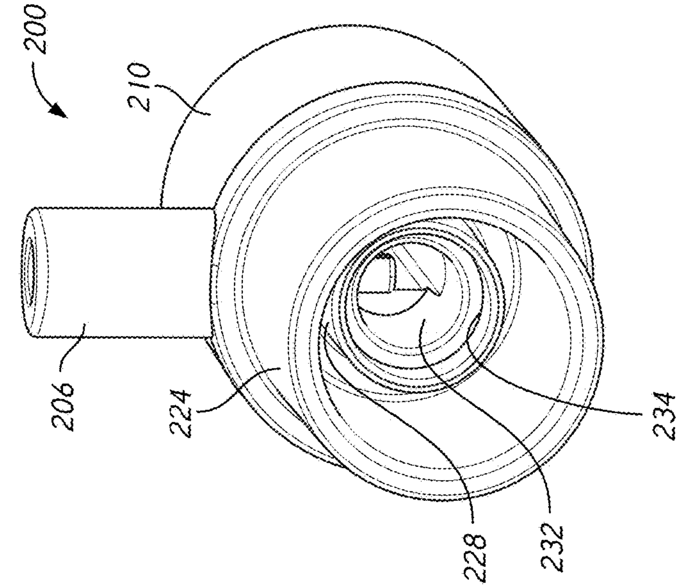
Figure 3G:
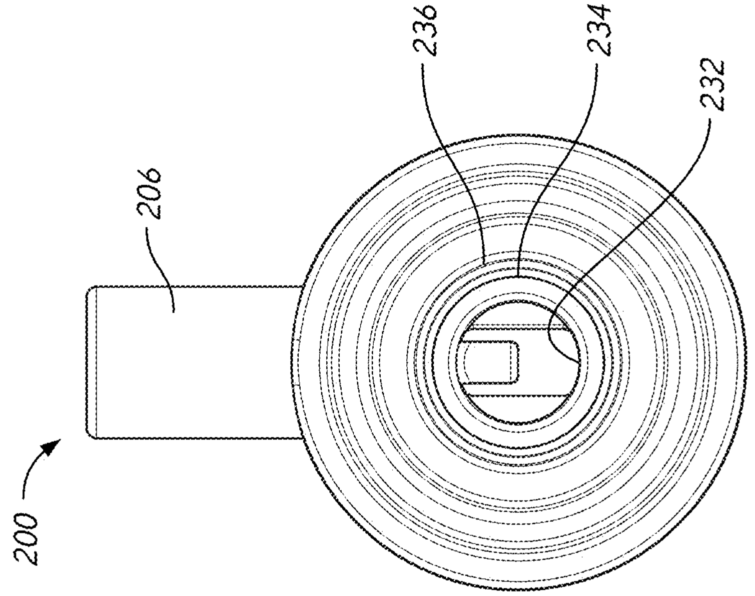
FIG. 3G illustrates a back view of the airway adapter of FIGS. 3A-3E in accordance with aspects of this disclosure.
Figure 3F:
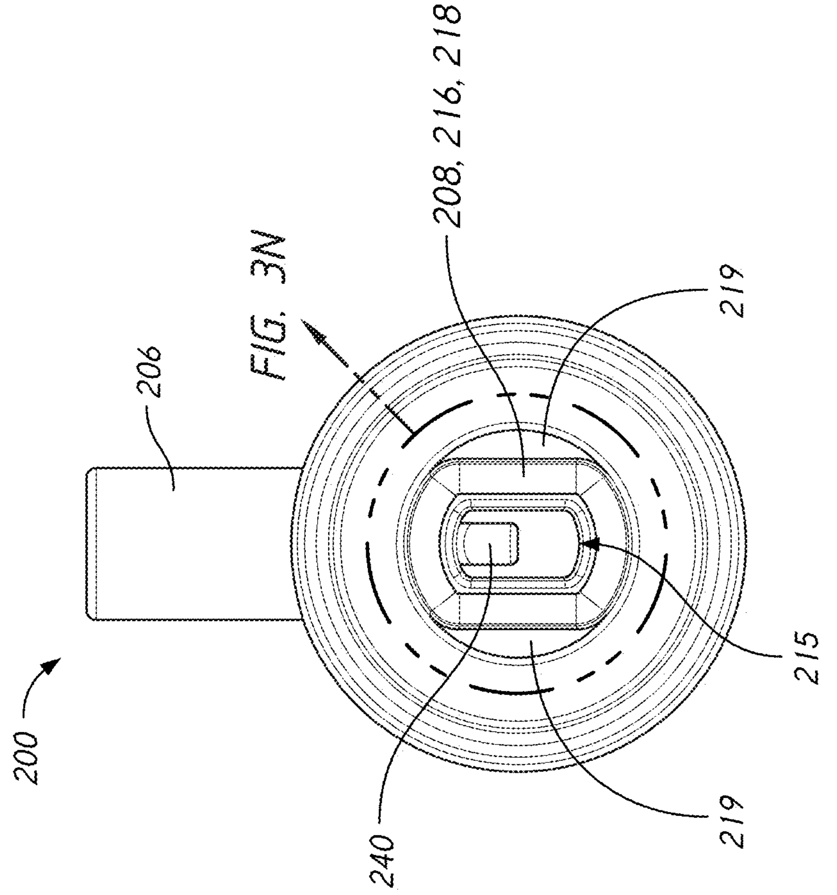
FIG. 3F illustrates a front view of the airway adapter of FIGS. 3A-3E in accordance with aspects of this disclosure.
Figure 3H:
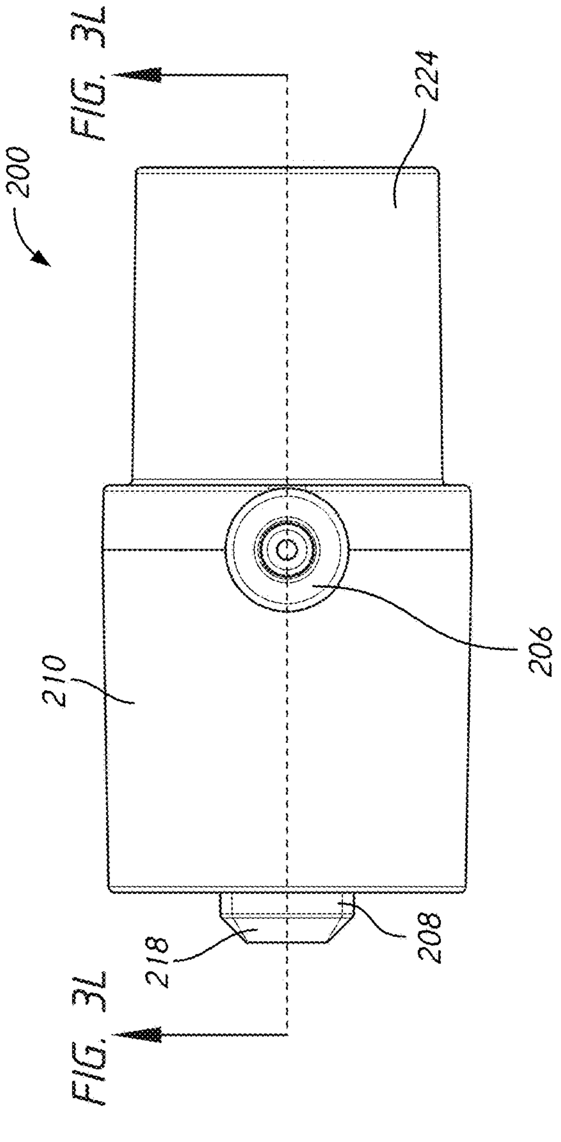
FIG. 3H illustrates a top view of the airway adapter of FIGS. 3A-3E in accordance with aspects of this disclosure.
Figure 3I:
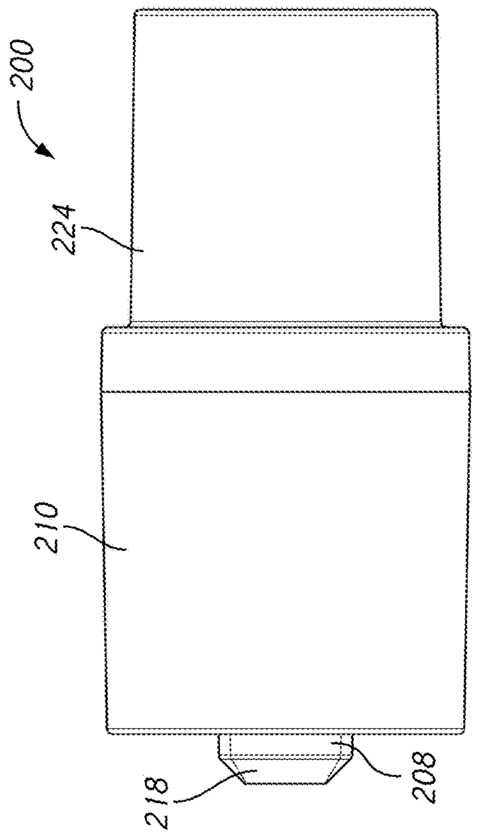
FIG. 3I illustrates a bottom view of the airway adapter of FIGS. 3A-3E in accordance with aspects of this disclosure.
Figure 3K:
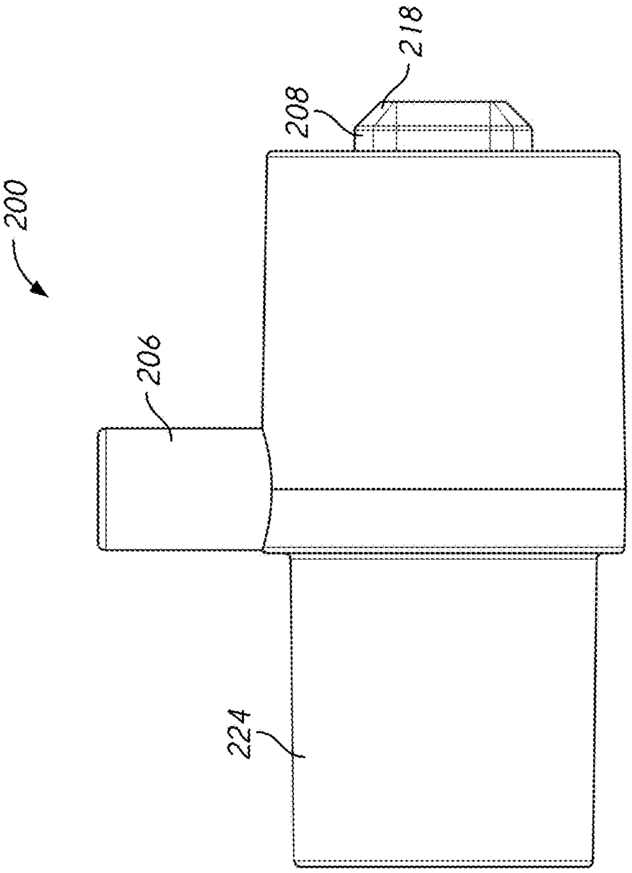
FIG. 3K illustrates another side view of the airway adapter of FIGS. 3A-3E in accordance with aspects of this disclosure.
Figure 3J:
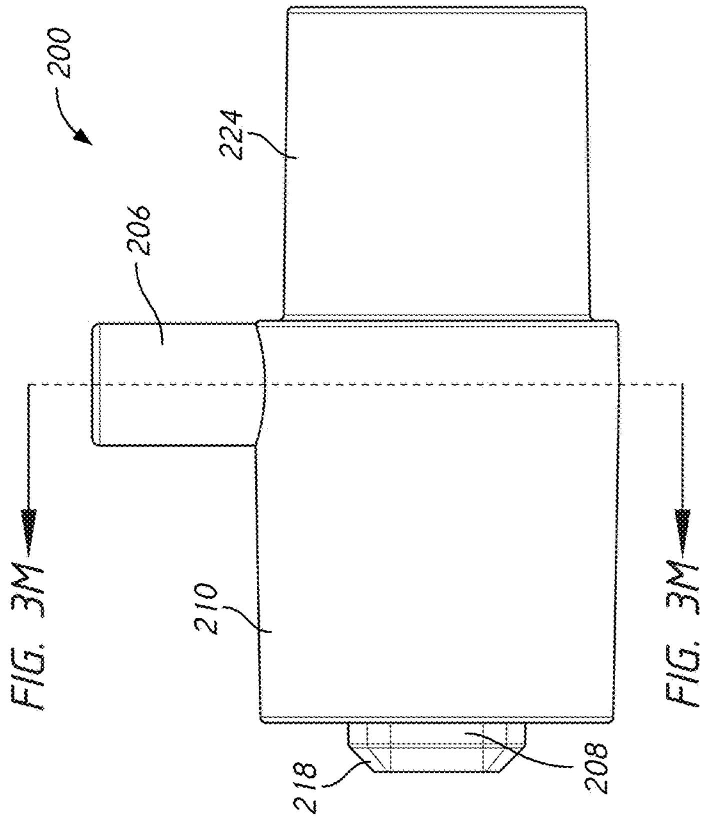
FIG. 3J illustrates a side view of the airway adapter of FIGS. 3A-3E in accordance with aspects of this disclosure.
Figure 3L:
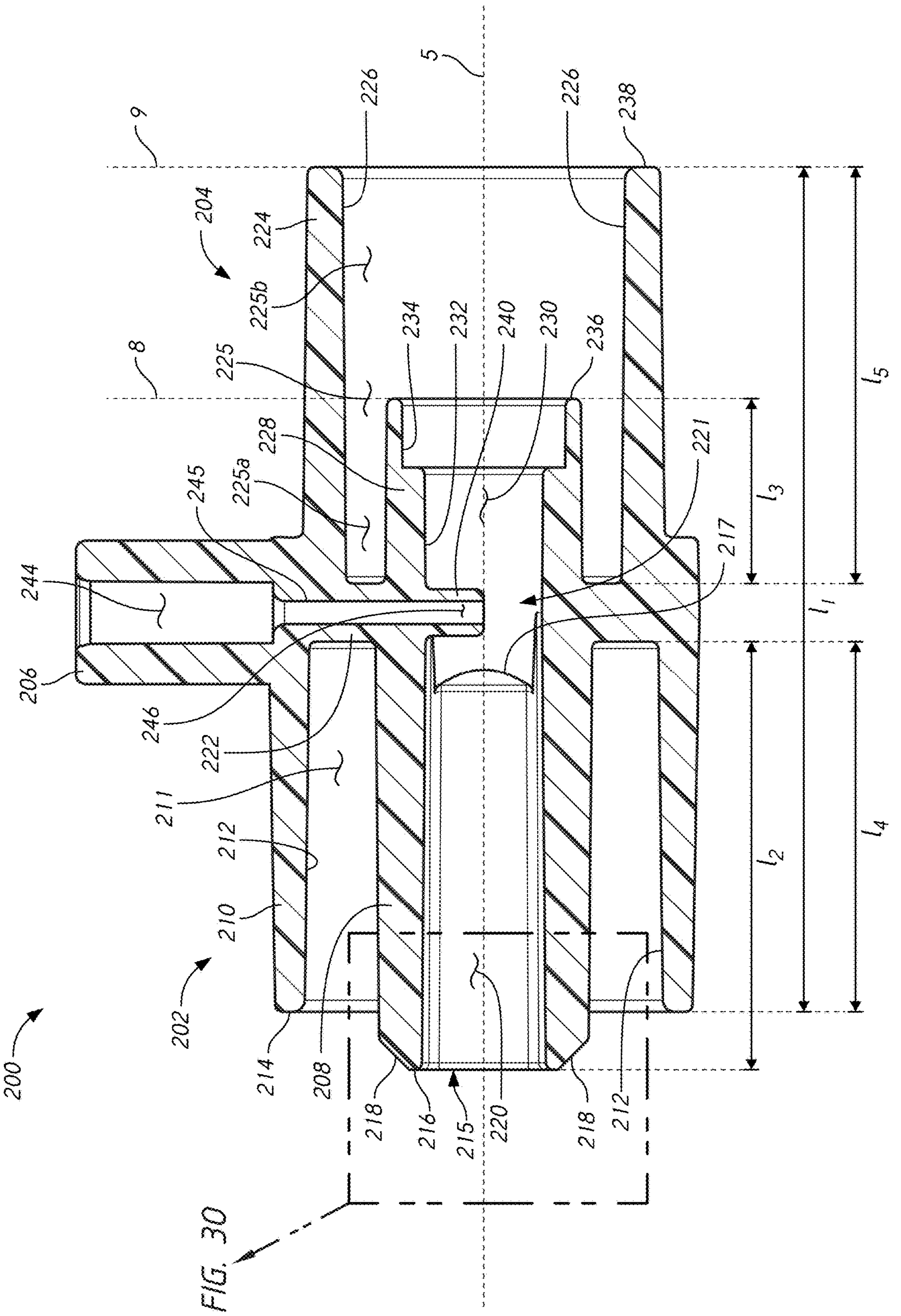
FIG. 3L illustrates a cross-sectional view taken through a portion of the airway adapter shown in FIG. 3H in accordance with aspects of this disclosure.

While FIGS. 1A-1C and 2A-2C illustrate the airway adapter 200 in the context of ventilation assemblies 10, 10', FIGS. 3A-3M illustrate the airway adapter 200 or portions thereof alone to better illustrate aspects of the airway adapter 200. FIGS. 3A-3B illustrate front perspective views of airway adapter 200, and FIGS. 3C-3E illustrate back perspective views of airway adapter 200. FIGS. 3F-3K illustrate front, back, top, bottom, and side views of airway adapter 200, respectively. FIG. 3L illustrates a cross-sectional view of the airway adapter 200 taken through a portion of the airway adapter shown in FIG. 3H, and FIG. 3M illustrates another cross-sectional view of the airway adapter 200 taken through a portion of the airway adapter shown in FIG. 3J.

Figure 3N:
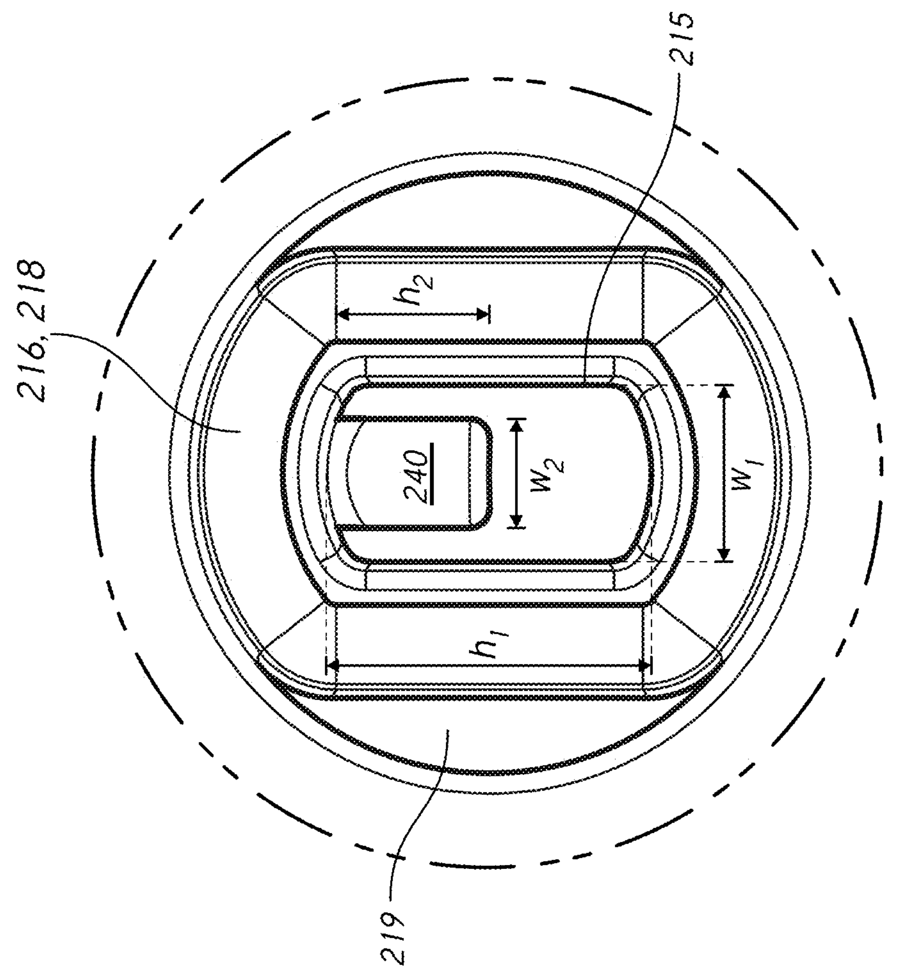
FIG. 3N illustrates an enlarged view of a portion of the airway adapter shown in FIG. 3F in accordance with aspects of this disclosure.
Figure 3M:
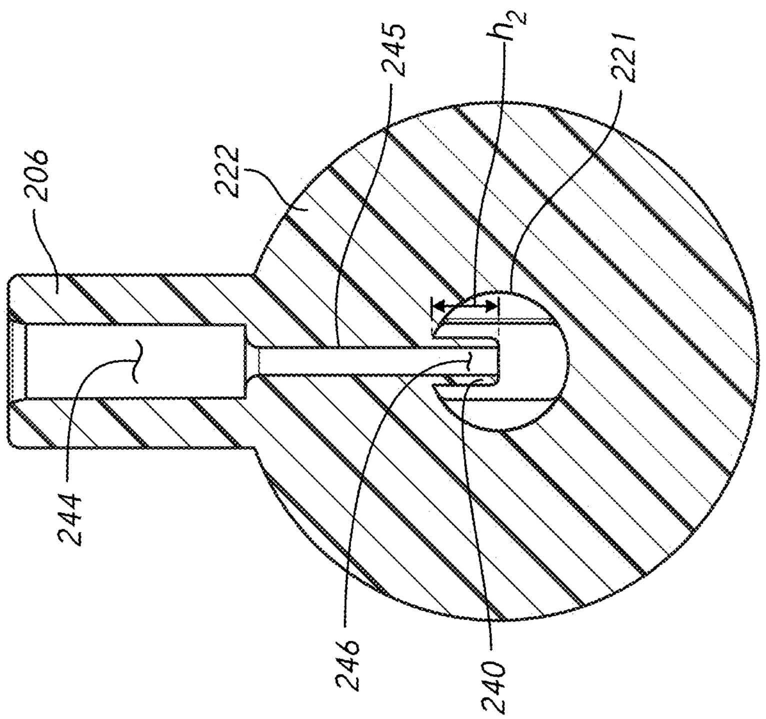
FIG. 3M illustrates a cross-sectional view taken through a portion of the airway adapter shown in FIG. 3J in accordance with aspects of this disclosure.
Figure 30:
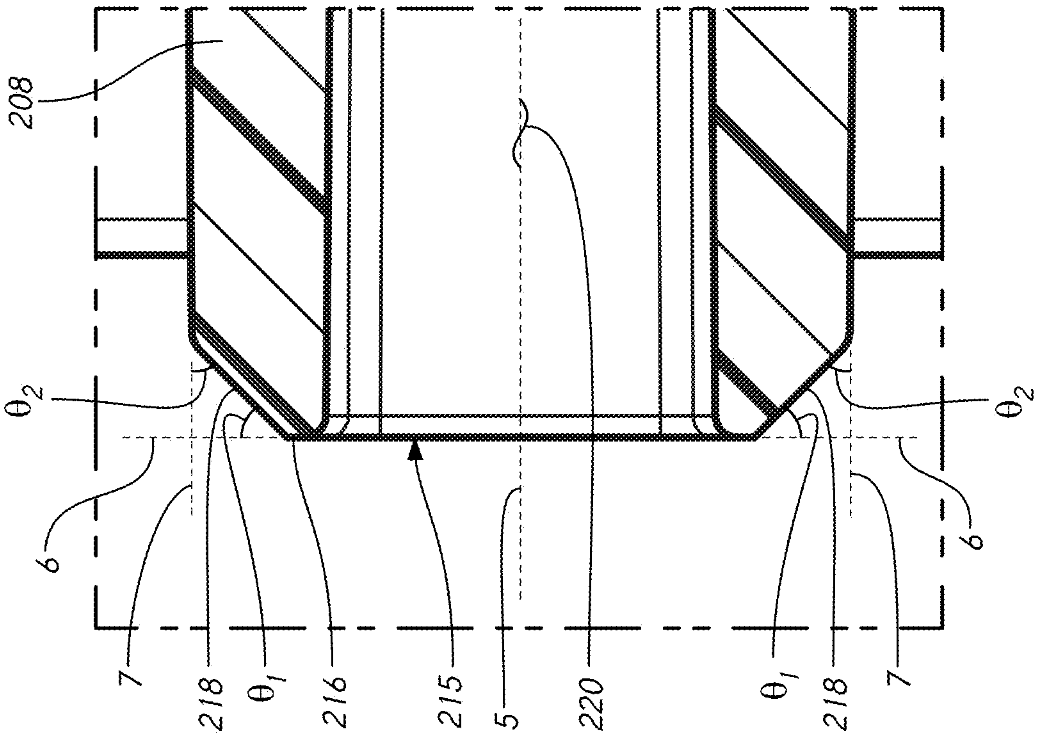

As shown throughout FIGS. 3A-3N, airway adapter 200 can include a first outer wall 210, a second outer wall 224. In some implementations, airway adapter 200 can include a sampling portion. For example, airway adapter 200 can include one or more ports defining and/or forming the sampling portion. For example, airway adapter can include a port 206. Port 206, which is further described below, can extend outward from an outer surface of the outer wall 210 and/or the outer wall 224, as shown. Port 206 can be coupled with a tube (such as tube 201 as shown in FIGS. 1A, 2A) which connects the port 206 to a monitoring system. In some implementations, port 206 can facilitate sampling of gases flowing into and/or out of adapter 200 for determination of gaseous composition (for example, of $CO_2$ in exhaled breath) and/or respiratory rate, for example, via such monitoring system coupled to port 206 via tube 201. The outer wall 210 can be tubular, for example cylindrical. Similarly, the outer wall 224 can be tubular, for example, cylindrical.

As discussed previously, airway adapter 200 can be coupled with the ET tube adapter 100. Such coupling can be via the outer wall 210. For example, with reference to at least FIGS. 1B-1C and 2B-2C, the outer wall 210 can be sized and/or shaped to receive the outer wall 106 of ET tube adapter 100. The outer wall 210 can be secured (for example, removably secured) to the outer wall 106. For example, the outer wall 210 can be secured to the outer wall 106 via a friction fit. While the figures illustrate the outer wall 210 being larger than outer wall 106, the outer wall 210 can be alternatively be smaller than the outer wall 106 so as to secure within the outer wall 106 in some configurations.

As discussed previously, the airway adapter 200 can be coupled with flow sensor 30 or flow sensor 50. Such coupling can be via the outer wall 224. For example, as shown in at least FIGS. 1B-1C and 2B-2C, the outer wall 224 can be sized and/or shaped to be received in the outer wall 32 of flow sensor 30 and/or outer wall 52 of flow sensor 50. The outer wall 224 can be secured (for example, removably secured) to the outer wall 32 of flow sensor 30 and/or outer wall 52 of flow sensor 50. For example, the outer wall 224 can be secured to the outer wall 32 and/or outer wall 52 via a friction fit. While the figures illustrate the outer wall 224 being smaller than outer wall 32, 52, the outer wall 224 can be alternatively larger than the outer wall 32, 52 so as to secure around the outer wall 32, 52. As also discussed previously, the airway adapter 200 can be coupled to the ventilation tube connector 40, for example, in ventilation assemblies which do not include a flow sensor (such as flow sensors 30, 50). In such configurations, the outer wall 224 of the airway adapter 200 can be secured around or within a portion of the ventilation tube connector 40, for example, in a similar manner as that illustrated in FIGS. 1A and 2A with respect to flow sensor 30, 50. Such securement between the outer wall 224 and the portion of the ventilation tube connector 40 can be via a friction fit.

With reference to FIG. 3L, the outer wall 210 can define and/or include an internal cavity 211 (which can also be referred to as a “bore”), and the outer wall 224 can define and/or include an internal cavity 225 (which can also be referred to as a “bore”). The airway adapter 200 can include a barrier wall 222 that can partition (for example, separate) the internal cavities 211, 225 from one another. The barrier wall 222 can be positioned at or proximate to a region where the outer walls 210, 224 join (see FIG. 3L). Barrier wall 222 can include an opening 221 which can have a circular cross-section, among others (see FIGS. 3L and 3M).

As shown through FIGS. 3A-3B, 3F, and 3H-3L, airway adapter 200 can include an internal projection 208 (which can also be referred to as an “inner wall”). Internal projection 208 can be positioned at least partially within the internal cavity 211 and/or spaced from the outer wall 210. For example, internal projection 208 can be spaced from an inner surface 212 of the outer wall 210. Internal projection 208 can extend outward from the barrier wall 222 and can include and/or define a fluid passageway 220. Such fluid passageway 220 can be in fluid communication with at least a portion of the opening 221 (also referred to herein as "barrier wall opening") of the barrier wall 222. Internal projection 208 can extend around the opening 221 of the barrier wall 222. As illustrated in at least FIGS. 3A-3B, 3L, and 3N, internal projection 208 can include an opening 215 at a free (for example, "cantilevered") end 216 into the fluid passageway 220. Such free end 216 can be opposite another end of the internal projection 208 that is connected to the barrier wall 222.

In some configurations, airway adapter 200 can include an internal projection 228 (which can also be referred to as an "inner wall"). Internal projection 228 can be positioned within the internal cavity 225 and/or spaced from the outer wall 224. For example, internal projection 228 can be spaced from an inner surface 226 of the outer wall 224. Internal projection 228 can extend outward from the barrier wall 222 (for example, in an opposite direction as internal projection 208) and can include and/or define a fluid passageway 230. Such fluid passageway 230 can be in fluid communication with at least a portion of the opening 221 of the barrier wall 222 and the fluid passageway 220. Internal projection 228 can extend around the opening 221 of the barrier wall 222.

As mentioned previously, airway adapter 200 can include a port 206 which includes and/or defines a fluid passageway 244 (see FIG. 3L). Port 206 can extend away from outer surface of the outer wall 210 and/or outer wall 224 as discussed above and therefore can be referred to as an "external" port. Airway adapter 200 can additionally include a port 240. With reference to at least FIG. 3L, port 240 can extend from the barrier wall 222, for example, at and/or within the opening 221 and/or proximate a region where the internal projection 208 (and/or fluid passageway 220) meets the barrier wall 222 and/or the internal projection 228 (and/or fluid passageway 230). As such, port 240 can be referred to as an "internal" port. Port 240 can include and/or define a fluid passageway 246 which can be in fluid communication with the opening 221 of the barrier wall 222 and the fluid passageways 220, 230 of the internal projections 208, 228. The airway adapter 200 can include one or more channels defining one or more fluid passageways fluidly connecting fluid passageway 244 of port 206 and fluid passageway 246 of port 240. For example, airway adapter 200 can include a channel 245 extending through a portion of the barrier wall 222, outer wall 210, and/or outer wall 224 including and/or defining a fluid passageway which is in fluid communication with the fluid passageways 244, 246. In some configurations, the channel 245 and the port 246 can define a single fluid passageway (for example, fluid passageway 246) extending there through that is in fluid communication with the fluid passageway 244 and fluid passageways 220, 230, and/or opening 221. As mentioned previously, the airway adapter 200 can include a sampling portion that can allow and/or facilitate sampling of a portion of fluid flowing through the airway adapter 200 when in use and/or can facilitate determination of respiratory rate or another characteristic based upon, for example, fluid flowing into, out of, and/or through adapter 200. Port 206, fluid passageway 244, channel 245, fluid passageway 246, and/or port 240, can define or form such sampling portion of the airway adapter 200.

With reference to at least FIGS. 1C, 2C, and 3L, internal projection 208 can extend within the internal cavity 112 of the ET tube adapter 100 when the airway adapter 200 is coupled with the ET tube adapter 100. In such configuration, the internal projection 208 can facilitate fluid communication between the ET tube 101 and ET tube connector 100 and fluid passageways 246, 244 of ports 240, 206, channel 245, and/or fluid passageways 220, 230. Internal projection 208 can have a first end connected to the barrier wall 222 and a second end 216 (which can also be referred to herein as a "free end" or "cantilevered end") opposite the first end. As illustrated in FIG. 3L, the second end 216 of the internal projection 208 can be positioned outside the outer wall 210 and/or internal cavity 211. For example, the internal projection 208 can have a length $l_2$ that is greater than a length $l_4$ of the outer wall 210 with reference to the barrier wall 222. In such configurations, end 216 of the internal projection 208 can be positioned closer to the opening 120 defined at the meeting region of the protrusion 102 (and fluid passageway 114) and the outer wall 106 (and internal cavity 112) when the airway adapter 200 is coupled to the ET tube adapter 100. Such configurations can advantageously reduce internal void volumes ("dead space") that would otherwise be present when the airway adapter 200 is coupled with the ET tube connector 100 and ET tube 101.

Length $l_2$ can be between approximately 0.2 inch and approximately 1 inch, for example, between approximately 0.3 inch and approximately 0.9 inch, between approximately 0.4 inch and approximately 0.8 inch, between approximately 0.5 inch and approximately 0.7 inch, or between approximately 0.6 inch and 0.7 inch, or any value or range between any of these values or ranges or any value or range bounded by any combination of these values, although values or ranges outside these values or ranges can be used in some cases.

Length $l_4$ can be between approximately 0.2 inch and approximately 1 inch, for example, between approximately 0.3 inch and approximately 0.9 inch, between approximately 0.4 inch and approximately 0.8 inch, between approximately 0.5 inch and approximately 0.7 inch, or between approximately 0.7 inch and 0.8 inch, or any value or range between any of these values or ranges or any value or range bounded by any combination of these values, although values or ranges outside these values or ranges can be used in some cases.

A difference between the length $l_2$ of the internal projection 208 and the length $l_4$ of outer wall 310 can be at least 0.02 inch, at least 0.03 inch, at least 0.04 inch, at least 0.05 inch, at least 0.06 inch, at least 0.07 inch, at least 0.08 inch, at least 0.09 inch, or at least 0.1 inch, or any value therebetween, although values outside these values or ranges can be used in some cases. A ratio between the length $l_2$ of the internal projection 208 and the length $l_4$ of outer wall 310 can be between approximately 1 and approximately 2, for example, between approximately 1 and approximately 1.05, between approximately 1 and approximately 1.1, between approximately 1 and approximately 1.2, between approximately 1 and approximately 1.3, between approximately 1 and approximately 1.4, between approximately 1 and approximately 1.5, between approximately 1 and approximately 1.6, between approximately 1 and approximately 1.7, between approximately 1 and approximately 1.8, between approximately 1 and approximately 1.9, or between approximately 1.1 and approximately 1.2, although values or ranges outside these values or ranges can be used in some cases.

FIG. 3L illustrates a length $l_1$ of airway adapter 200. Length $l_1$ can represent a length or distance from a free end 214 of outer wall 210 and a free end 238 of outer wall 224. Length $l_1$ can be larger than any or all of lengths $l_2$, $l_3$, $l_4$, and/or $l_5$ discussed elsewhere herein. Length $l_1$ can be between approximately 1 inch and approximately 3 inch, for example, between approximately 1.1 inch and approximately 2.9 inch, between approximately 1.2 inch and approximately 2.8 inch, between approximately 1.3 inch and approximately 2.7 inch, between approximately 1.4 inch and approximately 2.6 inch, between approximately 1.5 inch and approximately 2.5 inch, between approximately 1.6 inch and approximately 2.4 inch, between approximately 1.7 inch and approximately 2.3 inch, between approximately 1.8 inch and approximately 2.2 inch, between approximately 1.9 inch and approximately 2.1 inch, or between approximately 1.3 inch and approximately 1.5 inch, or any value or range between any of these values or ranges or any value or range bounded by any combination of these values, although values or ranges outside these values or ranges can be used in some cases.

With reference to FIGS. 1B-1C, when the airway adapter 200 is coupled with the ET tube adapter 100 and/or the flow sensor 30, a common axis 3 can extend through a center of the protrusion 102, a center of the internal cavity 112, a center of the internal projection 208 (and/or outer wall 210 and/or fluid passageway 220), a center of the internal projection 228 (and/or outer wall 224 and/or fluid passageway 230), and/or a center of the projection 36, outer wall 32, intermediate portion 33, fluid passageway 38, and/or outer wall 34. Similarly, with reference to FIGS. 2B-2C, when the airway adapter 200 is coupled with the ET tube adapter 100 and/or the flow sensor 50, a common axis 3 can extend through a center of the protrusion 102, a center of the internal cavity 112, a center of the internal projection 208 (and/or outer wall 210 and/or fluid passageway 220), a center of the internal projection 228 (and/or outer wall 224 and/or fluid passageway 230), and/or a center of the projection 56, outer wall 52, intermediate portion 53, fluid passageway 58, and/or outer wall 54.

It is not uncommon for ET tube adapters (such as ET tube adapter 100) to have tapering and/or conical (for example, frustoconical) interior portions. For example, with reference to FIGS. 1B and 2B, inner surface 110 of outer wall 106 of ET tube connector 100 can have a tapering and/or conical (for example, frustoconical) profile which can define a frustoconical portion of the internal cavity 112 proximate the opening 120 into the protrusion 102 and fluid passageway 114. End 216 of internal projection 208 can be sized and/or shaped to allow the opening 215 and fluid passageway 220 to be positioned as close as possible to the opening 120 of the ET tube connector 100. For example, with reference to FIGS. 1B-1C, 2B-2C, and 3L, end 216 of internal projection 208 can be chamfered, as illustrated by reference numeral 218. End 216 can be chamfered around all or a portion of the opening 215. For example, all or a portion of a perimeter of end 216 can be chamfered around opening 215. In some cases, an entire perimeter of end 216 can be chamfered around opening 215. In some cases, end 216 can be chamfered with a curved chamfer around all or a portion of the opening 215. Such curved chamfer is illustrated in at least FIGS. 3A-3B and 3H-3I.

Advantageously, providing all or a portion of end 216 of internal projection 208 with a chamfer (for example, curved chamfer) can facilitate mating and/or flush contact between inner surface 110 of ET tube adapter 100 (which can be frustoconical, for example) and end 216 around the opening 215. Such configurations can allow end 216 to get as close as possible to opening 120 and can minimize dead space within the internal cavity 112 that may otherwise exist if end 216 was positioned away from and/or not in such mating contact with inner surface 110.

The internal projection 208 can be rigid. For example, the internal projection 208 can be not compressible and/or not extendable. The internal projection 208 can be not compressible and/or not extendable relative to an axis extending through and/or along a length of the internal projection 208 and/or a length of the airway adapter 200 (for example, axis 3 and/or 5). Such configuration can advantageously simplify manufacturing of the internal projection 208 alone or in combination with other components of the airway adapter 200, for example, where the internal projection 208 and/or airway adapter 200 is integrally formed (e.g., injection molded). Additionally, such configuration can advantageously ensure that the internal projection 208 (for example, end 216 and/or chamfered region 218) contacts an inner surface of the ET tube adapter 100 (such as inner surface 110) in a consistent manner when the airway adapter 200 is in use. The internal projection 208 can be integrally formed with any or all other portions of the airway adapter 200. For example, the internal projection 208 can be integrally formed with the outer wall 210, barrier wall 222, outer wall 224, internal projection 228, port 240, and/or port 206. Any or all of other components of the airway adapter 200 can be rigid in a similar manner as that discussed above with reference to internal projection 208. For example, any or all of the outer wall 210, barrier wall 222, outer wall 224, internal projection 228, port 240, and/or port 206 can be rigid. The internal projection 228 can be not compressible and/or not extendable. The internal projection 228 can be not compressible and/or not extendable relative to an axis extending through and/or along a length of the internal projection 228 and/or a length of the airway adapter 200 (for example, axis 3 and/or 5).

With reference to FIGS. 3L and 3O, the chamfered region or surface 218 can be chamfered at an angle $\theta_1$ relative to a plane or axis 6 extending along end 216 and/or at an angle $\theta_2$ relative to a plane or axis 7 extending along a surface of the internal projection 208. Plane or axis 6 can be perpendicular to axis 5 extending through a center of the internal projection 208, fluid passageway 220, internal projection 228, fluid passageway 230, outer wall 210, and/or outer wall 224. Additionally or alternatively, plane or axis 7 can be parallel to and/or spaced from such axis 5. Angle $\theta_1$ and/or angle $\theta_2$ can be approximately 10°, approximately 15°, approximately 20°, approximately 25°, approximately 30°, approximately 35°, approximately 40°, approximately 45°, approximately 50°, approximately 55°, or approximately 60°, approximately 65°, approximately 70°, approximately 75°, approximately 80°, between approximately 10° and approximately 80°, between approximately 15° and approximately 75°, between approximately 20° and approximately 70°, between approximately 25° and approximately 65°, between approximately 30° and approximately 60°, between approximately 35° and approximately 55°, or between approximately 40° and approximately 50°, or any value or range between any of these values or ranges or any value or range bounded by any combination of these values, although values or ranges outside these values or ranges can be used in some cases. As mentioned previously, in some configurations, the end 216 comprises a curved chamfer, and in such configurations, a cross-section taken through such curved chamfer can be that which is shown in FIGS. 3L and 3M and have the angles $\theta_1$ and/or angle $\theta_2$ as described above.

With reference to at least FIGS. 3A-3B and 3F, end 216 of internal projection 208 can comprise a rectangular shape.

For example, end 216 can comprises a rounded rectangular shape. The end 216 can comprise a rounded rectangular shape and can be chamfered and/or comprise a curved chamfer around all or a portion of the rounded rectangular shape. With reference to FIGS. 3F and 3N, the end 216 can have a rounded rectangular shape where sides of the rounded rectangular shape are straight and the top and bottom of the rounded rectangular shape are curved.

With reference to FIGS. 3A-3B, 3F, and 3L, and as discussed above, the internal projection 208 can include an opening 215 at end 216 in fluid communication with fluid passageway 220, which allows fluid (for example, gas) to flow into and/or out of the fluid passageway 220. In some configurations, the opening 215 can be non-circular. As shown in the figures, the opening 215 can be rectangular, for example, opening 215 can comprise a rounded rectangular shape (see, for example, FIGS. 3F and 3N). In some alternative configurations, opening 215 is square, and/or comprises a rounded square shape. FIG. 3N illustrates an enlarged view of a portion of the view of the airway adapter 200 shown in FIG. 3F. As shown, the opening 215 can have a height $h_1$ and a width $w_1$. As also shown, the port 240 (discussed above) can have a height (which can also be referred to herein as a "length") $h_2$ and a width $w_2$. The height or length $h_2$ of the port 240 can be the distance by which the port 240 extends from a portion of the barrier wall 222 at or near the opening 221 of the barrier wall 222 (see FIGS. 3M-3N).

Height $h_1$ can be between approximately 0.05 inch and approximately 1 inch, for example, between approximately 0.06 inch and approximately 0.9 inch, between approximately 0.07 inch and approximately 0.8 inch, between approximately 0.08 inch and approximately 0.7 inch, between approximately 0.09 inch and approximately 0.6 inch, between approximately 0.1 inch and approximately 0.5 inch, between approximately 0.2 inch and approximately 0.4 inch, or between approximately 0.1 inch and approximately 0.3 inch, or any value or range between any of these values or ranges or any value or range bounded by any combination of these values, although values or ranges outside these values or ranges can be used in some cases.

Width $w_1$ can be between approximately 0.01 inch and approximately 1 inch, for example, between approximately 0.02 inch and approximately 0.9 inch, between approximately 0.03 inch and approximately 0.8 inch, between approximately 0.04 inch and approximately 0.7 inch, between approximately 0.05 inch and approximately 0.6 inch, between approximately 0.06 inch and approximately 0.5 inch, between approximately 0.07 inch and approximately 0.4 inch, between approximately 0.08 inch and approximately 0.3 inch, between approximately 0.09 inch and approximately 0.2 inch, or between approximately 0.1 inch and approximately 0.15 inch, or any value or range between any of these values or ranges or any value or range bounded by any combination of these values, although values or ranges outside these values or ranges can be used in some cases.

Height $h_2$ can be between approximately 0.01 inch and approximately 1 inch, for example, between approximately 0.02 inch and approximately 0.9 inch, between approximately 0.03 inch and approximately 0.8 inch, between approximately 0.04 inch and approximately 0.7 inch, between approximately 0.05 inch and approximately 0.6 inch, between approximately 0.06 inch and approximately 0.5 inch, between approximately 0.07 inch and approximately 0.4 inch, between approximately 0.08 inch and approximately 0.3 inch, between approximately 0.09 inch and approximately 0.2 inch, or between approximately 0.1 inch and approximately 0.15 inch, or any value or range between any of these values or ranges or any value or range bounded by any combination of these values, although values or ranges outside these values or ranges can be used in some cases.

Width $w_2$ can be between approximately 0.01 inch and approximately 1 inch, for example, between approximately 0.02 inch and approximately 0.9 inch, between approximately 0.03 inch and approximately 0.8 inch, between approximately 0.04 inch and approximately 0.7 inch, between approximately 0.05 inch and approximately 0.6 inch, between approximately 0.06 inch and approximately 0.5 inch, between approximately 0.07 inch and approximately 0.4 inch, between approximately 0.08 inch and approximately 0.3 inch, between approximately 0.09 inch and approximately 0.2 inch, between approximately 0.05 inch and approximately 0.1 inch, or between approximately 0.06 inch and approximately 0.07 inch, or any value or range between any of these values or ranges or any value or range bounded by any combination of these values, although values or ranges outside these values or ranges can be used in some cases.

In some cases, it can be beneficial to minimize the difference between the width $w_1$ of opening 215 and width $w_2$ of the port 240 to reduce dead space within the airway adapter 200 and along the fluid flow path flowing therethrough (for example, along a fluid flow path within the airway adapter 200 defined at least in part by the fluid passageway 220, opening 221, and/or fluid passageway 230). At the same time, it can be beneficial to allow fluid flowing through the internal projection 208 and fluid passageway 220 to flow around port 240 (for example, sides of port 240) in addition to flowing underneath port 240, for example, to facilitate fluid flow through internal projection 228, fluid passageway 228, and/or internal cavity 225 of airway adapter 200. In some cases, a ratio between the width $w_1$ and $w_2$ can be between approximately 1 and approximately 2 in order to balance both beneficial features. For example, the ratio between the width $w_1$ and $w_2$ can be between approximately 1.1 and approximately 1.9, between approximately 1.2 and approximately 1.8, between approximately 1.3 and approximately 1.7, between approximately 1.4 and approximately 1.6, between approximately 1.4 and approximately 1.8, or between approximately 1.6 and approximately 1.7, or any value or range between any of these values or ranges, or any value or range bounded by any combination of these values, although values or ranges outside these values or ranges can be used in some cases.

In some cases, it can be beneficial to minimize the difference between the height $h_1$ of opening 215 and the height or length $h_2$ of the port 240 to reduce dead space within the airway adapter 200 and along the fluid flow path flowing therethrough (for example, along a fluid flow path within the airway adapter 200 defined at least in part by the fluid passageway 220, opening 221, and/or fluid passageway 230). At the same time, it can be beneficial to have height $h_1$ be greater than height or length $h_2$ by a certain amount to facilitate flow of fluid into the port 240 (for example, from underneath).

In some cases, a ratio between the heights $h_1$ and $h_2$ can be between approximately 1 and approximately 3 in order to achieve both benefits. For example, the ratio between the height $h_1$ and height or length $h_2$ can be between approximately 1.1 and approximately 2.9, between approximately 1.2 and approximately 2.8, between approximately 1.3 and approximately 2.7, between approximately 1.4 and approximately 2.6, between approximately 1.5 and approximately 2.5, between approximately 1.6 and approximately 2.4, between approximately 1.7 and approximately 2.3, between approximately 1.8 and approximately 2.2, between approximately 1.9 and approximately 2.1, or between approximately 1.5 and approximately 2.5, or any value or range between any of these values or ranges, or any value or range bounded by any combination of these values, although values or ranges outside these values or ranges can be used in some cases. As another example, the ratio between the height $h_1$ and height or length $h_2$ can be approximately 2. With reference to FIG. 3L, in some cases the port 240 extends from the barrier wall 222 to a longitudinal axis 5 extending through a center of the internal projection 220 and/or internal projection 228.

With reference to FIG. 3L, in some configurations, the fluid passageway 220 of the internal projection 208 transitions from a rectangular (for example, rounded rectangular cross-section) to a circular cross-section at a transition region 217. Such transition region 217 can be at or proximate to the opening 221 in the barrier wall 222 and/or the port 240. FIG. 3M illustrates a cross-section taken through the port 206 and port 240 as shown in FIG. 3J. As shown in FIG. 3M, the cross-section of the opening 221 can be circular. As also shown, the port 240 can extend into the opening 221 and terminate at or near a center of the cross-section of the opening 221. FIG. 3M also illustrates the height or length $h_2$ of the port 240. With reference to FIG. 3N, in some configurations, the port 240 terminates at or near a center of a cross-section of the opening 215. Such center of the cross-section of the opening 215 and/or the cross-section of the opening 221 can be aligned with a longitudinal axis 5 of the airway adapter 200 (see FIG. 3L).

As discussed previously, the airway adapter 200 can include an internal projection 228 that can be positioned at least partially within the internal cavity 225 and/or spaced from the outer wall 224 (for example, spaced from an inner surface 226 of the outer wall 224). As also discussed previously, internal projection 228 can extend outward from the barrier wall 222 (for example, in an opposite direction as internal projection 208) and can include and/or define a fluid passageway 230. Such fluid passageway 230 can be in fluid communication with at least a portion of the opening 221 of the barrier wall 222, fluid passageway 220 of internal projection 208, fluid passageway 246, channel 245, and/or fluid passageway 244. Internal projection 228 can advantageously reduce dead space that may otherwise exist when airway adapter 200 is connected to flow sensor 30 or 50 or a ventilation tube connector 40. For example, with reference to FIGS. 1C and 2C, internal projection 228 can extend from barrier wall 222 and be positioned at or proximate to a projection 36, 56 of flow sensor 30, 50 when airway adapter 200 is coupled thereto. Accordingly, internal projection 228 reduces or eliminates an internal void volume that may otherwise include the volume within the internal cavity 225 of outer wall 224 (or a portion thereof) (see FIG. 3L).

With reference to FIG. 3L, the internal projection 228 can have a length $l_3$. Length $l_3$ can be between approximately 0.05 inch and approximately 1 inch, for example, between approximately 0.06 inch and approximately 0.9 inch, between approximately 0.07 inch and approximately 0.8 inch, between approximately 0.08 inch and approximately 0.7 inch, between approximately 0.09 inch and approximately 0.6 inch, between approximately 0.1 inch and approximately 0.5 inch, between approximately 0.2 inch and approximately 0.4 inch, or between approximately 0.3 inch and approximately 0.4 inch, or any value or range between any of these values or ranges or any value or range bounded by any combination of these values, although values or ranges outside these values or ranges can be used in some cases.

A length $l_5$ defined between the barrier wall 222 and an end (for example, a "free" end) of the outer wall 224 can be between approximately 0.2 inch and approximately 1 inch, for example, between approximately 0.3 inch and approximately 0.9 inch, between approximately 0.4 inch and approximately 0.8 inch, between approximately 0.5 inch and approximately 0.7 inch, between approximately 0.6 inch and 0.9 inch, or between approximately 0.7 inch and 0.8 inch, or any value or range between any of these values or ranges or any value or range bounded by any combination of these values, although values or ranges outside these values or ranges can be used in some cases.

Length $l_3$ can be smaller than length $l_5$. A difference between the length $l_3$ of the internal projection 228 and the length $l_5$ can be at least 0.05 inch, at least 0.06 inch, at least 0.07 inch, at least 0.08 inch, at least 0.09 inch, at least 0.1 inch, at least 0.2 inch, at least 0.3 inch, at least 0.4 inch, or at least 0.5 inch, or any value therebetween, although values outside these values or ranges can be used in some cases. A ratio between the length $l_5$ and the length $l_3$ can be between approximately 1 and approximately 5, for example, between approximately 1.1 and approximately 4.9, between approximately 1.2 and approximately 4.8, between approximately 1.3 and approximately 4.7, between approximately 1.4 and approximately 4.6, between approximately 1.5 and approximately 4.5, between approximately 1.6 and approximately 4.4, between approximately 1.7 and approximately 4.3, between approximately 1.8 and approximately 4.2, between approximately 1.9 and approximately 4.1, between approximately 2 and approximately 4, between approximately 2.1 and approximately 3.9, between approximately 2.2 and approximately 3.8, between approximately 2.3 and approximately 3.7, between approximately 2.4 and approximately 3.6, between approximately 2.5 and approximately 3.5, between approximately 2.6 and approximately 3.4, between approximately 2.7 and approximately 3.3, between approximately 2.8 and approximately 3.2, between approximately 2.9 and approximately 3.1, between approximately 2 and approximately 2.5, or between approximately 2.2 and approximately 2.3, although values or ranges outside these values or ranges can be used in some cases. A ratio between the length $l_5$ and the length $l_3$ can be at least approximately 1.1, at least approximately 1.2, at least approximately 1.3, at least approximately 1.4, at least approximately 1.5, at least approximately 1.6, at least approximately 1.7, at least approximately 1.8, at least approximately 1.9, at least approximately 2, at least approximately 2.1, at least approximately 2.2, at least approximately 2.3, at least approximately 2.4, at least approximately 2.5, at least approximately 2.6, at least approximately 2.7, at least approximately 2.8, at least approximately 3, at least approximately 3.1, at least approximately 3.2, at least approximately 3.3, at least approximately 3.4, at least approximately 3.5, at least approximately 3.6, at least approximately 3.7, at least approximately 3.8, at least approximately 3.9, or at least approximately 4, although values or ranges outside these values or ranges can be used in some cases.

With continued reference to FIG. 3L, length $l_2$ of the internal projection 208 can be greater than length $l_3$ of the internal projection 228. For example, length $l_2$ can be greater than length $l_3$ by at least approximately 0.1 inch, at least approximately 0.2 inch, at least approximately 0.3 inch, at least approximately 0.4 inch, at least approximately 0.5 inch, at least approximately 0.6 inch, at least approximately 0.7 inch, at least approximately 0.8 inch, at least approximately 0.9 inch, or at least approximately 1 inch, although values or ranges outside these values or ranges can be used in some cases. A ratio between length $l_2$ and length $l_3$ can be between approximately 1 and approximately 5, for example, between approximately 1.5 and approximately 4.5, between approximately 2 and approximately 4, between approximately 2.5 and approximately 3.5, between approximately 2 and approximately 2.5, or between approximately 3.5 and approximately 4, or any value or range between any of these values or ranges or any value or range bounded by any combination of these values, although values or ranges outside these values or ranges can be used in some cases.

In some configurations, the internal projection 228 is configured to secure to a portion of a flow sensor. For example, as shown in FIG. 2C, the internal projection 228 can be configured to secure to a protrusion 51 of flow sensor 50 which can define and/or form part of a fluid passageway 58 extending through the flow sensor 50. Where protrusion 51 is a wall that splits a fluid passageway extending through internal projection 56 of flow sensor 50, internal projection 328 can receive and secure to protrusion 51. With reference to FIG. 3L, the internal projection 228 can include an internal cavity defining the fluid passageway 230 which has a first portion 232 and a second portion 234. The first portion 232 of the internal cavity of the internal projection 228 can comprise a smaller cross-sectional area than the second portion 234. The second portion 234 can also be referred to as a "recessed portion." The second portion 234 can be sized and/or shaped to receive and secure the protrusion 51 of the flow sensor 50. In some embodiments, this configuration can significantly reduce dead space in the airway adapter 200 by entirely or partially "closing off" the internal cavity 225 of the outer wall 224 in and around an end 236 (also referred to as a "free end") of the internal projection 228. The cross-sections of the first and second portions 232, 234 can be circular, as illustrated in at least FIGS. 3C-3E, among other shapes.

With reference to FIG. 3L, the first portion 232 can comprise a greater proportion or percentage of the length $l_3$ of the internal projection 228 than the second portion 234. Alternatively, the first portion 232 can comprise an equal or smaller proportion or percentage of the length $l_3$ of the internal projection 228 than the second portion 234.

With reference to FIG. 3L, the airway adapter 200 can include a first portion 202 that can be coupled to the ET tube adapter 100 and a second portion 204 that can be coupled to the flow sensor 30, 50 or the ventilation tube connector 40. In some cases, the first portion 202 can include or be defined by the outer wall 210 and/or the internal projection 208. In some cases, the second portion 204 can include or be defined by the outer wall 224 and/or the internal projection 228.

As discussed above, the airway adapter 200 can include low dead space in comparison to conventional airway adapters, alone and/or when connected or assembled with other components in a ventilation assembly (such as ventilation assembly 10, 10'). In some configurations, a total dead space of the airway adapter 200 is less than approximately 2.5 ml, less than approximately 2.4 ml, less than approximately 2.3 ml, less than approximately 2.2 ml, less than approximately 2.1 ml, less than approximately 2 ml, less than approximately 1.9 ml, or less than approximately 1.8 ml.

With reference to FIG. 3L, a total interior volume (which may also be referred to as "interior void volume" or "dead space") of the fluid passageway 220, opening 221, fluid passageway 230, and/or the internal cavity 225 (or a portion thereof) may be less than approximately 2.5 ml. Such interior volume can include fluid passageway 220, opening 221, fluid passageway 230, and a portion of the internal cavity 225, for example, a portion of the internal cavity 225 between the free end 236 of the internal projection 228 and the free end 238 of the outer wall 224. A first plane 8 defined along the free end 236 can partition the internal cavity 225 into a first portion 225*a* defined between such first plane 8 and the barrier wall 222 and a second portion 225*b* defined between such first plane 8 and a second plane 9 along the free end 238 of the outer wall 224. Such "first" and "second" planes 8, 9 are illustrated as vertically oriented given the view shown in FIG. 3L. In some configurations, a total interior volume of the first fluid passageway 220, opening 221, second fluid passageway 230 (which can be defined by different sized portions 232, 234 as discussed elsewhere herein), and/or second portion 225*b* is less than approximately 3 ml, less than approximately 2.9 ml, less than approximately 2.8 ml, less than approximately 2.7 ml, less than approximately 2.6 ml, less than approximately 2.5 ml, less than approximately 2.4 ml, less than approximately 2.3 ml, less than approximately 2.2 ml, less than approximately 2.1 ml, or less than approximately 2 ml.

With reference to FIGS. 1C and 2C, a total interior volume (which may also be referred to as "interior void volume" or "dead space") of the airway adapter 200 and ET tube adapter 100 when coupled with one another can be less than approximately 2 ml, less than approximately 1.9 ml, less than approximately 1.8 ml, less than approximately 1.7 ml, less than approximately 1.6 ml, or less than approximately 1.5 ml. For example, with reference to FIGS. 1C, 2C, and 3L, a total interior volume of the first fluid passageway 220, opening 221, second fluid passageway 230 (which can be defined by different sized portions 232, 234 in some configurations), second portion 225*b*, and a portion of the internal cavity 112 defined between the end 216 of internal projection 208 and the opening 120 of ET tube adapter 100 (see "112*a*" in FIGS. 1C, 2C) can be less than approximately 2 ml, less than approximately 1.9 ml, less than approximately 1.8 ml, less than approximately 1.7 ml, less than approximately 1.6 ml, or less than approximately 1.5 ml. As another example, the total interior volume of the airway adapter 200 and ET tube adapter 100 when coupled with one another can be between approximately 1 ml and approximately 2 ml, for example, between approximately 1.1 ml and approximately 1.9 ml, between approximately 1.2 ml and approximately 1.8 ml, between approximately 1.3 ml and approximately 1.7 ml, between approximately 1.4 ml and approximately 1.6 ml, between approximately 1.5 ml and approximately 2 ml, or between approximately 1.6 ml and approximately 1.8 ml, although values or ranges outside these values or ranges can be used in some cases.

With reference to FIGS. 3F and 3N, in some configurations, airway adapter 200 includes one or more protruding portions 219 extending from the barrier wall 222 along a portion or portions of the internal projection 208. Such protruding portions 219 can advantageously provide a smoother and/or gradual transition from the internal projection 208 to the barrier wall 222 that can provide structural integrity at the region where the internal projection 208 and barrier wall 222 connect. Such protruding portion(s) 219 can, for example, provide a gradual transition for side walls of the internal projection 219 to the barrier wall 222 where such side walls are flat/straight.

FIGS. 4A-4D illustrate another embodiment of an airway adapter 200'. Airway adapter 200' can be identical to airway adapter 200 in every respect except as discussed below with reference to internal projection 208' and/or internal projection 228'. Internal projection 208' can be similar or identical to internal projection 208 in many ways. For example, internal projection 208' can include an end 216' and/or a chamfered region or surface 218' that can be identical to end 216 and/or chamfered region or surface 218 described above with reference to internal projection 208. Internal projection 208' can be identical to internal projection 208 except with respect to opening 215' and fluid passageway 220'. Airway adapter 200' can be utilized with either or both of ventilation assemblies 10, 10' in a similar or identical manner as described and/or shown with respect to airway adapter 200.

As can be seen by comparison of FIGS. 3N and 4C and FIGS. 3L and 4D, opening 215' of airway adapter 200' and fluid passageway 220' are smaller than opening 215 and fluid passageway 220 of airway adapter 200. As also shown, opening 215' includes a width $w_1$ similar to opening 215 but includes a height $h_1'$ that is less than $h_1$. As shown and as similar to airway adapter 200, airway adapter 200' can include a port 240 that has a height or length $h_2$ and which can terminate at or near a longitudinal axis 5 extending through the airway adapter 200 (as described above).

Height $h_1'$ can be between approximately 0.01 inch and approximately 1 inch, for example, between approximately 0.02 inch and approximately 0.9 inch, between approximately 0.03 inch and approximately 0.8 inch, between approximately 0.04 inch and approximately 0.7 inch, between approximately 0.05 inch and approximately 0.6 inch, between approximately 0.06 inch and approximately 0.5 inch, between approximately 0.07 inch and approximately 0.4 inch, between approximately 0.08 inch and approximately 0.3 inch, between approximately 0.09 inch and approximately 0.2 inch, between approximately 0.09 inch and approximately 0.15 inch, or between approximately 0.1 inch and approximately 0.15 inch, or any value or range between any of these values or ranges or any value or range bounded by any combination of these values, although values or ranges outside these values or ranges can be used in some cases.

As shown, a gap or distance (for example, a vertical distance given the view shown in FIGS. 4C-4D) $d_1$ can be present between a bottom of opening 215' and the longitudinal axis 5 and/or the bottom of port 240. Distance $d_1$ can be between approximately 0.001 inch and approximately 0.1 inch, for example, between approximately 0.002 inch and approximately 0.09 inch, between approximately 0.003 inch and approximately 0.08 inch, between approximately 0.004 inch and approximately 0.07 inch, between approximately 0.005 inch and approximately 0.06 inch, between approximately 0.006 inch and approximately 0.05 inch, between approximately 0.007 inch and approximately 0.04 inch, between approximately 0.008 inch and approximately 0.03 inch, between approximately 0.009 inch and approximately 0.02 inch, between approximately 0.004 inch and approximately 0.008 inch, or between approximately 0.005 inch and approximately 0.007 inch, or any value or range between any of these values or ranges or any value or range bounded by any combination of these values, although values or ranges outside these values or ranges can be used in some cases.

Distance $d_1$ can be at least approximately 0.001 inch, at least approximately 0.002 inch, at least approximately 0.003 inch, at least approximately 0.004 inch, at least approximately 0.005 inch, at least approximately 0.006 inch, at least approximately 0.007 inch, at least approximately 0.008 inch, at least approximately 0.009 inch, or at least approximately 0.01 inch, although values or ranges outside these values or ranges can be used in some cases.

Figure 4B:
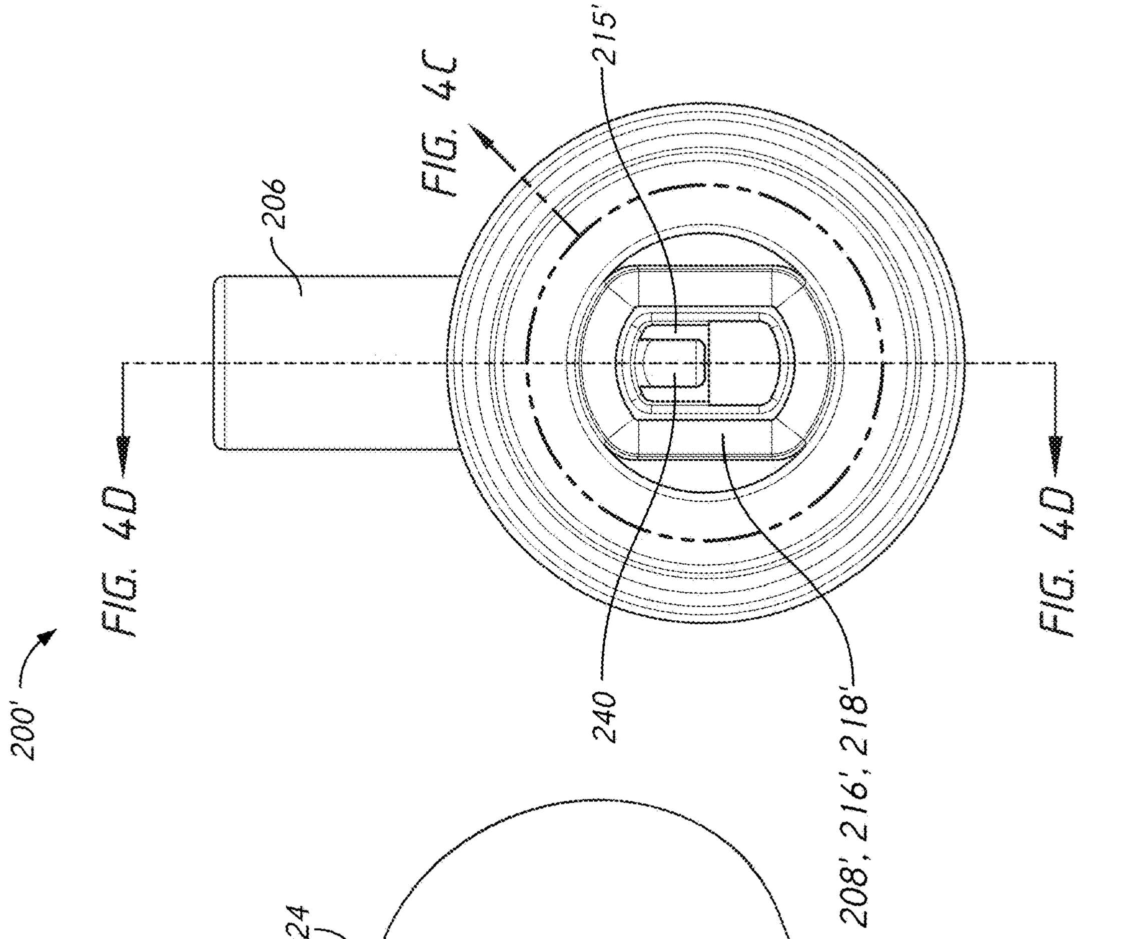
FIG. 4B illustrates a front view of the airway adapter of FIG. 4A in accordance with aspects of this disclosure.
Figure 4A:
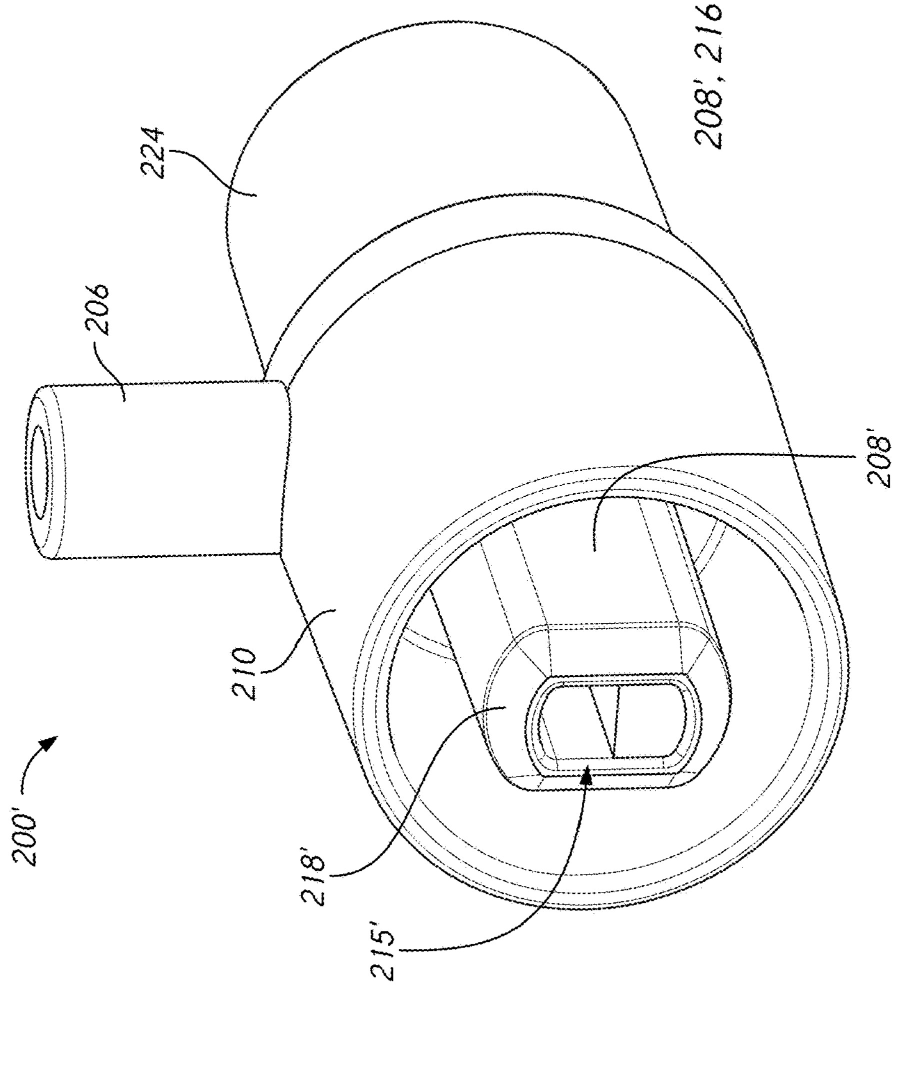
FIG. 4A illustrates a perspective view of another embodiment of an airway adapter in accordance with aspects of this disclosure.
Figure 4C:
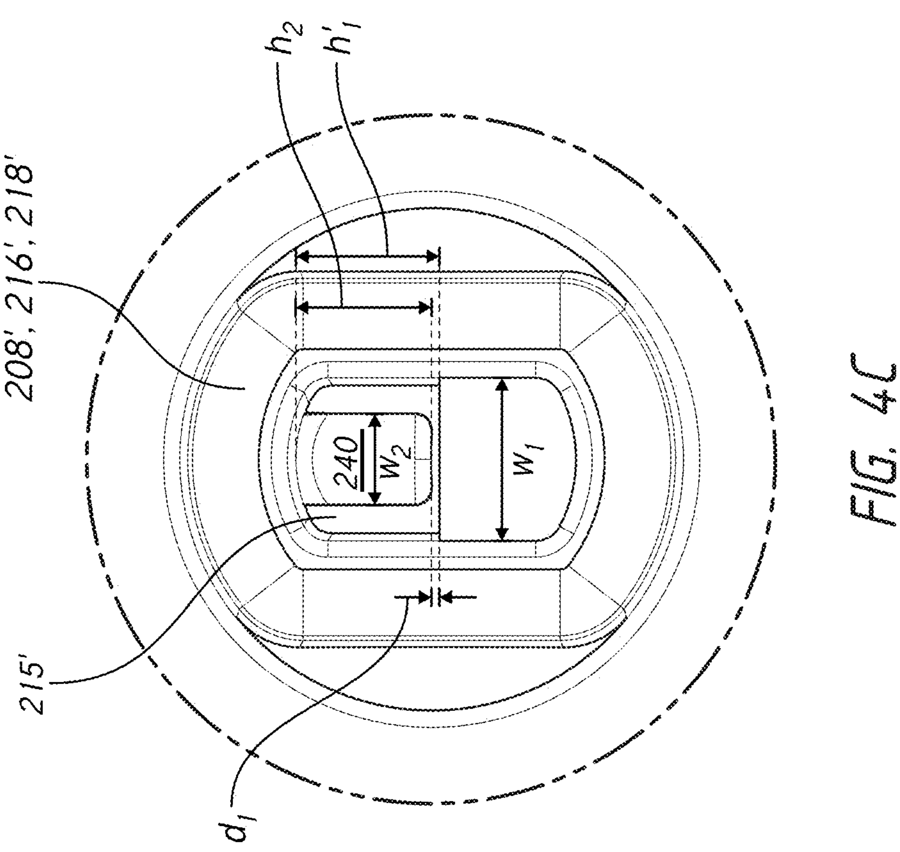
FIG. 4C illustrates an enlarged view of a portion of the airway adapter shown in FIG. 4B in accordance with aspects of this disclosure.

With reference to FIG. 4C, opening 215' and/or fluid passageway 220' can comprise a generally square or rounded or partially rounded square shape. Fluid passageway 220' can transition to from a such generally square or rounded or partially rounded square shape to a circular cross-section at a transition region 217, which can be at or proximate to the opening 221 in the barrier wall 222 and/or the port 240.

Figure 4D:
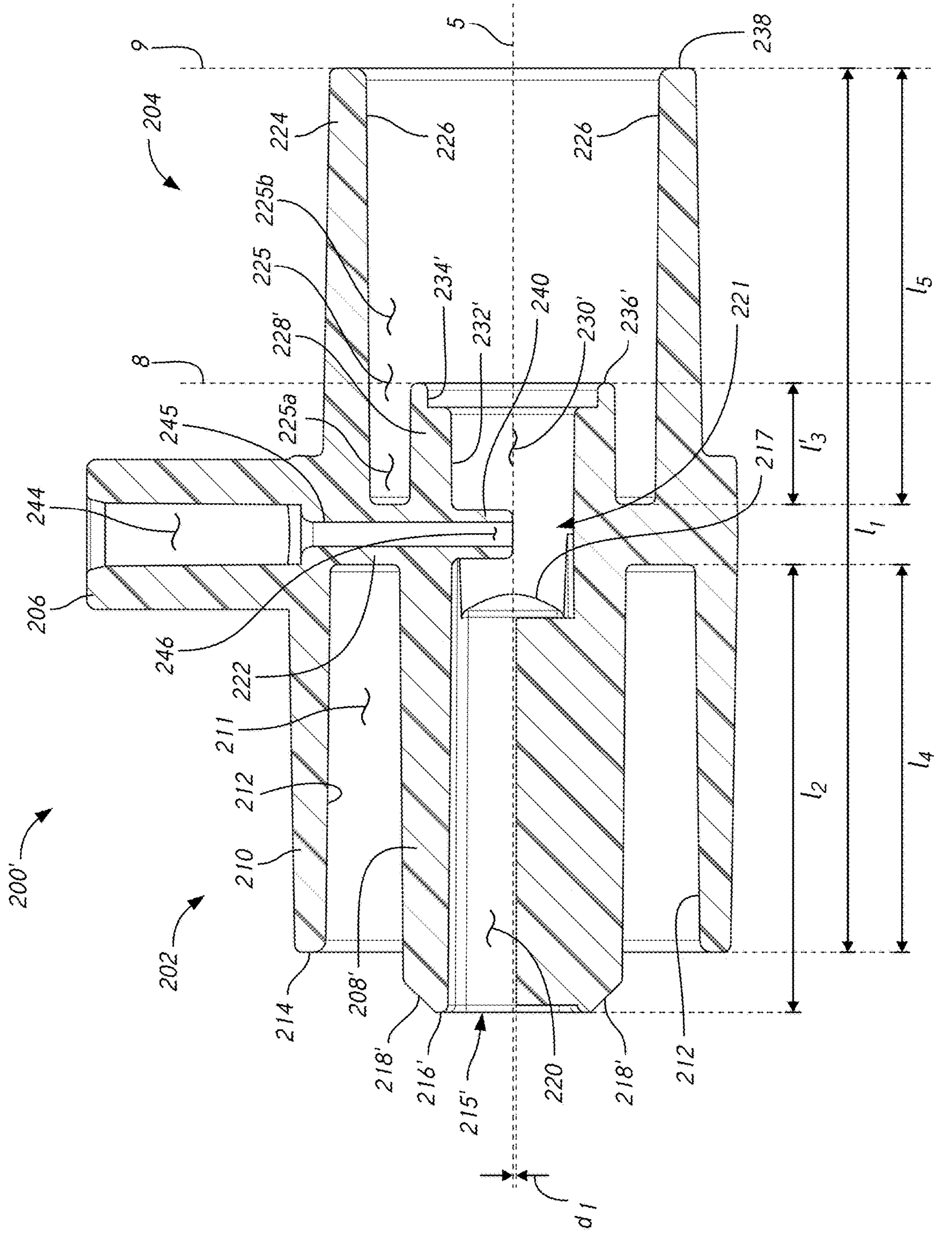
FIG. 4D illustrates a cross-sectional view taken through a portion of the airway adapter in accordance with aspects of this disclosure.

With reference to FIG. 4D, internal projection 228' can be similar or identical to internal projection 228 in many ways. For example, internal projection 228' can include an end 236' that can be identical to end 236 described above with reference to internal projection 228. As can be seen by comparison of FIGS. 3L and 4D, internal projection 228' can have a length $l_3'$ that is smaller than a length $l_3$ of internal projection 228.

Length $l_3'$ can be between approximately 0.05 inch and approximately 1 inch, for example, between approximately 0.06 inch and approximately 0.9 inch, between approximately 0.07 inch and approximately 0.8 inch, between approximately 0.08 inch and approximately 0.7 inch, between approximately 0.09 inch and approximately 0.6 inch, between approximately 0.1 inch and approximately 0.5 inch, between approximately 0.2 inch and approximately 0.4 inch, between approximately 0.05 inch and approximately 0.4 inch, between approximately 0.1 inch and approximately 0.3 inch, or between approximately 0.1 inch and approximately 0.2 inch, or any value or range between any of these values or ranges or any value or range bounded by any combination of these values, although values or ranges outside these values or ranges can be used in some cases.

Length $l_3'$ can be smaller than length $l_5$. A difference between the length $l_3'$ of the internal projection 228' and the length $l_5$ can be at least approximately 0.05 inch, at least approximately 0.06 inch, at least approximately 0.07 inch, at least approximately 0.08 inch, at least approximately 0.09 inch, at least approximately 0.1 inch, at least approximately 0.2 inch, at least approximately 0.3 inch, at least approximately 0.4 inch, at least approximately 0.5 inch, at least approximately 0.6 inch, at least approximately 0.7 inch, at least approximately 0.8 inch, at least approximately 0.9 inch, or at least approximately 1 inch, or any value therebetween, although values outside these values or ranges can be used in some cases.

A ratio between the length $l_5$ and the length $l_3'$ can be between approximately 1 and approximately 5, for example, between approximately 1.1 and approximately 4.9, between approximately 1.2 and approximately 4.8, between approximately 1.3 and approximately 4.7, between approximately 1.4 and approximately 4.6, between approximately 1.5 and approximately 4.5, between approximately 1.6 and approximately 4.4, between approximately 1.7 and approximately 4.3, between approximately 1.8 and approximately 4.2, between approximately 1.9 and approximately 4.1, between approximately 2 and approximately 4, between approximately 2.1 and approximately 3.9, between approximately 2.2 and approximately 3.8, between approximately 2.3 and approximately 3.7, between approximately 2.4 and approximately 3.6, between approximately 2.5 and approximately 3.5, between approximately 2.6 and approximately 3.4, between approximately 2.7 and approximately 3.3, between approximately 2.8 and approximately 3.2, between approximately 2.9 and approximately 3.1, between approximately 2 and approximately 4, or between approximately 3 and approximately 4, although values or ranges outside these values or ranges can be used in some cases. A ratio between the length $l_5$ and the length $l_3$' can be at least approximately 1.1, at least approximately 1.2, at least approximately 1.3, at least approximately 1.4, at least approximately 1.5, at least approximately 1.6, at least approximately 1.7, at least approximately 1.8, at least approximately 1.9, at least approximately 2, at least approximately 2.1, at least approximately 2.2, at least approximately 2.3, at least approximately 2.4, at least approximately 2.5, at least approximately 2.6, at least approximately 2.7, at least approximately 2.8, at least approximately 3, at least approximately 3.1, at least approximately 3.2, at least approximately 3.3, at least approximately 3.4, at least approximately 3.5, at least approximately 3.6, at least approximately 3.7, at least approximately 3.8, at least approximately 3.9, or at least approximately 4, although values or ranges outside these values or ranges can be used in some cases.

First portion 232' and/or second portion 234' of internal projection 228' which can define an internal cavity of internal projection 228' can be similar in all respects as first and second portions 232, 234 (respectively) of internal projection 228 except with respect to being smaller (for example, shorter) than such portions 232, 234.

Aspects of airway adapter 200' can be incorporated into airway adapter 200. By way of non-limiting example, airway adapter 200 can include internal projection 228' (discussed above with reference to FIGS. 4A-4D) instead of internal projection 228.

FIGS. 5A-5M illustrate another embodiment of an airway adapter 300. Airway adapter 300 can be similar or identical to airway adapter 200 and/or airway adapter 200' in some or many ways. For example, with reference to at least FIGS. 5A-5K, airway adapter 300 can include a first outer wall 310, a second outer wall 324, and a sampling portion, which, similar to airway adapter 200, can include one or more ports defining and/or forming the sampling portion. Such sampling portion of airway adapter 300 can include a port 306. First outer wall 310, second outer wall 324, and port 306 can be similar or identical to first outer wall 210, second outer wall 224, and port 206 in some, many, or all respects, and therefore the discussion above with reference to first outer wall 210, second outer wall 224, and port 206 is equally applicable to first outer wall 310, second outer wall 324, and port 306. Outer walls 310 and 324 can each include ends 314 and 338 and internal projections 318, 328 can include ends 316 and 336, respectively. Similar to as described above with reference to port 206, port 306 can be coupled with a tube (such as tube 201 shown in FIGS. 1A, 2A) which can connect port 306 to a monitoring system. In some implementations, port 306 can facilitate sampling of gases flowing into and/or out of adapter 300 for determination of gaseous composition (for example, of $CO_2$ in exhaled breath) and/or respiratory rate, for example, via such monitoring system coupled to port 306 via a tube coupling such monitoring system to port 306 (for example, tube 201). Outer walls 310, 324 can be tubular, for example cylindrical.

Airway adapter 300 can be coupled with an ET tube, for example, via an ET tube adapter coupled to the ET tube, in a variety of ways. For example, airway adapter 300 can be coupled with ET tube adapter 100 in a similar or identical manner as that described and/or shown herein with respect to airway adapter 200. Additionally or alternatively, airway adapter 300 can be coupled with a flow sensor, in a variety of ways. For example, airway adapter 300 can be coupled with flow sensor 30 and/or flow sensor 50 in a similar or identical manner as that described and/or shown herein with respect to airway adapter 200.

Figure 5B:
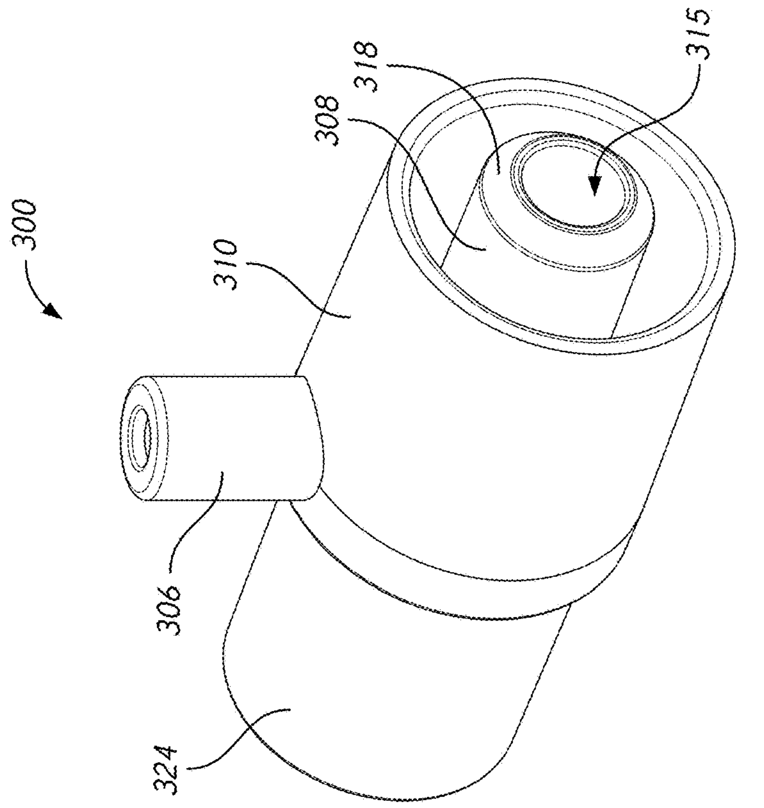
FIGS. 5A-5E illustrate perspective views of another embodiment of an airway adapter in accordance with aspects of this disclosure.
Figure 5A:
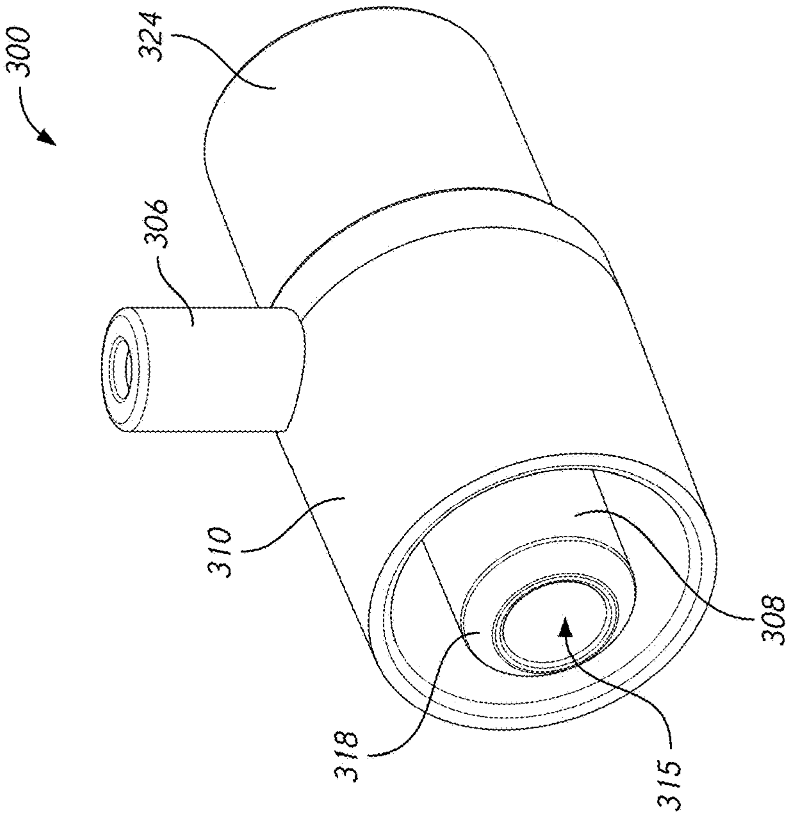
Figure 5D:
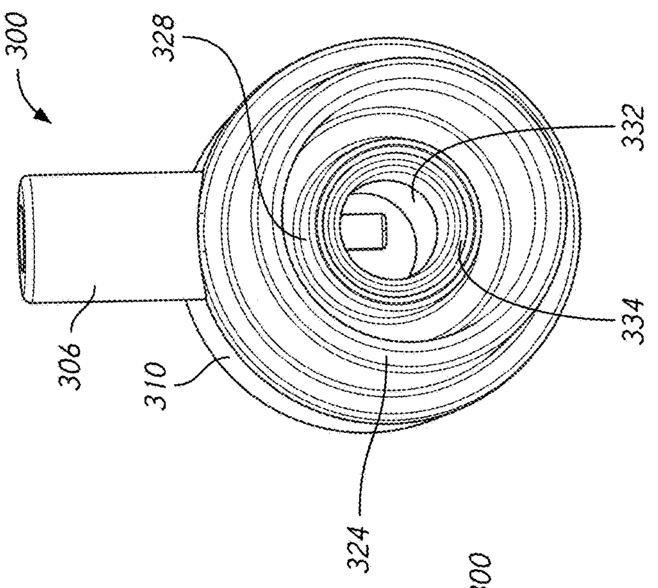
Figure 5E:
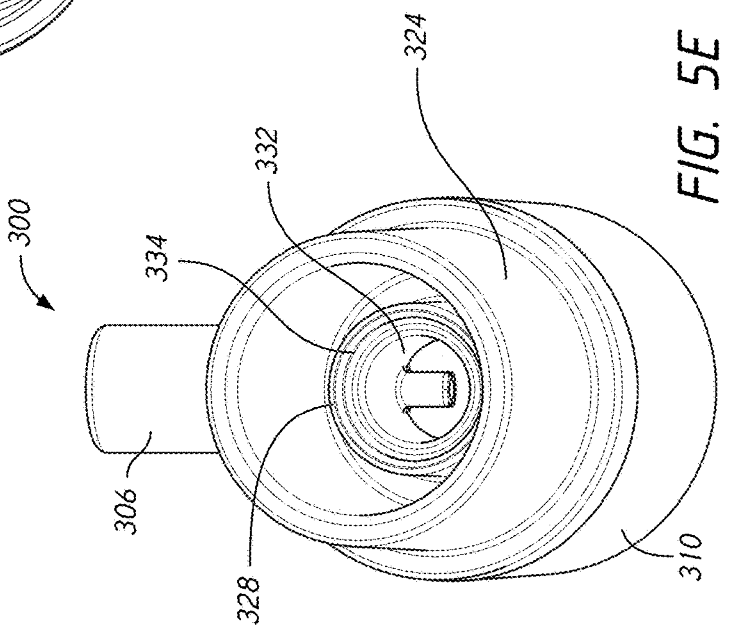
Figure 5C:
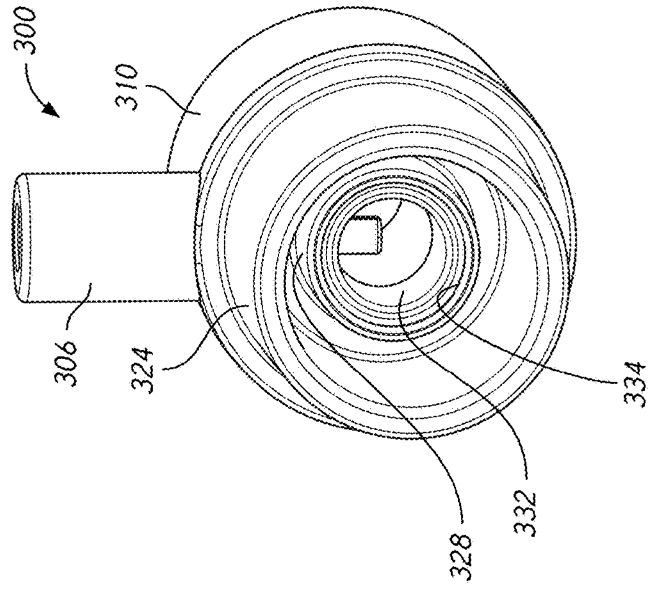
Figure 5G:
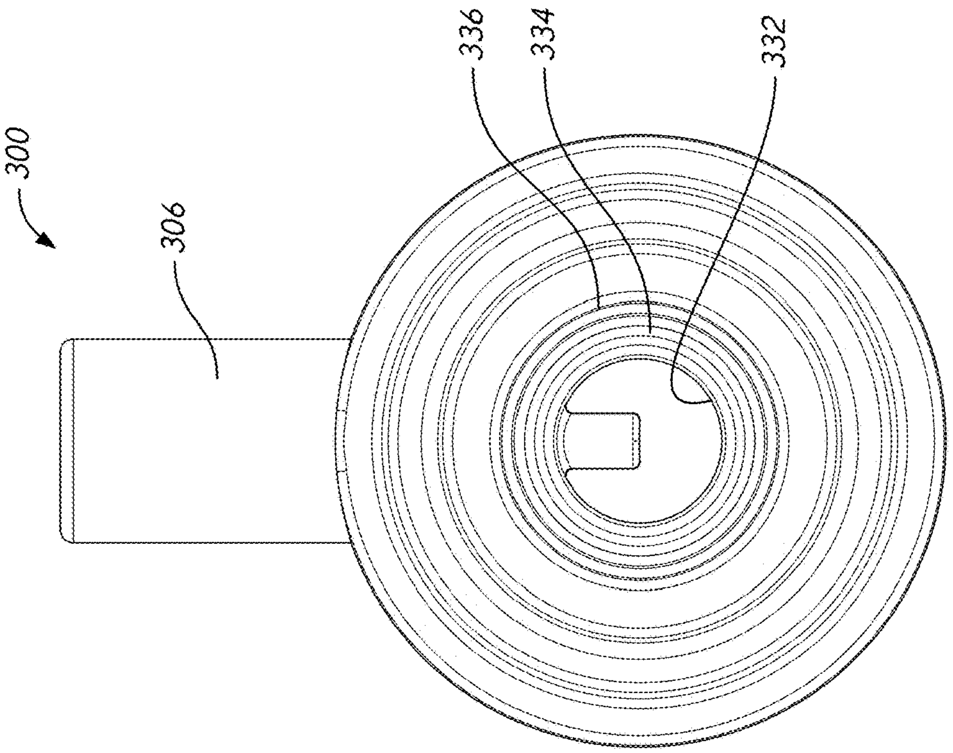
FIG. 5G illustrates a back view of the airway adapter of FIGS. 5A-5E in accordance with aspects of this disclosure.
Figure 5F:
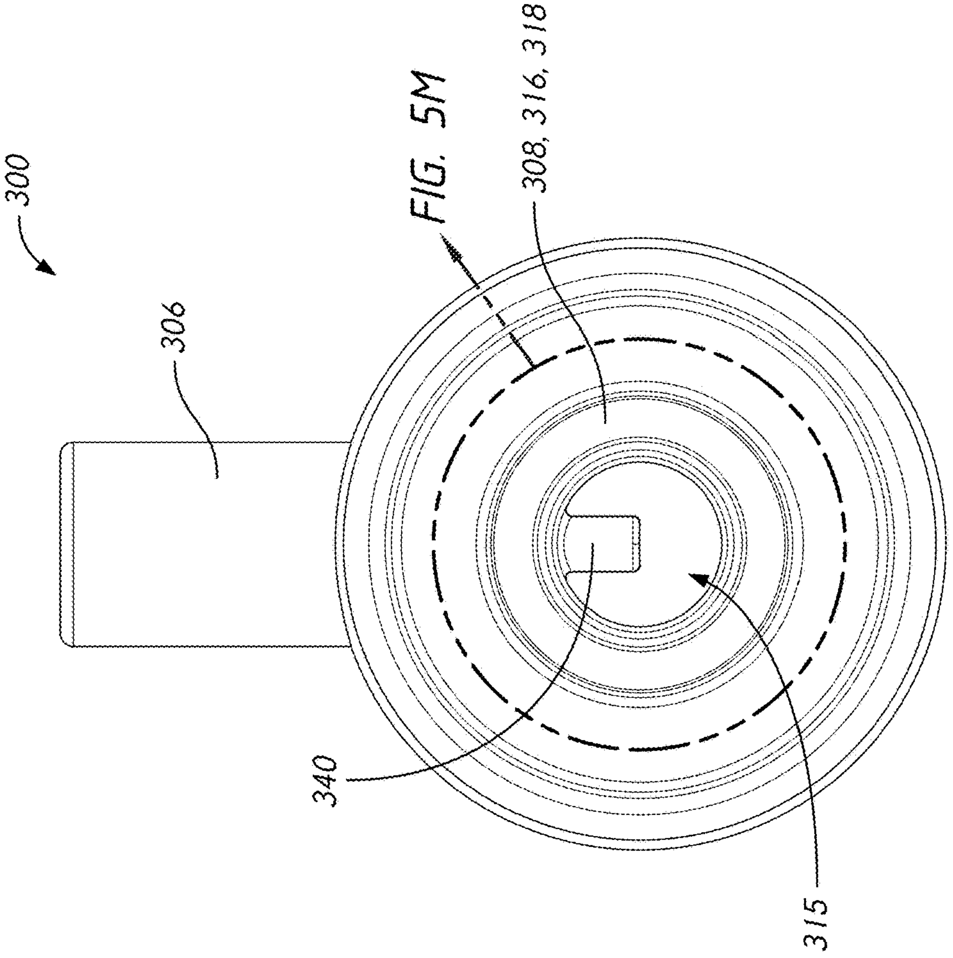
FIG. 5F illustrates a front view of the airway adapter of FIGS. 5A-5E in accordance with aspects of this disclosure.
Figure 5H:
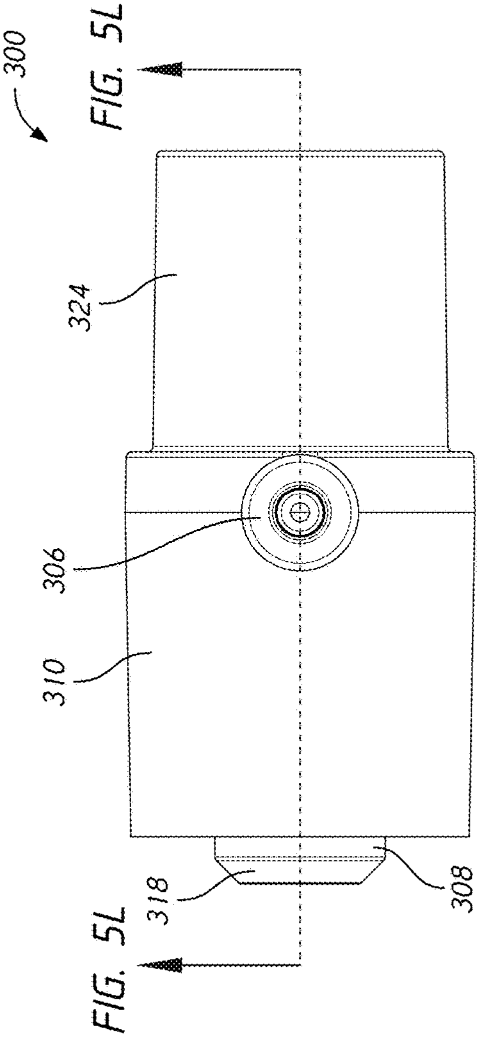
FIG. 5H illustrates a top view of the airway adapter of FIGS. 5A-5E in accordance with aspects of this disclosure.
Figure 5I:
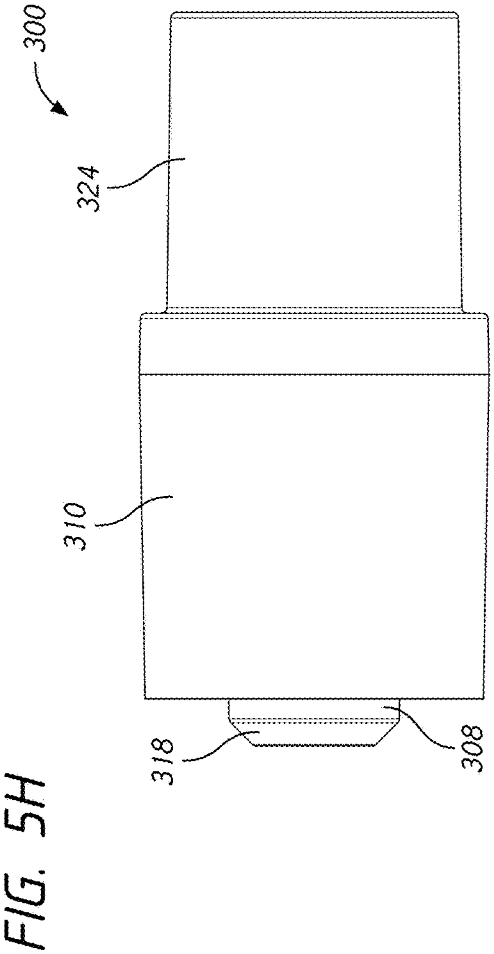
FIG. 5I illustrates a bottom view of the airway adapter of FIGS. 5A-5E in accordance with aspects of this disclosure.
Figure 5K:
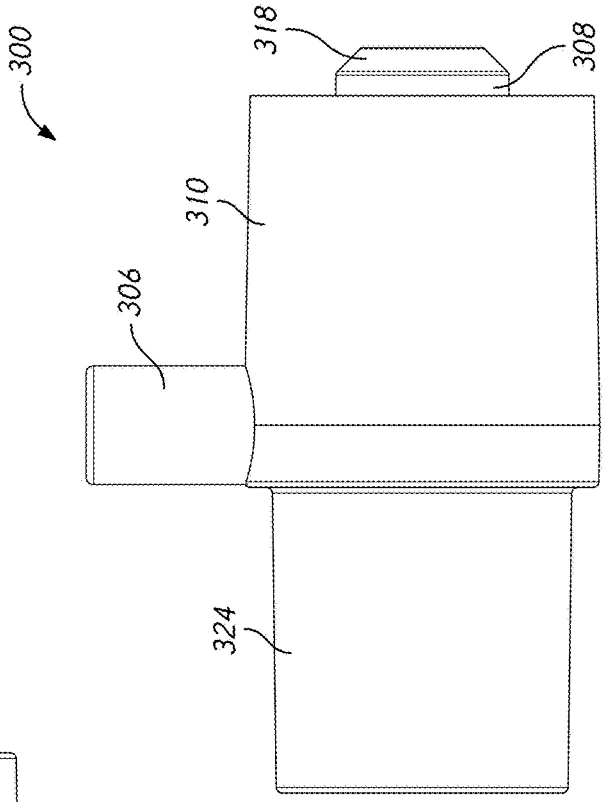
FIG. 5K illustrates another side view of the airway adapter of FIGS. 3A-3E in accordance with aspects of this disclosure.
Figure 5J:
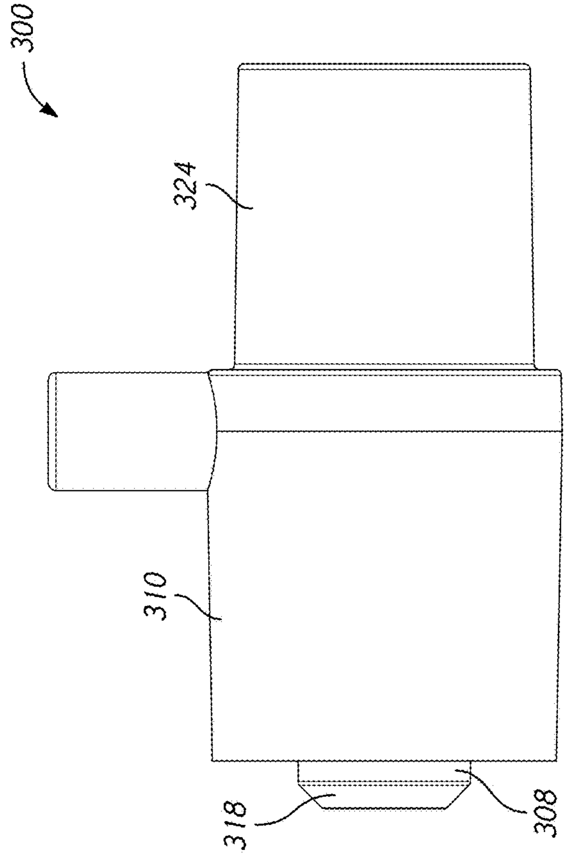
FIG. 5J illustrates a side view of the airway adapter of FIGS. 5A-5E in accordance with aspects of this disclosure.
Figure 5L:
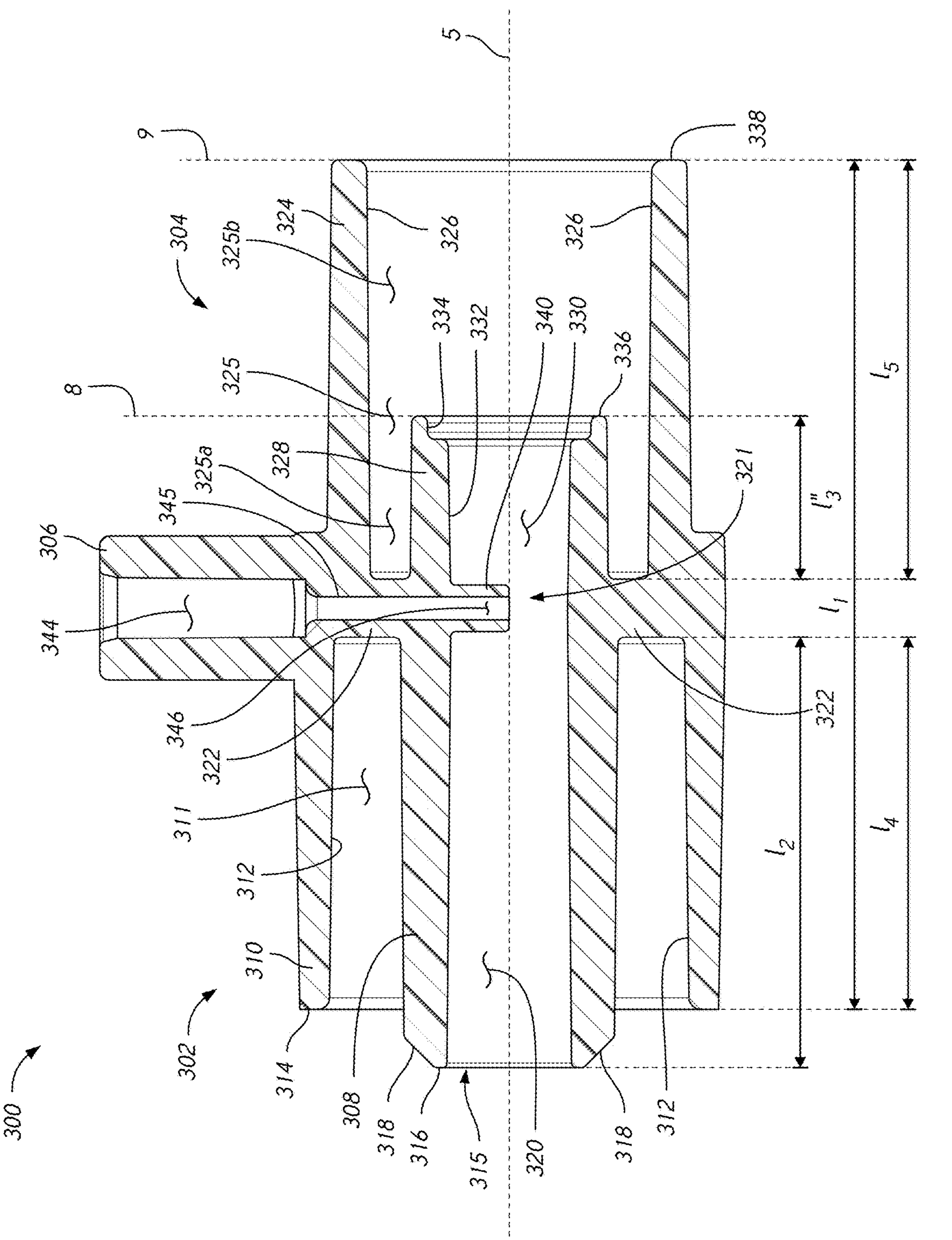
FIG. 5L illustrates a cross-sectional view taken through a portion of the airway adapter shown in FIG. 5H in accordance with aspects of this disclosure.

With reference to the cross-section of the airway adapter 300 illustrated in FIG. 5L, the outer wall 310 can define and/or include an internal cavity 311 (which can also be referred to as a "bore"), and the outer wall 324 can define and/or include an internal cavity 325 (which can also be referred to as a "bore"). The airway adapter 300 can include a barrier wall 322 that can partition (for example, separate) the internal cavities 311, 325 from one another. The barrier wall 322 can be positioned at or proximate to a region where the outer walls 310, 324 join (see FIG. 5L). Barrier wall 322 can include an opening 321 which can have a circular cross-section, among others (see FIG. 5L) which can be similar or identical to opening 221 of barrier wall 222 (see FIGS. 3L and 3M).

As shown through FIGS. 5A-5B and 5H-5L, airway adapter 300 can include an internal projection 308 (which can also be referred to as an "inner wall"). Internal projection 308 can be positioned at least partially within the internal cavity 311 and/or spaced from the outer wall 310. For example, internal projection 308 can be spaced from an inner surface 312 of the outer wall 310. Internal projection 308 can extend outward from the barrier wall 322 and can include and/or define a fluid passageway 320. Such fluid passageway 320 can be in fluid communication with at least a portion of the opening 321 (also referred to herein as "barrier wall opening") of the barrier wall 322. Internal projection 308 can extend around the opening 321 of the barrier wall 322. As illustrated in at least FIGS. 5A-5B, 5F, and 5L, internal projection 308 can include an opening 315 at a free (for example, "cantilevered") end 316 into the fluid passageway 320. Such free end 316 can be opposite another end of the internal projection 308 that is connected to the barrier wall 322.

In some configurations, airway adapter 300 can include an internal projection 328 (which can also be referred to as an "inner wall"). Internal projection 328 can be positioned within the internal cavity 325 and/or spaced from the outer wall 324. For example, internal projection 328 can be spaced from an inner surface 326 of the outer wall 324. Internal projection 328 can extend outward from the barrier wall 322 (for example, in an opposite direction as internal projection 308) and can include and/or define a fluid passageway 330. Such fluid passageway 330 can be in fluid communication with at least a portion of the opening 321 of the barrier wall 322 and the fluid passageway 320. Internal projection 328 can extend around the opening 321 of the barrier wall 322.

As mentioned previously, airway adapter 300 can include a port 306 which includes and/or defines a fluid passageway 344 (see FIG. 5L). Port 306 can extend away from outer surface of the outer wall 310 and/or outer wall 324 as discussed above and therefore can be referred to as an "external" port. Airway adapter 300 can additionally include a port 340. With reference to at least FIG. 5L, port 340 can extend from the barrier wall 322, for example, at and/or within the opening 321 and/or proximate a region where the internal projection 308 (and/or fluid passageway 320) meets the barrier wall 322 and/or the internal projection 328 (and/or fluid passageway 330). As such, port 340 can be referred to as an "internal" port. Port 340 can include and/or define a fluid passageway 346 which can be in fluid communication with the opening 321 of the barrier wall 322 and the fluid passageways 320, 330 of the internal projections 308, 328. The airway adapter 300 can include one or more channels defining one or more fluid passageways fluidly connecting fluid passageway 344 of port 306 and fluid passageway 346 of port 340. For example, airway adapter 300 can include a channel 345 extending through a portion of the barrier wall 322, outer wall 310, and/or outer wall 324 including and/or defining a fluid passageway which is in fluid communication with the fluid passageways 344, 346. In some configurations, the channel 345 and the port 340 can define a single fluid passageway (for example, fluid passageway 346) extending there through that is in fluid communication with the fluid passageway 344 and fluid passageways 320, 330, and/or opening 321. As mentioned previously, the airway adapter 300 can include a sampling portion that can allow and/or facilitate sampling of a portion of fluid flowing through the airway adapter 300 when in use and/or can facilitate determination of respiratory rate or another characteristic based upon, for example, fluid flowing into, out of, and/or through adapter 300. Port 306, fluid passageway 344, channel 345, fluid passageway 346, and/or port 340, can define or form such sampling portion of the airway adapter 200.

With reference to at least FIGS. 1C, 2C, and 5L, internal projection 308 can extend within the internal cavity 112 of the ET tube adapter 100 when the airway adapter 300 is coupled with the ET tube adapter 100 in a similar or identical manner as that discussed elsewhere herein with respect to internal projection 208 of airway adapter 200. In such configuration, the internal projection 308 can facilitate fluid communication between the ET tube 101 and ET tube connector 100 and fluid passageways 346, 344 of ports 340, 306, channel 345, and/or fluid passageways 320, 330. Internal projection 308 can have a first end connected to the barrier wall 322 and a second end 316 (which can also be referred to herein as a "free end" or "cantilevered end") opposite the first end. As illustrated in FIG. 5L, the second end 316 of the internal projection 308 can be positioned outside the outer wall 310 and/or internal cavity 311. For example, the internal projection 308 can have a length $l_2$ that is greater than a length $l_4$ of the outer wall 310 with reference to the barrier wall 322. In such configurations, end 316 of the internal projection 308 can be positioned closer to the opening 120 defined at the meeting region of the protrusion 102 (and fluid passageway 114) and the outer wall 106 (and internal cavity 112) when the airway adapter 300 is coupled to the ET tube adapter 100 (see FIG. 1B-1C). Such configurations can advantageously reduce internal void volumes ("dead space") that would otherwise be present when the airway adapter 300 is coupled with the ET tube connector 100 and ET tube 101.

Lengths $l_1$, $l_2$, $l_4$, and/or $l_5$ as illustrated in FIG. 5L of airway adapter 300 can be identical to lengths $l_1$, $l_2$, $l_4$, and/or $l_5$ (respectively) as illustrated and described elsewhere herein with respect to airway adapter 200 and/or 200'. A difference and/or ratio between length $l_2$ of the internal projection 308 and the length $l_4$ of outer wall 310 of airway adapter 300 can be similar or identical to the difference and/or ratio between length $l_2$ of the internal projection 208 and the length $l_4$ of outer wall 210 of airway adapter 200 discussed above.

Similar to that described above with reference to end 216 of internal projection 208 of airway adapter 200, end 316 of internal projection 308 of airway adapter 300 can be sized and/or shaped to allow the opening 315 and fluid passageway 320 to be positioned as close as possible to the opening 120 of the ET tube connector 100. For example, with reference to at least FIGS. 5A-5B and 5H-5L, end 316 of internal projection 308 can be chamfered, as illustrated by reference numeral 318. End 316 can be chamfered around all or a portion of the opening 315. For example, all or a portion of a perimeter of end 316 can be chamfered around opening 315. In some cases, an entire perimeter of end 316 can be chamfered around opening 315. In some cases, end 316 can be chamfered with a curved chamfer around all or a portion of the opening 315. Such curved chamfer is illustrated in at least FIGS. 5A-5B and 5H-5I. Similar to that described above with reference to airway adapter 200, providing all or a portion of end 316 of internal projection 308 with a chamfer (for example, curved chamfer) can advantageously facilitate mating and/or flush contact between inner surface 110 of ET tube adapter 100 (which can be frustoconical, for example) and end 316 around the opening 315. Such configurations can allow end 316 to get as close as possible to opening 120 and can minimize dead space within the internal cavity 112 that may otherwise exist if end 316 was positioned away from and/or not in such mating contact with inner surface 110.

The internal projection 308 can be rigid. For example, the internal projection 308 can be not compressible and/or not extendable. The internal projection 308 can be not compressible and/or not extendable relative to an axis extending through and/or along a length of the internal projection 308 and/or a length of the airway adapter 300 (for example, axis 5 illustrated in FIG. 5L). Such configuration can advantageously simplify manufacturing of the internal projection 308 alone or in combination with other components of the airway adapter 300, for example, where the internal projection 308 and/or airway adapter 300 is integrally formed (e.g., injection molded). Additionally, such configuration can advantageously ensure that the internal projection 308 (for example, end 316 and/or chamfered region 318) contacts an inner surface of the ET tube adapter 100 (such as inner surface 110) in a consistent manner when the airway adapter 300 is in use. The internal projection 308 can be integrally formed with any or all other portions of the airway adapter 300. For example, the internal projection 308 can be integrally formed with the outer wall 310, barrier wall 322, outer wall 324, internal projection 328, port 340, and/or port 306. Any or all of other components of the airway adapter 300 can be rigid in a similar manner as that discussed above with reference to internal projection 308. For example, any or all of the outer wall 310, barrier wall 322, outer wall 324, internal projection 328, port 340, and/or port 306 can be rigid. The internal projection 328 can be not compressible and/or not extendable. The internal projection 328 can be not compressible and/or not extendable relative to an axis extending through and/or along a length of the internal projection 328 and/or a length of the airway adapter 300 (for example, axis 5).

With reference to FIG. 5L, where end 316 comprises a chamfered region or surface 318, such chamfered region or surface 318 can be chamfered at an angle relative to a plane or axis defined along end 316 (which can be similar or identical to axis 6 described and shown elsewhere herein) that is identical to angle $\theta_1$ described above with reference to chamfered region or surface 218 of end 216 of airway adapter 200. Additionally or alternatively, such chamfered region or surface 318 can be chamfered at an angle relative to a plane or axis defined along a surface of the internal projection 308 (which can be similar or identical to axis 7 described and shown elsewhere herein) at an angle that is identical angle $\theta_2$ described above with reference to chamfered region or surface 218 of end 216 of airway adapter 200.

Figure 5M:
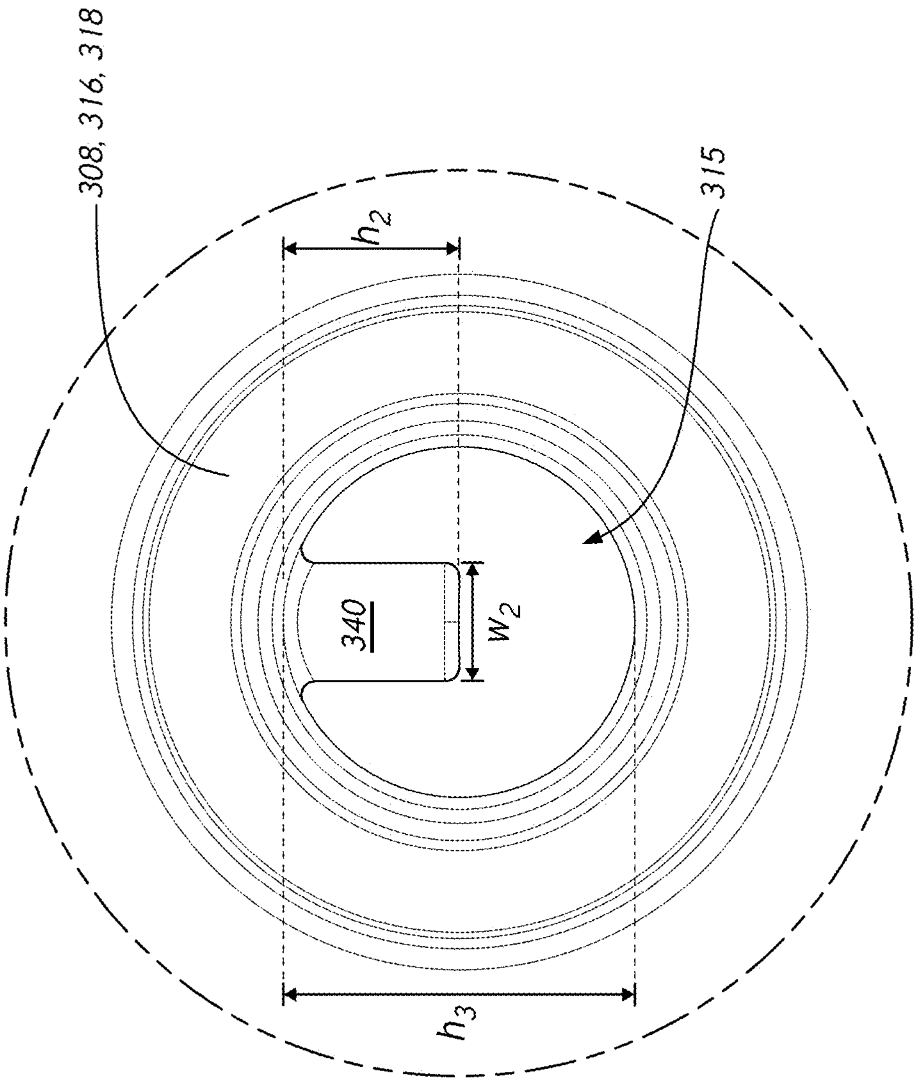
FIG. 5M illustrates an enlarged view of a portion of the airway adapter shown in FIG. 5F in accordance with aspects of this disclosure.

As shown, internal projection 308 can comprise a cylindrical shape. For example, end 316 of internal projection 308 and/or a cross-section of internal projection 308 can comprise a circular shape. End 316 can comprise a curved chamfer around all or a portion of the end 316. Additionally or alternatively, opening 315 can comprise a circular shape. As discussed elsewhere herein, opening 315 can be in fluid communication with fluid passageway 320, which allows fluid (for example, gas) to flow into and/or out of the fluid passageway 320. With reference to FIG. 5M, opening 315 can have a height $h_3$ (for example, a diameter). $H_3$ can be between approximately 0.05 inch and approximately 1 inch, for example, between approximately 0.06 inch and approximately 0.9 inch, between approximately 0.07 inch and approximately 0.8 inch, between approximately 0.08 inch and approximately 0.7 inch, between approximately 0.09 inch and approximately 0.6 inch, between approximately 0.1 inch and approximately 0.5 inch, between approximately 0.2 inch and approximately 0.4 inch, or between approximately 0.1 inch and approximately 0.3 inch, or any value or range between any of these values or ranges or any value or range bounded by any combination of these values, although values or ranges outside these values or ranges can be used in some cases. As illustrated, port 340 can have a height $h_2$ that is identical to that which is described above with reference to port 240 of airway adapter 200. Additionally or alternatively, port 340 can have a width $w_2$ that is identical to that which is described above with reference to port 240 of airway adapter 200.

In some configurations, $h_3$ of opening 315 is equal to approximately twice the height $h_2$ of port 340. In some cases, $h_2$ of port 340 is approximately half of height $h_3$ of opening 215. In some cases, $h_2$ of port 340 is less than or greater to half of height $h_3$ of opening 215. A ratio between height $h_3$ of opening 315 and height $h_2$ of port 340 can be identical to any of the ratios between height $h_1$ of opening 215 and height $h_2$ or port 240 discussed above with reference to FIG. 3N. With reference to FIG. 5L, in some cases the port 340 extends from the barrier wall 322 to a longitudinal axis 5 extending through a center of the internal projection 320 and/or internal projection 328.

A ratio between a diameter or height $h_3$ of opening 315 and width $w_2$ of port can be between approximately 1 and approximately 5, for example, between approximately 1.5 and approximately 4.5, between approximately 2 and approximately 4, between approximately 2.5 and approximately 3, between approximately 3 and approximately 4, between approximately 2 and approximately 5, or between approximately 3 and approximately 4, or any value or range between any of these values or ranges, or any value or range bounded by any combination of these values, although values or ranges outside these values or ranges can be used in some cases.

As discussed previously, the airway adapter 300 can include an internal projection 328 that can be positioned at least partially within the internal cavity 325 and/or spaced from the outer wall 324 (for example, spaced from an inner surface 326 of the outer wall 324). As also discussed previously, internal projection 328 can extend outward from the barrier wall 322 (for example, in an opposite direction as internal projection 308) and can include and/or define a fluid passageway 330. Such fluid passageway 330 can be in fluid communication with at least a portion of the opening 321 of the barrier wall 322, fluid passageway 320 of internal projection 308, fluid passageway 346, channel 345, and/or fluid passageway 344. Internal projection 328 can advantageously reduce dead space that may otherwise exist when airway adapter 300 is connected to flow sensor 30 or 50 or a ventilation tube connector 40. For example, internal projection 328 can extend from barrier wall 322 and be positioned at or proximate to a projection 36, 56 of flow sensor 30, 50 when airway adapter 300 is coupled thereto (see FIGS. 5L, 1C, and 2C). Accordingly, internal projection 328 can reduce or eliminate an internal void volume that may otherwise include the volume within the internal cavity 325 of outer wall 324 (or a portion thereof).

With reference to FIG. 5L, the internal projection 328 can have a length $l_3''$. Length $l_3''$ can be between approximately 0.05 inch and approximately 1 inch, for example, between approximately 0.06 inch and approximately 0.9 inch, between approximately 0.07 inch and approximately 0.8 inch, between approximately 0.08 inch and approximately 0.7 inch, between approximately 0.09 inch and approximately 0.6 inch, between approximately 0.1 inch and approximately 0.5 inch, between approximately 0.2 inch and approximately 0.4 inch, between approximately 0.3 inch and approximately 0.4 inch, or between approximately 0.2 inch and approximately 0.3 inch, or any value or range between any of these values or ranges or any value or range bounded by any combination of these values, although values or ranges outside these values or ranges can be used in some cases.

With reference to FIG. 5L, length $l_5$, which is defined between the barrier wall 322 and an end 338 (for example, a “free” end) of the outer wall 324 can be identical to length $l_5$ (respectively) as illustrated and described elsewhere herein with respect to airway adapter 200 and/or 200'. Length $l_3''$ can be smaller than length $l_5$. A difference between the length $l_3''$ of the internal projection 328 and the length $l_5$ can be at least 0.05 inch, at least 0.06 inch, at least 0.07 inch, at least 0.08 inch, at least 0.09 inch, at least 0.1 inch, at least 0.2 inch, at least 0.3 inch, at least 0.4 inch, or at least 0.5 inch, or any value therebetween, although values outside these values or ranges can be used in some cases. A ratio between the length $l_5$ and the length $l_3''$ can be between approximately 1 and approximately 5, for example, between approximately 1.1 and approximately 4.9, between approximately 1.2 and approximately 4.8, between approximately 1.3 and approximately 4.7, between approximately 1.4 and approximately 4.6, between approximately 1.5 and approximately 4.5, between approximately 1.6 and approximately 4.4, between approximately 1.7 and approximately 4.3, between approximately 1.8 and approximately 4.2, between approximately 1.9 and approximately 4.1, between approximately 2 and approximately 4, between approximately 2.1 and approximately 3.9, between approximately 2.2 and approximately 3.8, between approximately 2.3 and approximately 3.7, between approximately 2.4 and approximately 3.6, between approximately 2.5 and approximately 3.5, between approximately 2.6 and approximately 3.4, between approximately 2.7 and approximately 3.3, between approximately 2.8 and approximately 3.2, between approximately 2.9 and approximately 3.1, between approximately 2 and approximately 2.5, or between approximately 2.2 and approximately 2.3, although values or ranges outside these values or ranges can be used in some cases. A ratio between the length $l_5$ and the length $l_3''$ can be at least approximately 1.1, at least approximately 1.2, at least approximately 1.3, at least approximately 1.4, at least approximately 1.5, at least approximately 1.6, at least approximately 1.7, at least approximately 1.8, at least approximately 1.9, at least approximately 2, at least approximately 2.1, at least approximately 2.2, at least approximately 2.3, at least approximately 2.4, at least approximately 2.5, at least approximately 2.6, at least approximately 2.7, at least approximately 2.8, at least approximately 3, at least approximately 3.1, at least approximately 3.2, at least approximately 3.3, at least approximately 3.4, at least approximately 3.5, at least approximately 3.6, at least approximately 3.7, at least approximately 3.8, at least approximately 3.9, or at least approximately 4, although values or ranges outside these values or ranges can be used in some cases.

With continued reference to FIG. 5L, length $l_2$ of the internal projection 308 can be greater than length $l_3$" of the internal projection 328. For example, length $l_2$ can be greater than length $l_3$" by at least approximately 0.1 inch, at least approximately 0.2 inch, at least approximately 0.3 inch, at least approximately 0.4 inch, at least approximately 0.5 inch, at least approximately 0.6 inch, at least approximately 0.7 inch, at least approximately 0.8 inch, at least approximately 0.9 inch, or at least approximately 1 inch, although values or ranges outside these values or ranges can be used in some cases. A ratio between length $l_2$ and length $l_3$" can be between approximately 1 and approximately 5, for example, between approximately 1.5 and approximately 4.5, between approximately 2 and approximately 4, between approximately 2.5 and approximately 3.5, between approximately 2 and approximately 3, or between approximately 2.5 and approximately 3, or any value or range between any of these values or ranges or any value or range bounded by any combination of these values, although values or ranges outside these values or ranges can be used in some cases.

In some configurations, the internal projection 328 is configured to secure to a portion of a flow sensor. For example, the internal projection 328 can be configured to secure to a protrusion 51 of flow sensor 50 which can define and/or form part of a fluid passageway 58 extending through the flow sensor 50. Where protrusion 51 is a wall that splits a fluid passageway extending through internal projection 56 of flow sensor 50, internal projection 328 can receive and secure to protrusion 51. With reference to FIG. 5L, the internal projection 328 can include an internal cavity defining the fluid passageway 330 which has a first portion 332 and a second portion 334. The first portion 332 of the internal cavity of the internal projection 328 can comprise a smaller cross-sectional area than the second portion 334. The second portion 334 can also be referred to as a "recessed portion." The second portion 334 can be sized and/or shaped to receive and secure the protrusion 51 of the flow sensor 50. In some embodiments, this configuration can significantly reduce dead space in the airway adapter 300 by entirely or partially "closing off" the internal cavity 325 of the outer wall 324 in and around an end 336 (also referred to as a "free end") of the internal projection 328. The cross-sections of the first and second portions 332, 334 can be circular, as illustrated in at least FIGS. 5C-5E, among other shapes.

With reference to FIG. 5L, the first portion 332 can comprise a greater proportion or percentage of the length $l_3$ of the internal projection 328 than the second portion 334. Alternatively, the first portion 332 can comprise an equal or smaller proportion or percentage of the length $l_3$ of the internal projection 328 than the second portion 334.

With reference to FIG. 5L, the airway adapter 300 can include a first portion 302 that can be coupled to the ET tube adapter 100 and a second portion 304 that can be coupled to the flow sensor 30, 50 or the ventilation tube connector 40. In some cases, the first portion 302 can include or be defined by the outer wall 310 and/or the internal projection 308. In some cases, the second portion 304 can include or be defined by the outer wall 324 and/or the internal projection 328.

As discussed above, the airway adapter 300 can include low dead space in comparison to conventional airway adapters, alone and/or when connected or assembled with other components in a ventilation assembly (such as a ventilation assembly similar to ventilation assembly 10, 10'). In some configurations, a total dead space of the airway adapter 300 is less than approximately 2.5 ml, less than approximately 2.4 ml, less than approximately 2.3 ml, less than approximately 2.2 ml, less than approximately 2.1 ml, less than approximately 2 ml, or less than approximately 1.9 ml.

With reference to FIG. 5L, a total interior volume (which may also be referred to as "interior void volume" or "dead space") of the fluid passageway 320, opening 321, fluid passageway 330, and/or the internal cavity 325 (or a portion thereof) may be less than approximately 2.5 ml. Such interior volume can include fluid passageway 320, opening 321, fluid passageway 330, and a portion of the internal cavity 325, for example, a portion of the internal cavity 325 between the free end 336 of the internal projection 328 and the free end 338 of the outer wall 324. A first plane 8 defined along the free end 336 can partition the internal cavity 325 into a first portion 325*a* defined between such first plane 8 and the barrier wall 322 and a second portion 325*b* defined between such first plane 8 and a second plane 9 along the free end 338 of the outer wall 324. Such "first" and "second" planes 8, 9 are illustrated as vertically oriented given the view shown in FIG. 5L. In some configurations, a total interior volume of the first fluid passageway 320, opening 321, second fluid passageway 330 (which can be defined by different sized portions 332, 334 as discussed elsewhere herein), and/or second portion 325*b* is less than approximately 3 ml, less than approximately 2.9 ml, less than approximately 2.8 ml, less than approximately 2.7 ml, less than approximately 2.6 ml, less than approximately 2.5 ml, less than approximately 2.4 ml, less than approximately 2.3 ml, less than approximately 2.2 ml, less than approximately 2.1 ml, less than approximately 2 ml, or less than approximately 1.9 ml.

With reference to FIGS. 1C, 2C, and 5L, a total interior volume (which may also be referred to as "interior void volume" or "dead space") of the airway adapter 300 and ET tube adapter 100 when coupled with one another can be less than approximately 2 ml, less than approximately 1.9 ml, less than approximately 1.8 ml, less than approximately 1.7 ml, less than approximately 1.6 ml, or less than approximately 1.5 ml. For example, with reference to FIGS. 1C, 2C, and 5L, a total interior volume of the first fluid passageway 320, opening 321, second fluid passageway 330 (which can be defined by different sized portions 332, 343 in some configurations), second portion 325*b*, and a portion of the internal cavity 112 defined between an end 316 of internal projection 308 and the opening 120 of ET tube adapter 100 (see "112*a*" in FIGS. 1C, 2C) can be less than approximately 2 ml, less than approximately 1.9 ml, less than approximately 1.8 ml, less than approximately 1.7 ml, less than approximately 1.6 ml, or less than approximately 1.5 ml. As another example, the total interior volume of the airway adapter 300 and ET tube adapter 100 when coupled with one another can be between approximately 1 ml and approximately 2 ml, for example, between approximately 1.1 ml and approximately 1.9 ml, between approximately 1.2 ml and approximately 1.8 ml, between approximately 1.3 ml and approximately 1.7 ml, between approximately 1.4 ml and approximately 1.6 ml, between approximately 1.5 ml and approximately 2 ml, or between 1.7 ml and 1.9 ml.

FIG. 6A-6I illustrate another embodiment of an airway adapter 300'. Airway adapter 300' can be similar or identical to airway adapter 300 in many respects. For example, with reference to FIGS. 6A-6I, airway adapter 300' can include a first portion 302', a second portion 304', a first outer wall 310' having an end 314', a second outer wall 324' having an end 338', an internal projection 308' having an end 316', an opening 315', a chamfered region or surface 318' on end 316', an internal projection 328' having an end 336', a port 306', a port 340', fluid passageways 344', 346', a channel 345', an internal cavity 311' within outer wall 310', an inner surface 312', a fluid passageway 320' extending through internal projection 308', a barrier wall 322', an opening 321' in the barrier wall 322', an internal cavity 325' within outer wall 324', an inner surface 326', a fluid passageway 330' extending through internal projection 328' which includes first and second portions 332', 334', which can be similar or identical in some or many respects to first portion 302, second portion 304, outer wall 310, end 314, outer wall 324, end 338, internal projection 308, end 316, opening 315, chamfered region or surface 318, end 316, internal projection 328, end 336, port 306, port 340, fluid passageways 344, 346, channel 345, internal cavity 311 within outer wall 310, inner surface 312, fluid passageway 320 extending through internal projection 308, barrier wall 322, opening 321 in the barrier wall 322, internal cavity 325 within outer wall 324, inner surface 326, and fluid passageway 330 extending through internal projection 328 which includes first and second portions 332', 334', respectively.

Similar to internal projection 328 of airway adapter 300, internal projection 328' of airway adapter 300' can include an internal cavity defining a fluid passageway 330' which has a first portion 332' and a second portion 334' (which also may be referred to as a "recessed portion"). Similar to internal projection 328, first portion 332' can comprise a smaller cross-sectional area than second portion 334', and second portion 334' can be sized and/or shaped to receive and secure the protrusion 51 of the flow sensor 50. As can be seen by comparison of FIGS. 5L and 6I, first portion 332' comprises a smaller portion of the internal cavity of internal projection 328' than first portion 332 of the internal cavity of internal projection 328. Additionally, by consequence, second portion 334' comprises a larger portion of the internal cavity of internal projection 328' than second portion 334 of the internal cavity of internal projection 328. In some implementations, first portion 332' comprises a larger portion of the internal cavity of internal projection 328' than the second portion 334'.

Airway adapter 300' can be coupled with an ET tube, for example, via an ET tube adapter coupled to the ET tube, in a variety of ways. For example, airway adapter 300' can be coupled with ET tube adapter 100 in a similar or identical manner as that described and/or shown herein with respect to airway adapter 200. Additionally or alternatively, airway adapter 300' can be coupled with a flow sensor (such as flow sensor 30 and/or flow sensor 50) in a variety of ways, such as that described and/or shown herein with respect to airway adapter 200. Further, airway adapter 300' can be utilized with either or both of ventilation assemblies 10, 10' in a similar or identical manner as described and/or shown with respect to airway adapter 200.

Aspects of airway adapter 300' can be incorporated into airway adapter 300. By way of non-limiting example, airway adapter 300 can include internal projection 328' (discussed above with reference to FIG. 3) instead of internal projection 328. [0148] With reference to FIG. 6I, airway adapter 300 has a length $l_1$, internal projection has a length $l_2$, internal projection 328' has a length $l_3''$, outer wall 310' has a length $l_4$, and outer wall 324' has a length $l_5$, the values of which can be that described above with respect to airway adapter 300. In some embodiments, outer wall 310' comprises a smaller portion of length $l_1$ in relation to outer wall 324'.

Figure 6A:
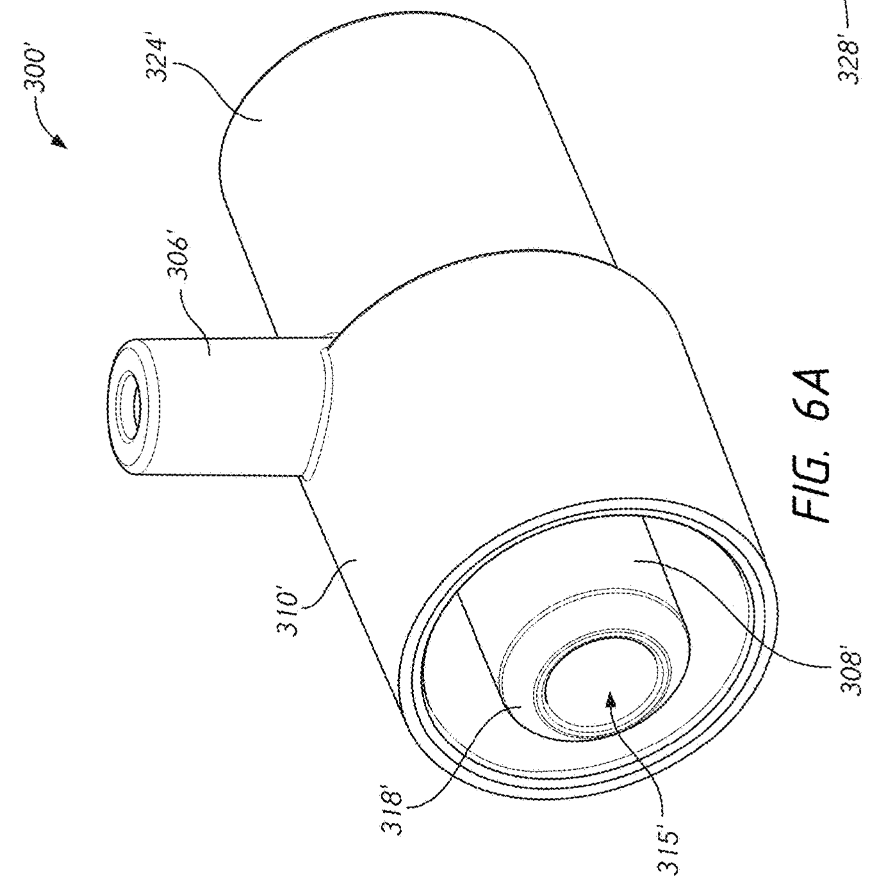
FIGS. 6A-6B illustrate perspective views of another embodiment of an airway adapter in accordance with aspects of this disclosure.
Figure 6B:
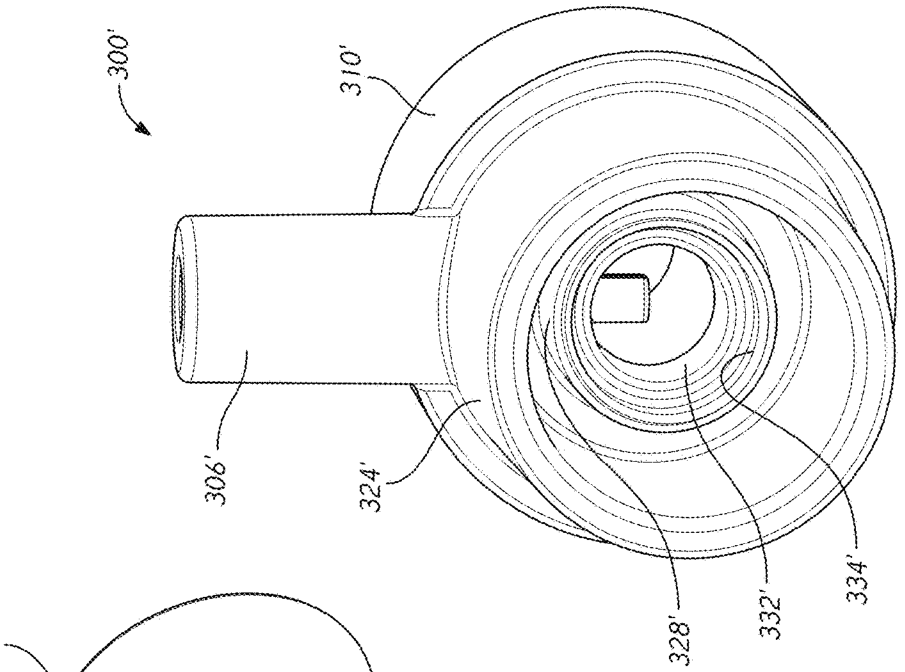
Figure 6D:
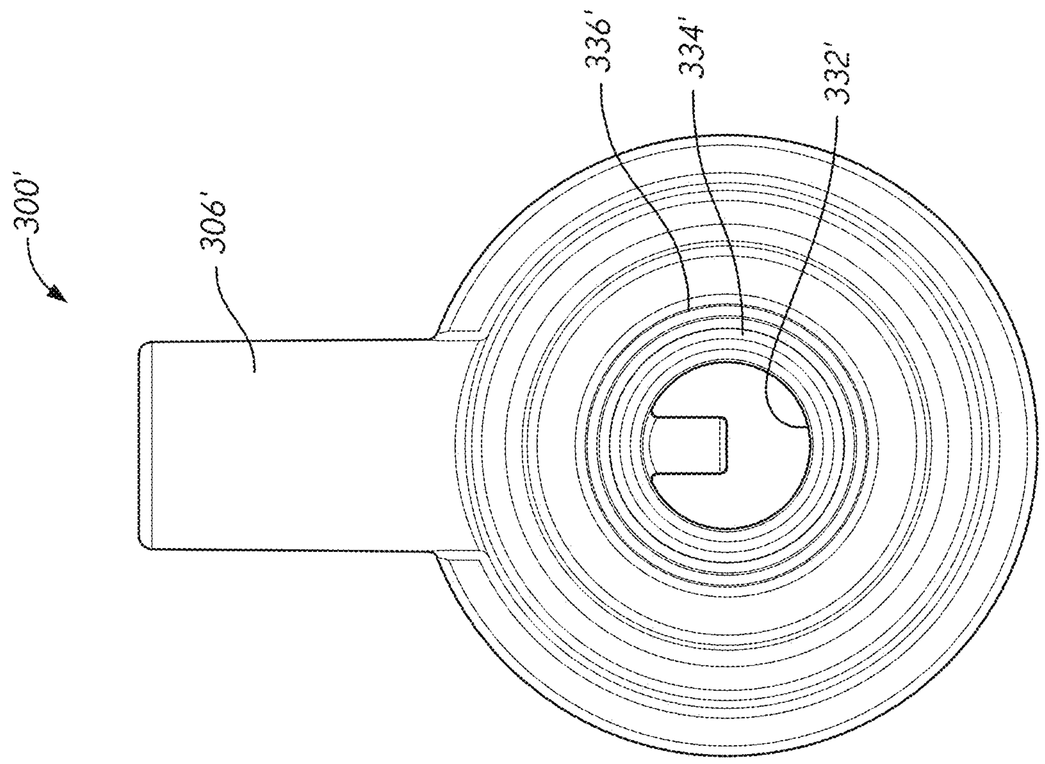
FIG. 6D illustrates a back view of the airway adapter of FIGS. 6A-6B in accordance with aspects of this disclosure.
Figure 6C:
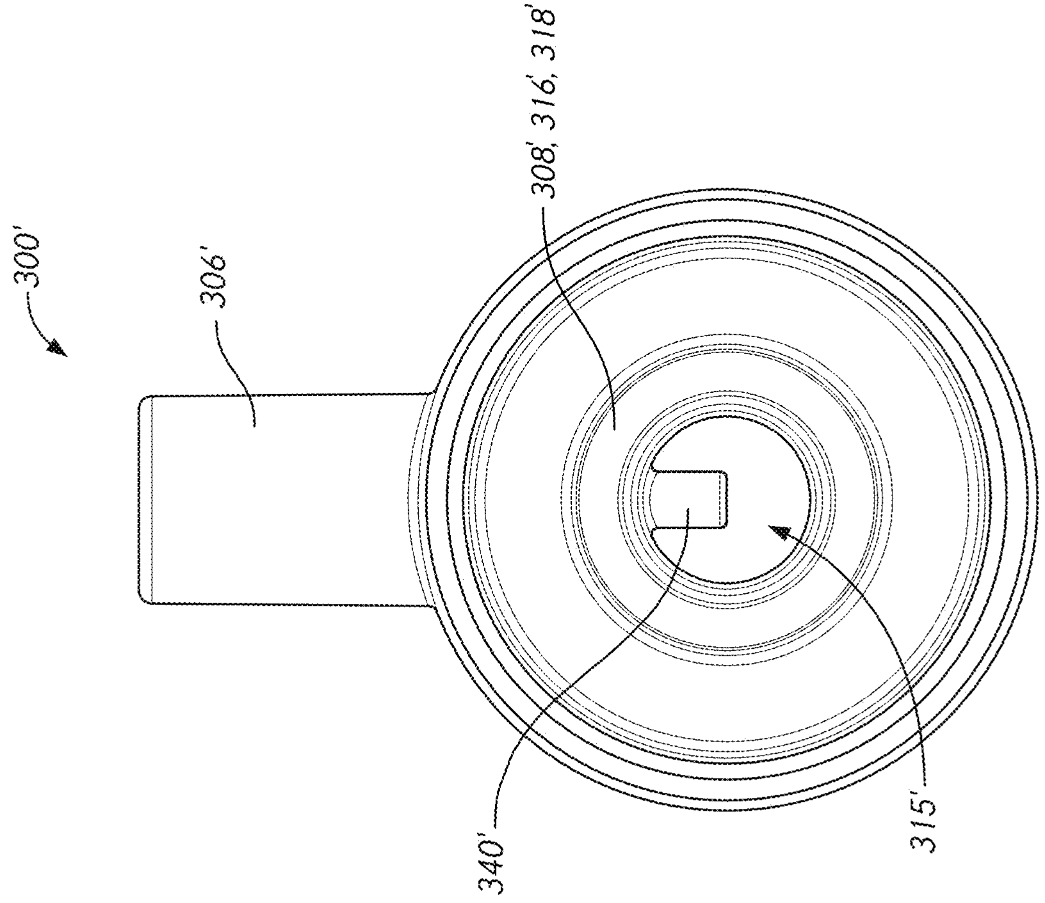
FIG. 6C illustrates a front view of the airway adapter of FIGS. 6A-6B in accordance with aspects of this disclosure.
Figure 6E:
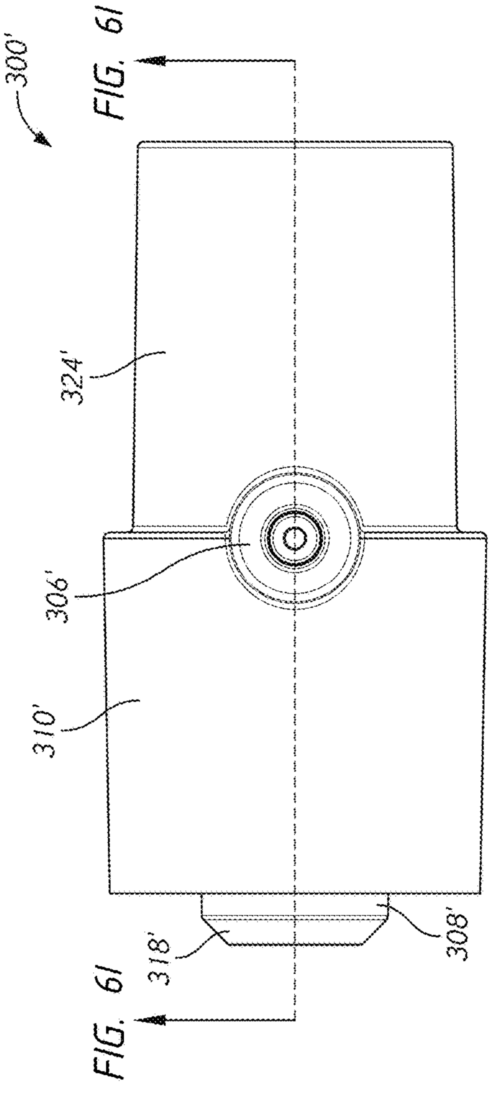
FIG. 6E illustrates a top view of the airway adapter of FIGS. 6A-6B in accordance with aspects of this disclosure.
Figure 6F:
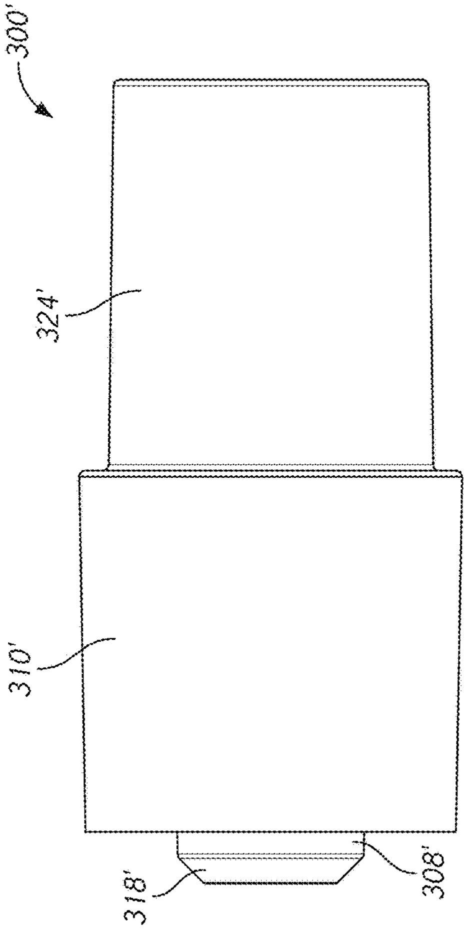
FIG. 6F illustrates a bottom view of the airway adapter of FIGS. 6A-6B in accordance with aspects of this disclosure.
Figure 6G:
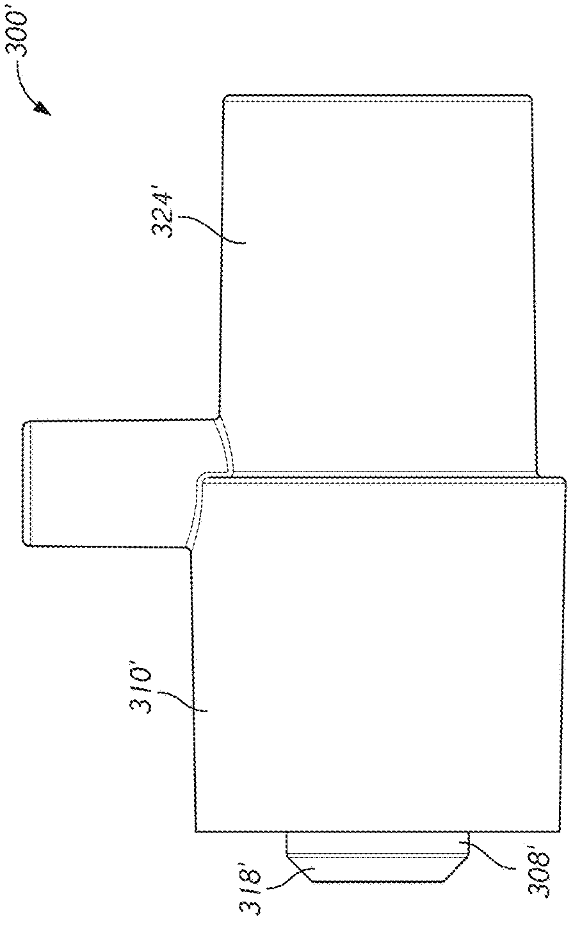
FIG. 6G illustrates a side view of the airway adapter of FIGS. 6A-6B in accordance with aspects of this disclosure.
Figure 6H:
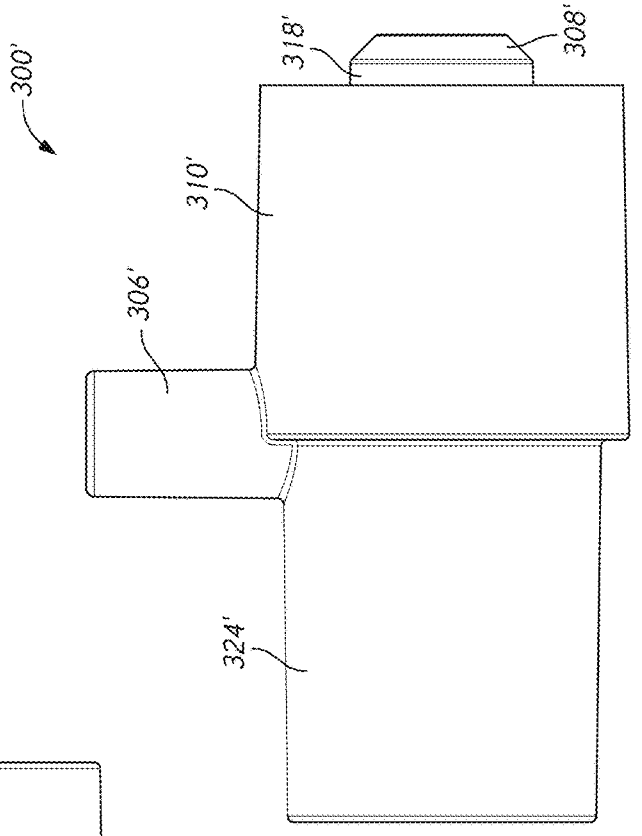
FIG. 6H illustrates another side view of the airway adapter of FIGS. 5A-5E in accordance with aspects of this disclosure.
Figure 6I:
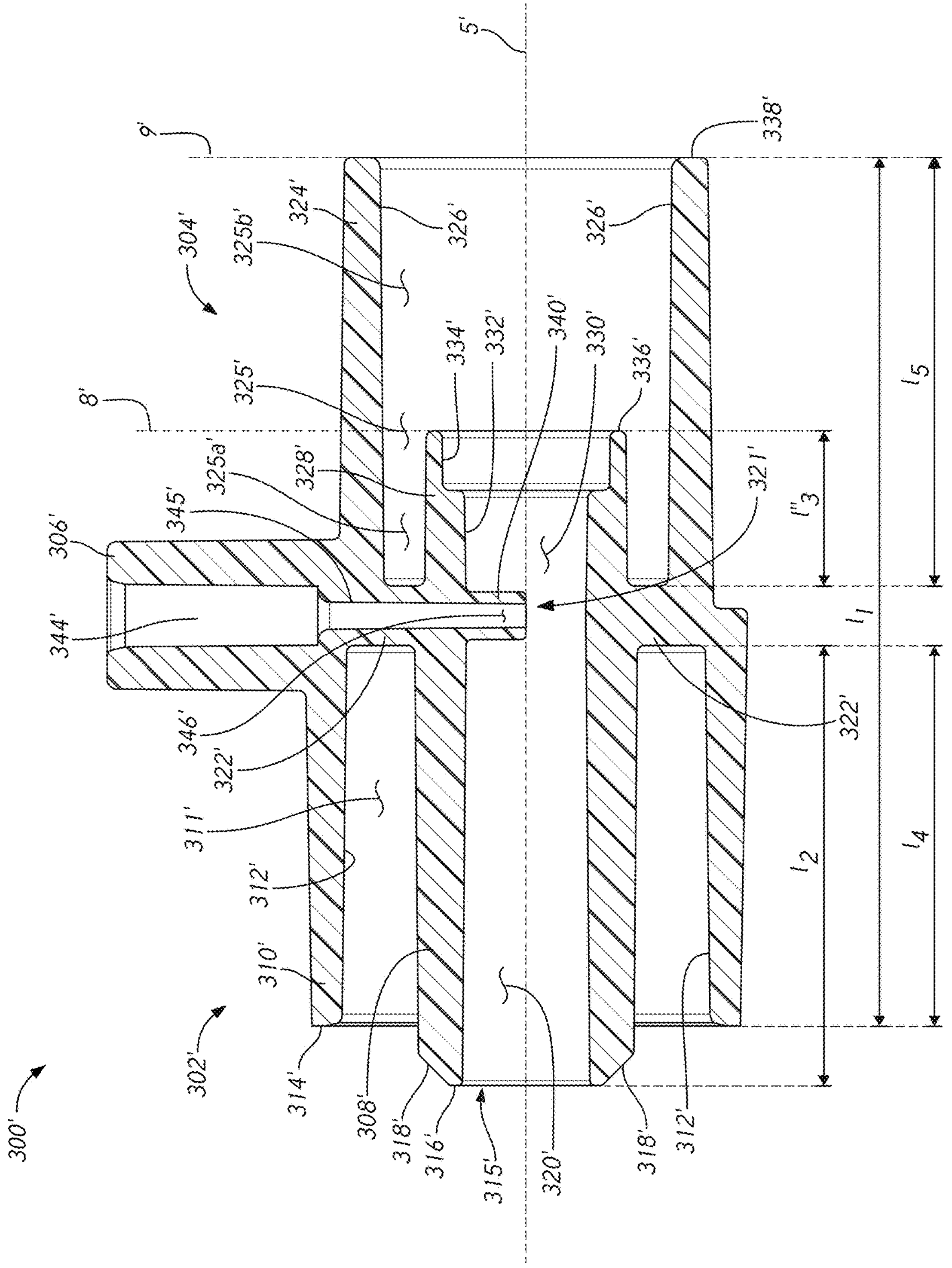
FIG. 6I illustrates a cross-sectional view taken through a portion of the airway adapter shown in FIG. 6E in accordance with aspects of this disclosure.

With reference to FIG. 6I, where end 316' comprises a chamfered region or surface 318', such chamfered region or surface 318' can be chamfered at an angle relative to a plane or axis extending along end 316' (for example, similar or identical to axis or plane 6 described with respect to FIG. 3O) similar or identical to as described above with respect to angle $\theta_1$. Additionally or alternatively, such chamfered region or surface 318' can be chamfered at an angle relative to a plane or axis extending along a surface of the internal projection 308' (for example, similar or identical to axis or plane 7 described with respect to FIG. 3O) similar or identical to as described above with respect to angle $\theta_2$. FIG. 6I illustrates a longitudinal axis 5' that can extend through a center of airway adapter 300', such as though a center of outer walls 310', 324', and internal projections 308', 328'. FIG. 6I also illustrates a first plane 8' defined along the free end 336' which can partition the internal cavity 325' within outer wall 324' into a first portion **325*a*' defined between such first plane 8' and the barrier wall 322' and a second portion 325*b*' defined between such first plane 8' and a second plane 9' along the free end 338' of the outer wall 324'. Such "first" and "second" planes 8', 9' are illustrated as vertically oriented given the view shown in FIG. 6**I.

Additional Considerations and Terminology

Although this disclosure has been described in the context of certain examples, it will be understood by those skilled in the art that the present disclosure extends beyond the specifically disclosed examples to other alternative examples and/or uses of the disclosure and obvious modifications and equivalents thereof. In addition, while a number of variations of the disclosure have been shown and described in detail, other modifications, which are within the scope of this disclosure, will be readily apparent to those of skill in the art based upon this disclosure. It is also contemplated that various combinations or sub-combinations of the specific features and aspects of the examples may be made and still fall within the scope of the disclosure. Accordingly, it should be understood that various features and aspects of the disclosure can be combined with or substituted for one another in order to form varying modes of the disclosed.

Features, materials, characteristics, or groups described in conjunction with a particular aspect, or example are to be understood to be applicable to any other aspect, or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing examples of devices or systems. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that the actual steps taken in the processes illustrated and/or disclosed may differ from those shown in the figures. Depending on the system, certain of the steps described above may be removed, others may be added. Furthermore, the features and attributes of the specific examples disclosed above may be combined in different ways to form additional examples of systems, all of which fall within the scope of the present disclosure. Also, the separation of various system components in the implementations described above should not be understood as requiring such separation in all implementations, and it should be understood that the described components and systems can generally be integrated together in a single product or packaged into multiple products.

Conditional language used herein, such as, among others, "can," "could," "might," "may," "e.g.," and the like, unless specifically stated otherwise, or otherwise understood within the context as used, is generally intended to convey that certain features, elements, and/or steps are optional. Thus, such conditional language is not generally intended to imply that features, elements, and/or steps are in any way required or that one or more embodiments necessarily include logic for deciding, with or without other input or prompting, whether these features, elements, and/or steps are included or are to be always performed. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 10 degrees, 5 degrees, 3 degrees, or 1 degree. As another example, in certain embodiments, the terms "generally perpendicular" and "substantially perpendicular" refer to a value, amount, or characteristic that departs from exactly perpendicular by less than or equal to 10 degrees, 5 degrees, 3 degrees, or 1 degree.

While the above detailed description has shown, described, and pointed out novel features, it can be understood that various omissions, substitutions, and changes in the form and details of the devices or systems illustrated can be made without departing from the spirit of the disclosure. As can be recognized, certain portions of the description herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A low dead space airway adapter for sampling fluid flowing through a ventilation assembly, the airway adapter comprising:

a first outer wall configured to couple to an endotracheal (ET) tube adapter, the first outer wall defining a first internal cavity;

a second outer wall configured to couple to a flow sensor or a ventilation tube connector, the second outer wall defining a second internal cavity;

a barrier wall positioned between the first and second internal cavities of the first and second outer walls, the barrier wall comprising a barrier wall opening;

a first internal projection positioned within the first internal cavity defined by the first outer wall and spaced from an interior surface of the first outer wall, the first internal projection extending outward from the barrier wall and extending around an entirety of said barrier wall opening, the first internal projection extending beyond a free end of the first outer wall and configured to extend into an internal cavity of the ET tube adapter when the first outer wall is coupled to the ET tube adapter, the first internal projection comprising:

a first end connected to the barrier wall;

a second end opposite the first end;

a first fluid passageway extending between the first and second ends; and an opening at the second end, wherein the opening of the first internal projection is in fluid communication with the first fluid passageway and the barrier wall opening and wherein the second end of the first internal projection comprises a curved chamfer that extends around an entirety of the opening of the first internal projection;

a second internal projection positioned within the second internal cavity defined by the second outer wall and spaced from an interior surface of the second outer wall, the second internal projection extending outward from the barrier wall in an opposite direction as the first internal projection and extending around the entirety of said barrier wall opening, the second internal projection comprising:

a first end connected to the barrier wall;

a second end opposite the first end of the second internal projection, wherein the second end of the second internal projection is spaced inward from a free end of the second outer wall within the second internal cavity defined by the second outer wall; and a second fluid passageway extending between the first and second ends of the second internal projection, the second fluid passageway in fluid communication with the barrier wall opening and the first fluid passageway of the first internal projection; and a sampling portion comprising at least one fluid passageway in fluid communication with the first fluid passageway, the barrier wall opening, and the second fluid passageway, the sampling portion configured to allow sampling of a portion of fluid flowing through at least one of the first and second fluid passageways when the airway adapter is in use;

wherein the first internal projection is neither compressible nor extendable.

2. The low dead space airway adapter of claim 1, wherein the opening at the second end of the first internal projection is circular.

3. The low dead space airway adapter of claim 1, wherein the second end of the first internal projection is chamfered at an angle relative to a plane extending along the second end of the first internal projection that is between approximately 40 degrees and approximately 50 degrees.

4. The low dead space airway adapter of claim 1, wherein the second internal projection comprises an internal cavity defining said second fluid passageway, said internal cavity of the second internal projection having a first portion and a second portion, the first portion positioned closer to the barrier wall opening than the second portion, the first portion having a cross-sectional area that is smaller than a cross-sectional area of the second portion, the second portion configured to receive and secure to a portion of the flow sensor and facilitate fluid communication between the second fluid passageway and a fluid passageway of the flow sensor.

5. The low dead space airway adapter of claim 4, wherein the first portion of the internal cavity of the second internal projection extends along a greater portion of a length of the internal cavity of the second internal projection than the second portion of the internal cavity of the second internal projection.

6. A low dead space airway adapter for sampling fluid flowing through a ventilation assembly, the airway adapter comprising:

a first outer wall configured to couple to an endotracheal (ET) tube adapter, the first outer wall defining a first internal cavity;

a second outer wall configured to couple to a flow sensor or a ventilation tube connector, the second outer wall defining a second internal cavity;

a barrier wall positioned between the first and second internal cavities of the first and second outer walls, the barrier wall comprising a barrier wall opening;

a first internal projection positioned within the first internal cavity defined by the first outer wall and spaced from an interior surface of the first outer wall, the first internal projection extending outward from the barrier wall and extending around an entirety of said barrier wall opening, the first internal projection extending beyond a free end of the first outer wall and configured to extend into an internal cavity of the ET tube adapter when the first outer wall is coupled to the ET tube adapter, the first internal projection comprising:

a first end connected to the barrier wall;

a second end opposite the first end;

a first fluid passageway extending between the first and second ends; and an opening at the second end, wherein the opening of the first internal projection is in fluid communication with the first fluid passageway and the barrier wall opening and wherein the second end of the first internal projection is chamfered around an entirety of the opening of the first internal projection; and a sampling portion comprising at least one fluid passageway in fluid communication with the first fluid passageway and the barrier wall opening, the sampling portion configured to allow sampling of a portion of fluid flowing through the first fluid passageway when the airway adapter is in use;

wherein the first internal projection is neither compressible nor extendable; and wherein the airway adapter further comprises a second internal projection positioned within the second internal cavity defined by the second outer wall and spaced from an interior surface of the second outer wall, the second internal projection extending outward from the barrier wall in an opposite direction as the first internal projection and extending around the entirety of said barrier wall opening.

7. The low dead space airway adapter of claim 6, wherein the second end of the internal projection is chamfered at an angle relative to a plane extending along the second end of the internal projection that is between approximately 40 degrees and approximately 50 degrees.

8. The low dead space airway adapter of claim 6, wherein the second internal projection comprises:

a first end connected to the barrier wall;

a second end opposite the first end of the second internal projection; and a second fluid passageway extending between the first and second ends of the second internal projection, the second fluid passageway in fluid communication with the barrier wall opening and the first fluid passageway of the first internal projection.

9. The low dead space airway adapter of claim 8, wherein the second end of the second internal projection is spaced inward from a free end of the second outer wall and has a length that is smaller than the first internal projection.

10. A low dead space airway adapter for sampling fluid flowing through a ventilation assembly, the airway adapter comprising:

a first outer wall configured to couple to an endotracheal (ET) tube adapter, the first outer wall defining a first internal cavity;

a second outer wall configured to couple to a flow sensor or a ventilation tube connector, the second outer wall defining a second internal cavity;

a barrier wall positioned between the first and second internal cavities of the first and second outer walls, the barrier wall comprising a barrier wall opening;

a first internal projection positioned within the first internal cavity defined by the first outer wall, the first internal projection extending outward from the barrier wall and extending at least partially around said barrier wall opening, the first internal projection configured to extend into an internal cavity of the ET tube adapter when the first outer wall is coupled to the ET tube adapter, the first internal projection comprising:

a first end connected to the barrier wall;

a second end opposite the first end;

a first fluid passageway extending between the first and second ends; and an opening at the second end, wherein the opening of the first internal projection is in fluid communication with the first fluid passageway and the barrier wall opening and wherein the second end of the first internal projection is at least partially chamfered around the opening of the first internal projection;

wherein the first internal projection is neither compressible nor extendable; and wherein the airway adapter further comprises a second internal projection positioned within the second internal cavity defined by the second outer wall, the second internal projection extending outward from the barrier wall in an opposite direction as the first internal projection and extending at least partially around said barrier wall opening.

11. The low dead space airway adapter of claim 10, further comprising a sampling portion comprising at least one fluid passageway in fluid communication with the first fluid passageway and the barrier wall opening, the sampling portion configured to allow sampling of a portion of fluid flowing through the first fluid passageway when the airway adapter is in use.

12. The low dead space airway adapter of claim 10, wherein the opening at the second end of the internal projection is circular.

13. The low dead space airway adapter of claim 10, wherein the internal projection extends beyond a free end of the first outer wall.

14. The low dead space airway adapter of claim 10, wherein the second internal projection comprises:

a first end connected to the barrier wall;

a second end opposite the first end of the second internal projection; and a second fluid passageway extending between the first and second ends of the second internal projection, the second fluid passageway in fluid communication with the barrier wall opening and the first fluid passageway of the first internal projection.

15. The low dead space airway adapter of claim 14, wherein:

the second end of the second internal projection is spaced inward from a free end of the second outer wall within the second internal cavity defined by the second outer wall;

a first plane extending along the second end of the second internal projection partitions the second internal cavity into a first portion and a second portion, the second portion being positioned between said first plane and a second plane extending along the free end of the second outer wall; and a total interior volume of the first fluid passageway, the second fluid passageway, and the second portion of the second internal cavity is less than approximately 2.5 ml.

16. The low dead space airway adapter of claim 14, wherein the second internal projection comprises an internal cavity defining said second fluid passageway, said internal cavity of the second internal projection having a first portion and a second portion, the first portion positioned closer to the barrier wall opening than the second portion, the first portion having a cross-sectional area that is smaller than a cross-sectional area of the second portion, the second portion configured to receive and secure to a portion of the flow sensor and facilitate fluid communication between the second fluid passageway and a fluid passageway of the flow sensor.

* * * * *